US012012633B2

(12) United States Patent
Ludwig et al.

(10) Patent No.: US 12,012,633 B2
(45) Date of Patent: Jun. 18, 2024

(54) LINEAGE TRACING USING MITOCHONDRIAL GENOME MUTATIONS AND SINGLE CELL GENOMICS

(71) Applicants: The Broad Institute, Inc., Cambridge, MA (US); Massachusetts Institute of Technology, Cambridge, MA (US); The Children's Medical Center Corporation, Boston, MA (US); President and Fellows of Harvard College, Cambridge, MA (US)

(72) Inventors: Leif S. Ludwig, Cambridge, MA (US); Caleb A. Lareau, Boston, MA (US); Jacob C. Ulirsch, Boston, MA (US); Aviv Regev, Cambridge, MA (US); Vijay G. Sankaran, Boston, MA (US); Jason Buenrostro, Cambridge, MA (US); Christoph Muus, Cambridge, MA (US)

(73) Assignees: The Broad Institute, Inc., Cambridge, MA (US); Massachusetts Institute of Technology, Cambridge, MA (US); The Children's Medical Center Corporation, Boston, MA (US); President and Fellows of Harvard College, Cambridge, MA (US)

( * ) Notice: Subject to any disclaimer, the term of this patent is extended or adjusted under 35 U.S.C. 154(b) by 616 days.

(21) Appl. No.: 17/251,451

(22) PCT Filed: Jun. 11, 2019

(86) PCT No.: PCT/US2019/036583
§ 371 (c)(1),
(2) Date: Dec. 11, 2020

(87) PCT Pub. No.: WO2019/241273
PCT Pub. Date: Dec. 19, 2019

(65) Prior Publication Data
US 2021/0246503 A1 Aug. 12, 2021

Related U.S. Application Data

(60) Provisional application No. 62/838,639, filed on Apr. 25, 2019, provisional application No. 62/683,502, filed on Jun. 11, 2018.

(51) Int. Cl.
*C12Q 1/68* (2018.01)
*A61K 45/06* (2006.01)
*C12Q 1/6827* (2018.01)
*C12Q 1/6869* (2018.01)
*C12Q 1/6886* (2018.01)

(52) U.S. Cl.
CPC .......... *C12Q 1/6869* (2013.01); *A61K 45/06* (2013.01); *C12Q 1/6827* (2013.01); *C12Q 1/6886* (2013.01)

(58) Field of Classification Search
CPC .................................................... C12Q 1/6869
See application file for complete search history.

(56) References Cited

U.S. PATENT DOCUMENTS

2021/0032702 A1* 2/2021 Bernstein ............. C12Q 1/6881

FOREIGN PATENT DOCUMENTS

| WO | 02101086 A2 | 12/2002 |
| WO | 2005056573 A1 | 6/2005 |
| WO | 2016019149 A1 | 2/2016 |

OTHER PUBLICATIONS

Fellous, et al., "A Methodological Approach to Tracing Cell Lineage in Human Epithelial Tissues", Stem Cells, 27(6), Jun. 2009, pp. 1410-1420.
Floros, et al., "Segregation of Mitochondrial DNA Heteroplasmy Through a Developmental Genetic Bottleneck in Human Embryos", Nature Cell Biology, 20(2), Jan. 2018, pp. 144-151.
Ludwig, et al., "Lineage Tracing in Humans Enabled by Mitochondrial Mutations and Singe-Cell Genomics", Cell, vol. 176, No. 6, Mar. 7, 2019, 38 pages.
McKenna, et al., "Recording Development with Single Cell Dynamic Lineage Tracing", Development, 146(12), Jun. 2019, pp. 1-10.
Ni, et al., "MitoRCA-seq Reveals Unbalanced Cytocine to Thymine Transition in Polg Mutation Mice", Scientific Reports, 5(1), Jul. 2015, pp. 1-13.
Taylor, et al., "Mitochondrial DNA Mutations in Human Colonic Crypt Stem Cells", Journal of Clinical Investigation, vol. 112, No. 9, 2003, 11 pages.
Teixeira, et al., "Stochastic Homeostasis in Human Airway Epithelium is Achieved by Neutral Competition of Basal Cell Progenitors", eLife, vol. 2, 2013, 18 pages.

(Continued)

*Primary Examiner* — Kenneth R Horlick
(74) *Attorney, Agent, or Firm* — Nixon Peabody LLP; David S. Resnick; Jeanne Nicole Jodoin

(57) ABSTRACT

Embodiments disclosed herein provide methods of using somatic mutations in mitochondrial genomes to retrospectively infer cell lineages in native contexts and to serve as genetic barcodes to measure clonal dynamics in complex cellular populations. Further, somatic mutations in mitochondrial DNA (mtDNA) are tracked by single cell genomic approaches for simultaneous analysis of single cell lineage and state. Applicants further show that mitochondrial mutations can be readily detected with contemporary single cell transcriptomic and epigenomic technologies to concomitantly capture gene expression profiles and chromatin accessibility, respectively.

27 Claims, 38 Drawing Sheets

(56) References Cited

OTHER PUBLICATIONS

The Broad Institute, Inc., et al., "Notification of Transmittal of the International Search Report and the Written Opinion of the International Searching Authority, or the Declaration for PCT/US2019/036583", Sep. 5, 2019, 15 pages.
Walther, et al., "Cell Lineage Tracing in Human Epithelial Tissues Using Mitochondrial DNA Mutations as Clonal Markers", Wiley Interdisciplinary Reviews, Developmental Biology, 5(1), Jan. 2016, pp. 103-117.
Xu, et al., "Single-Cell Lineage Tracing by Endogenous Mutations Enriched in Transposase Accessible Mitochondrial DNA", ELife, 2019, pp. 1-14.
Yao, et al., "Mitochondrial DNA Mutations in Single Human Blood Cells", Mutation Research, 779, Sep. 2015, pp. 68-77.
Ye, et al., "Extensive Pathogenicity of Mitochondrial Heteroplasmy in Healthy Human Individuals", Proceedings of the National Academy of Sciences of the United States of America, vol. 111, No. 29, Jul. 22, 2014, 10654-10659.

* cited by examiner

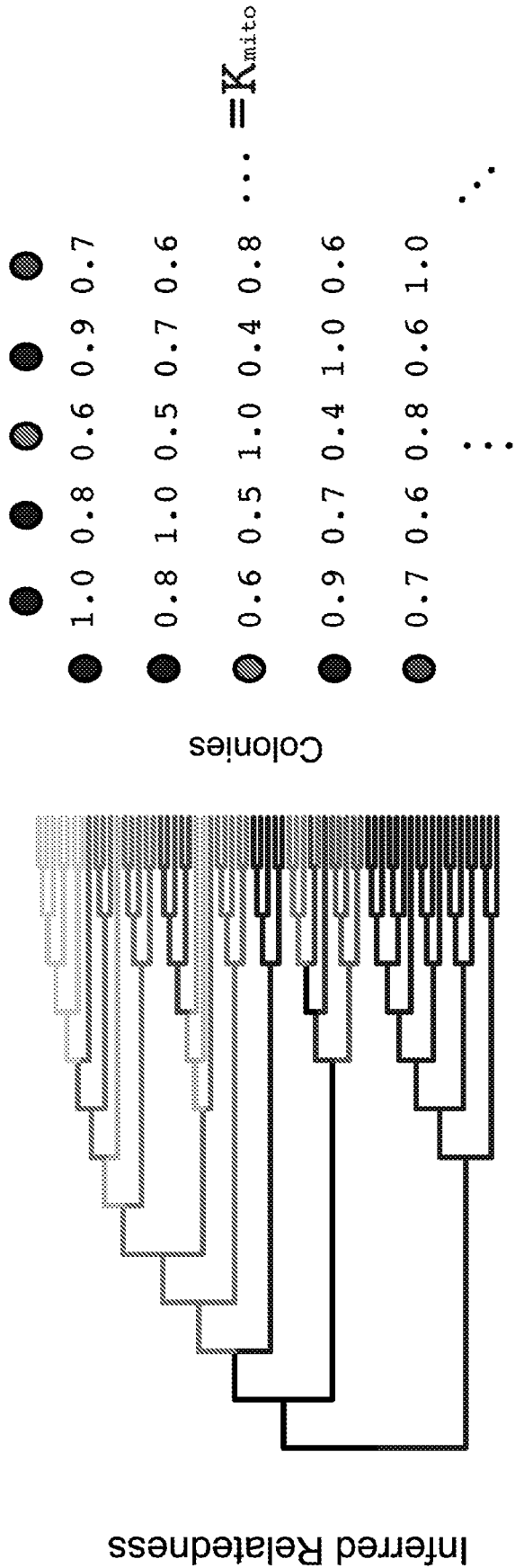
FIG. 1E
FIG. 1G
Variance Decomposition
$$Y \sim N(0, \; \sigma^2 K_{mito} + \sigma^2 I)$$
Peak Accessibility
FIG. 1H
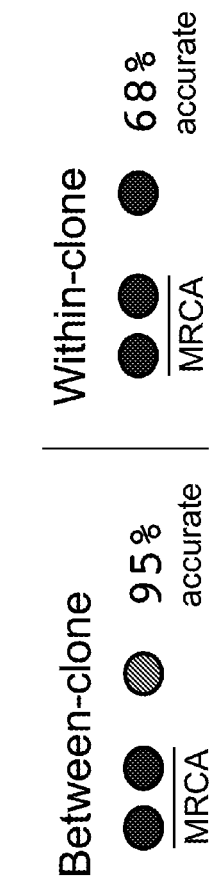
FIG. 1F

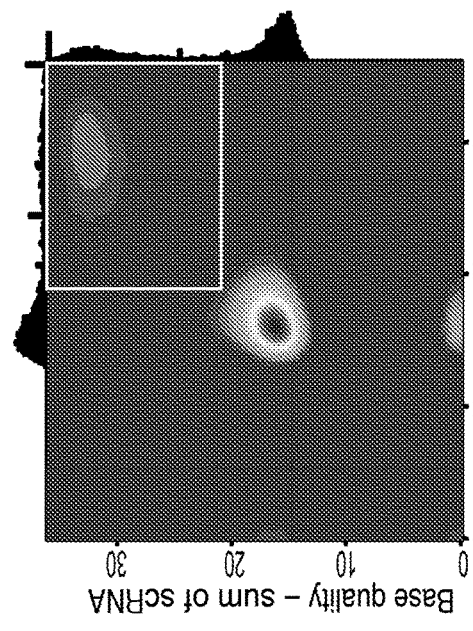
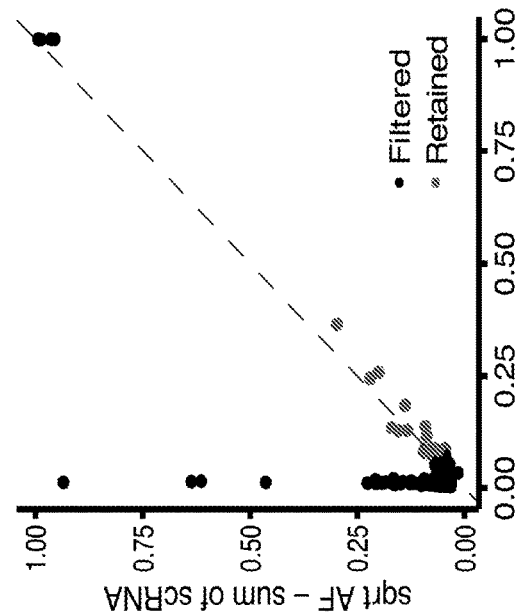
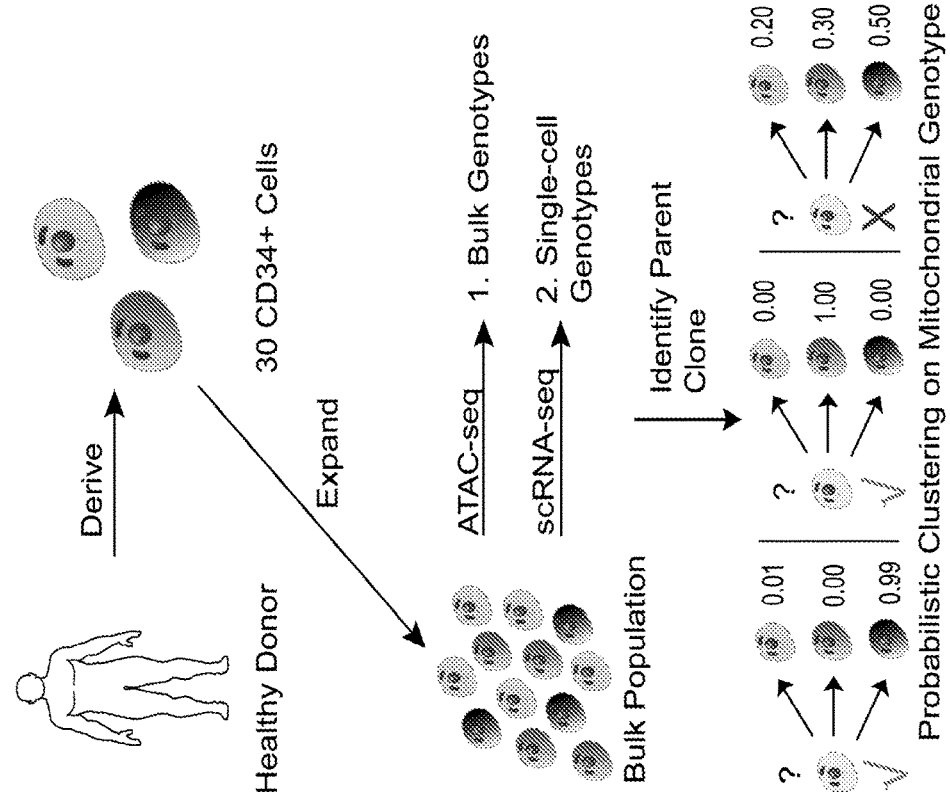
FIG. 4A
FIG. 4B
FIG. 4C

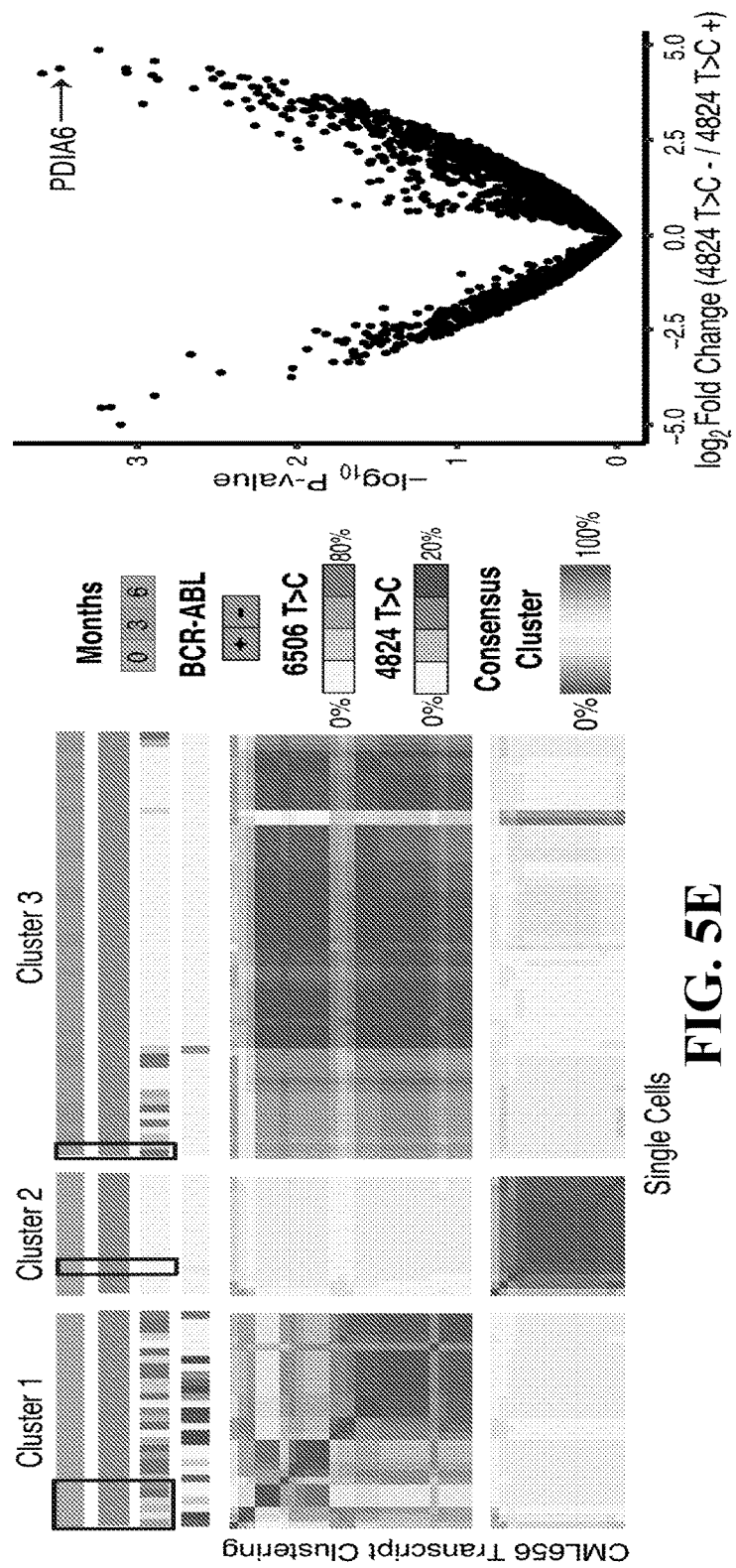
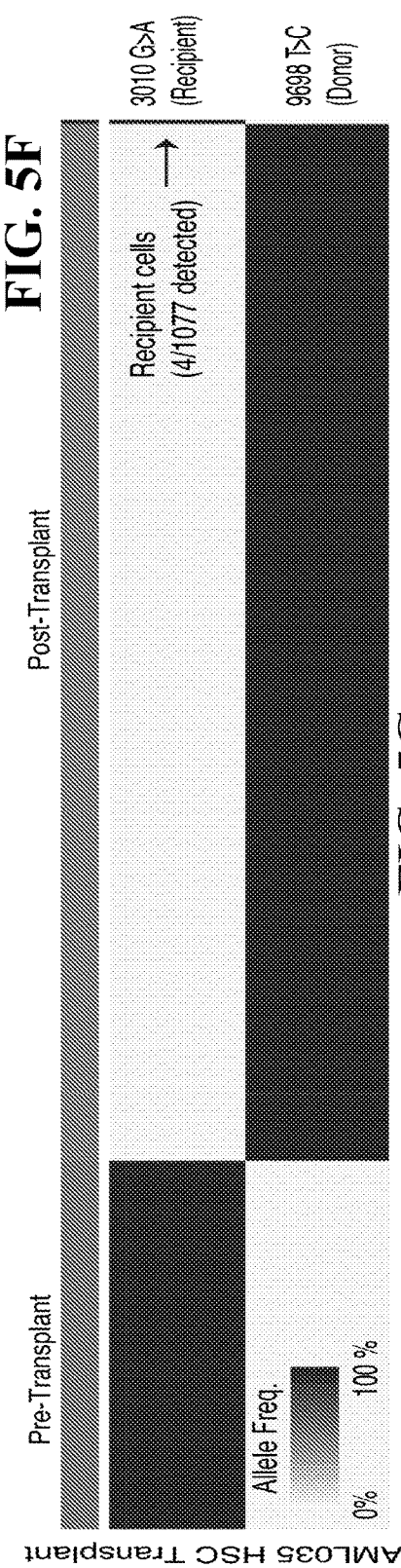
FIG. 5E
FIG. 5F
FIG. 5G

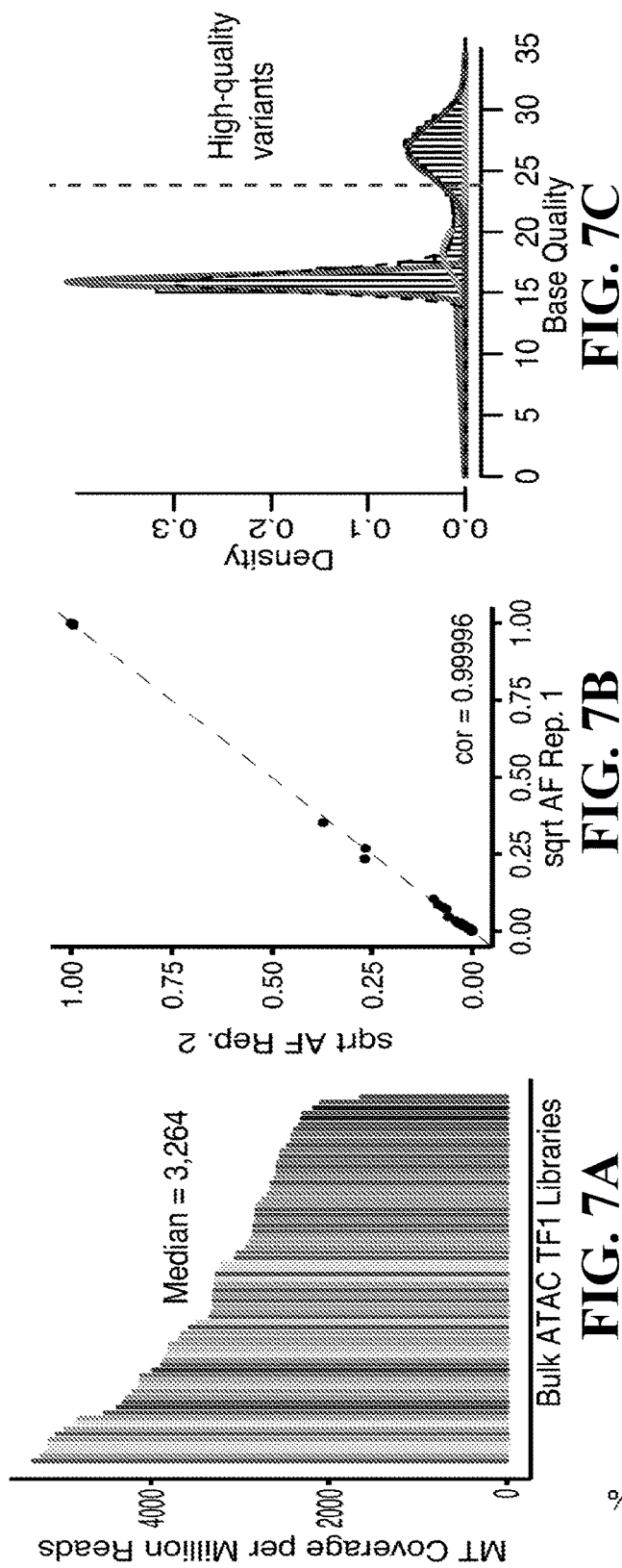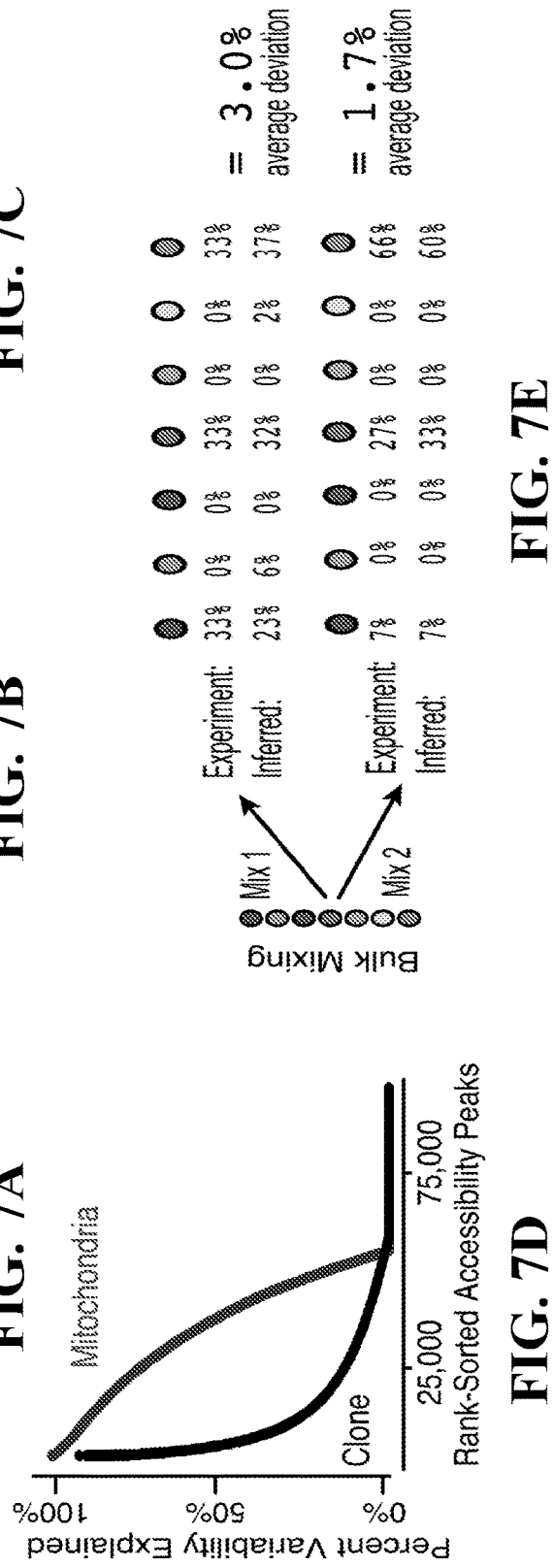

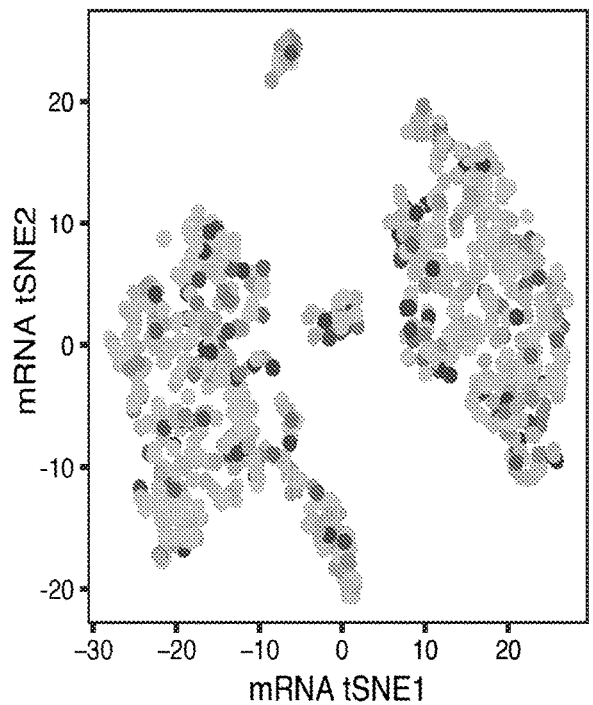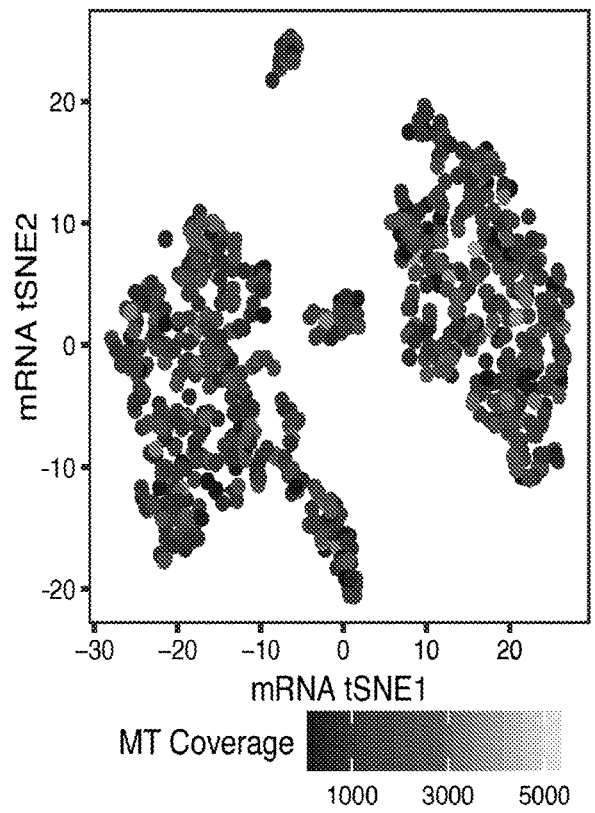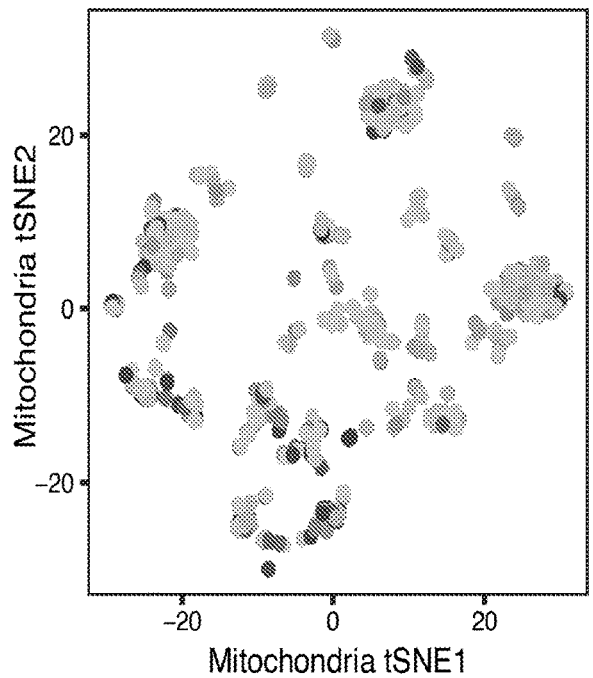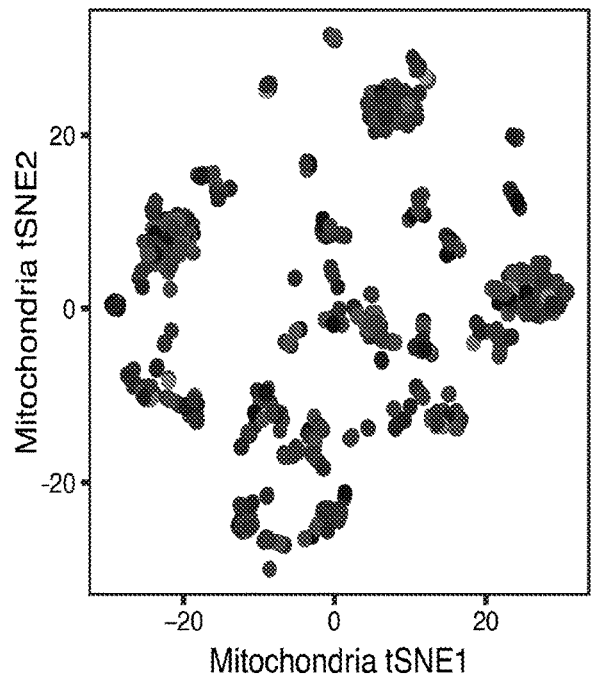
FIG. 9A          FIG. 9B

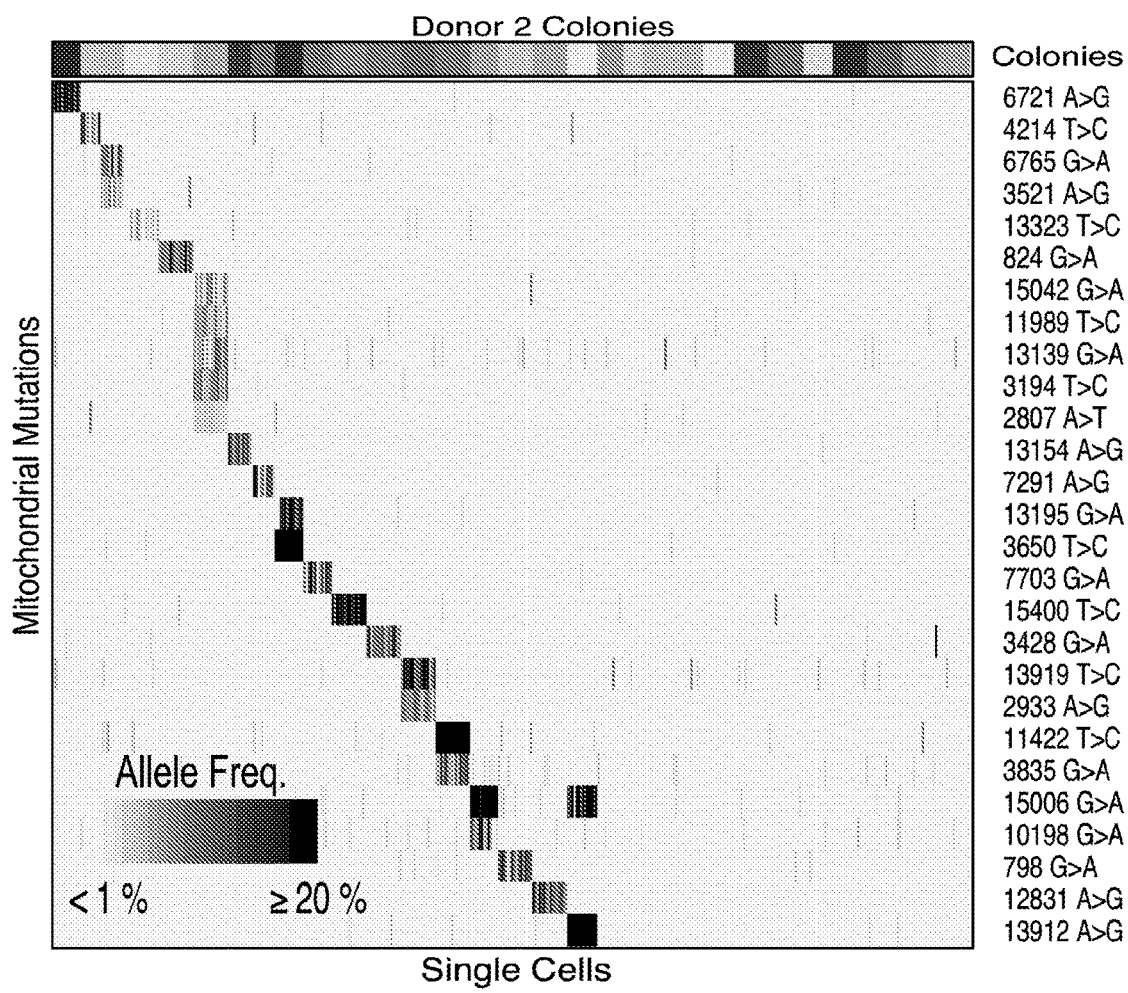
FIG. 9C
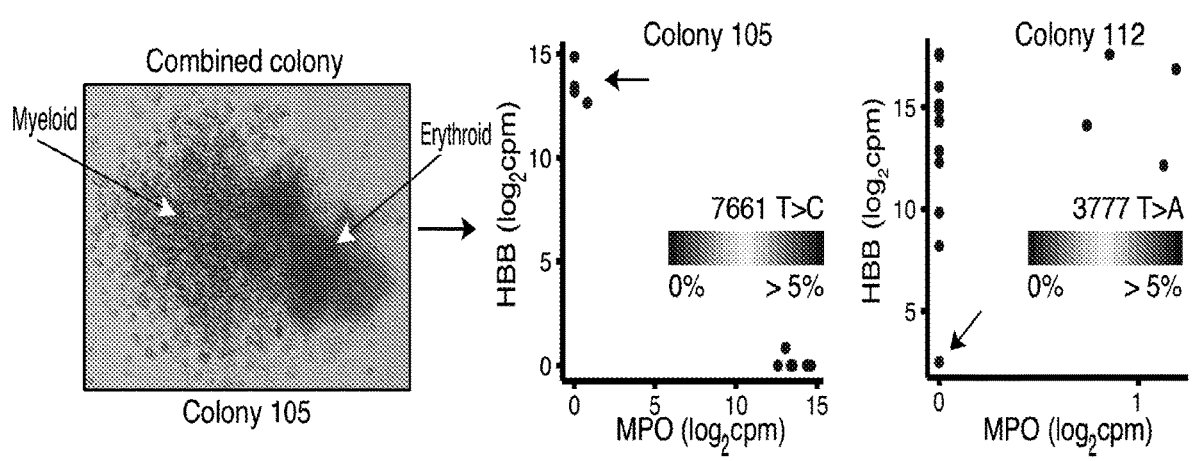
FIG. 9D
FIG. 9E

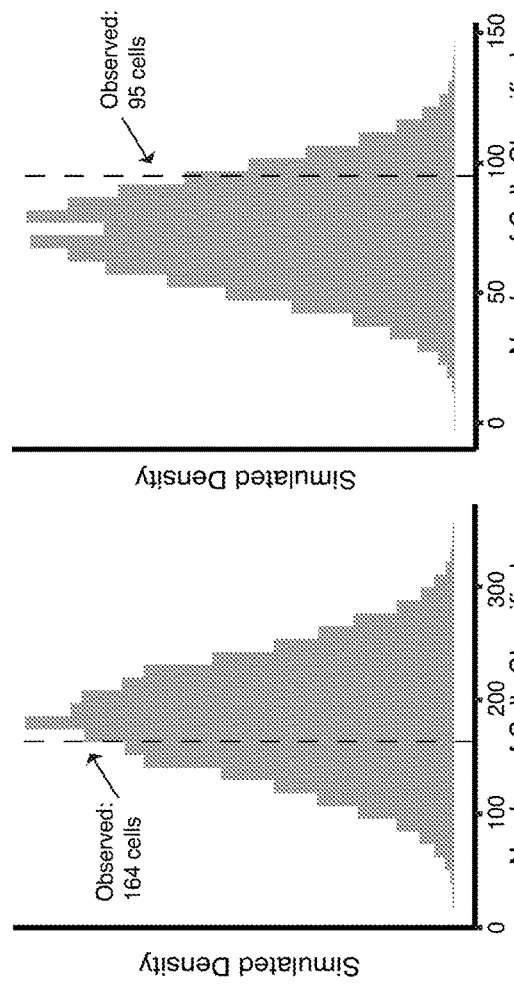
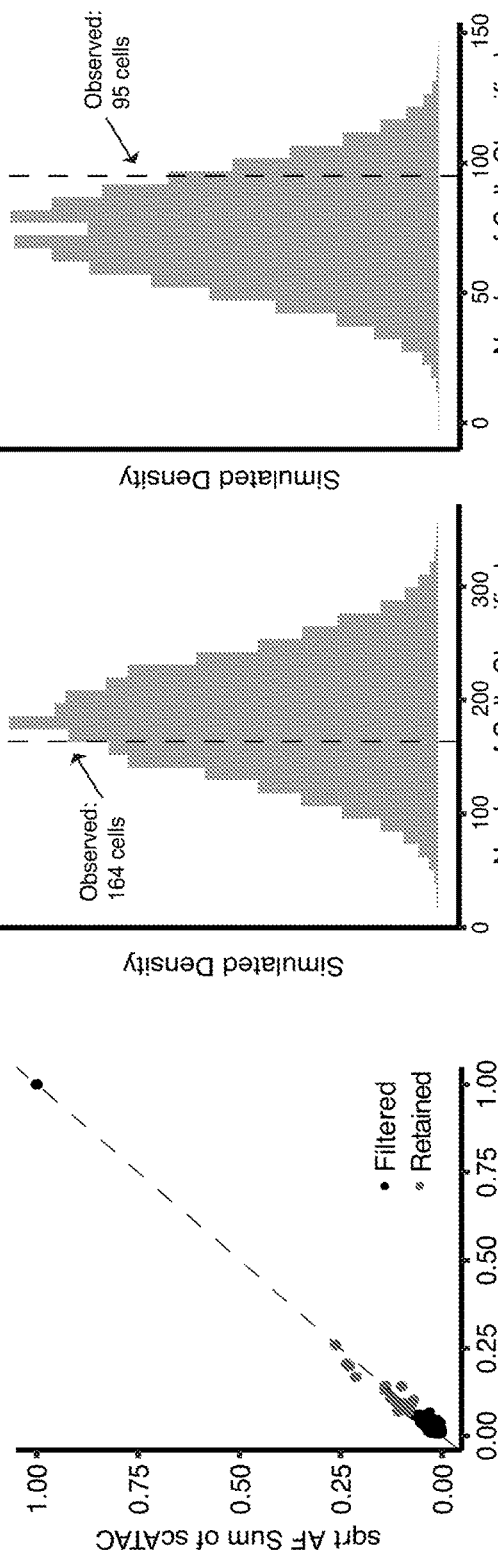
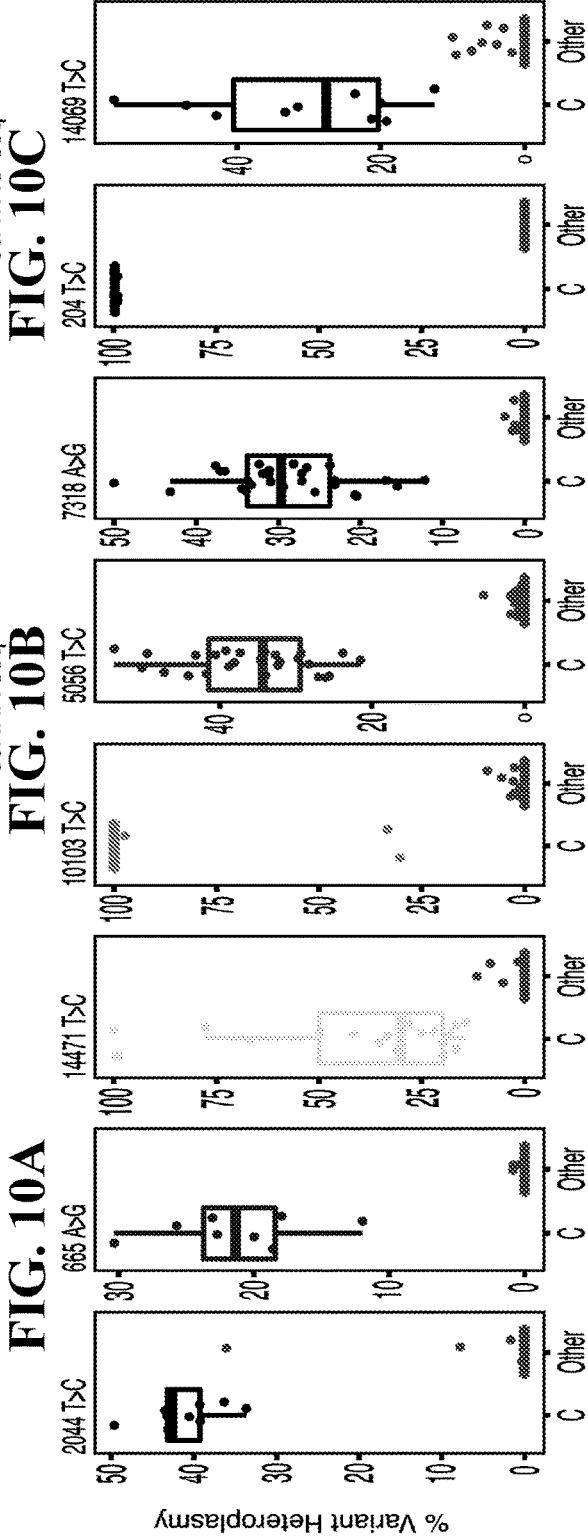
FIG. 10A
FIG. 10B
FIG. 10C
FIG. 10D

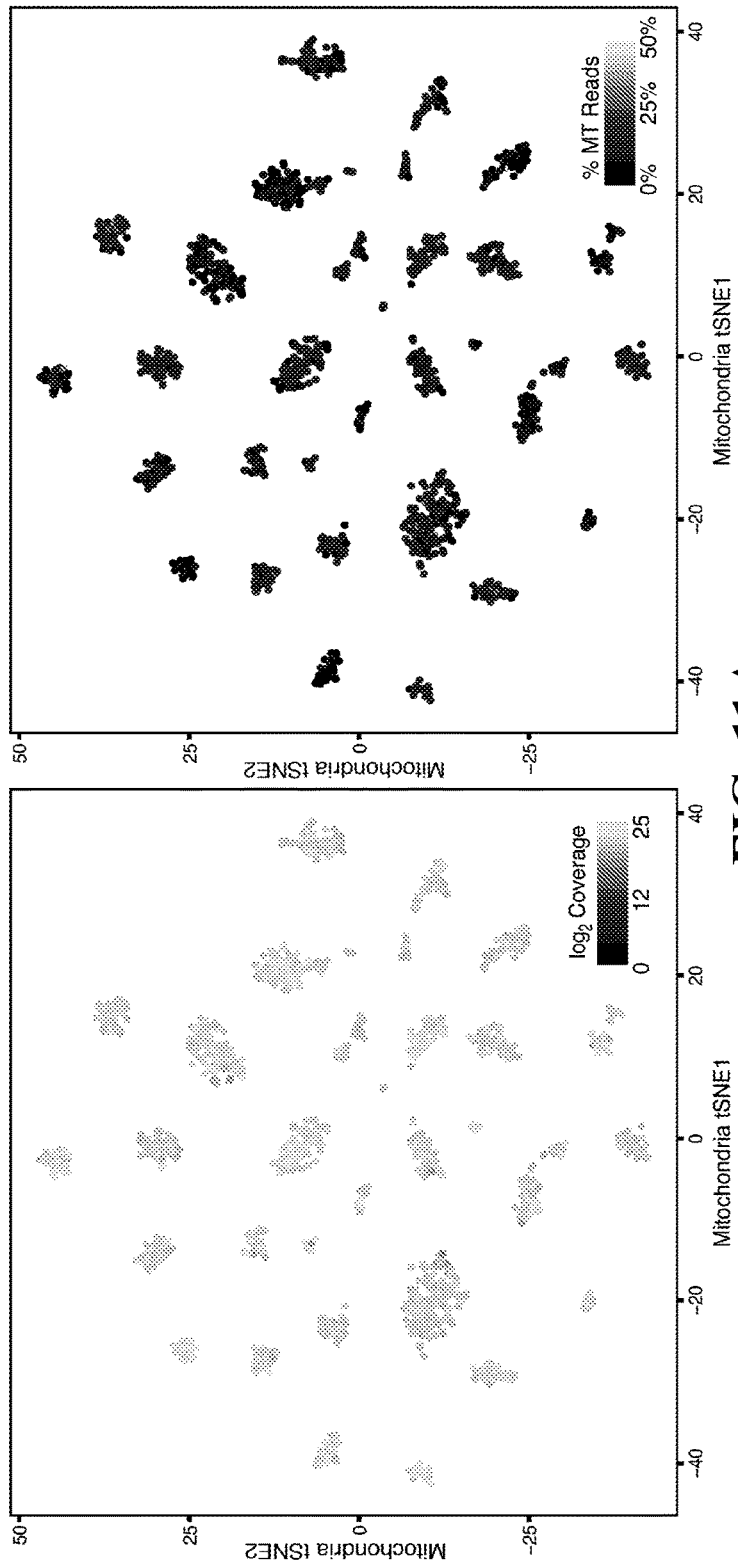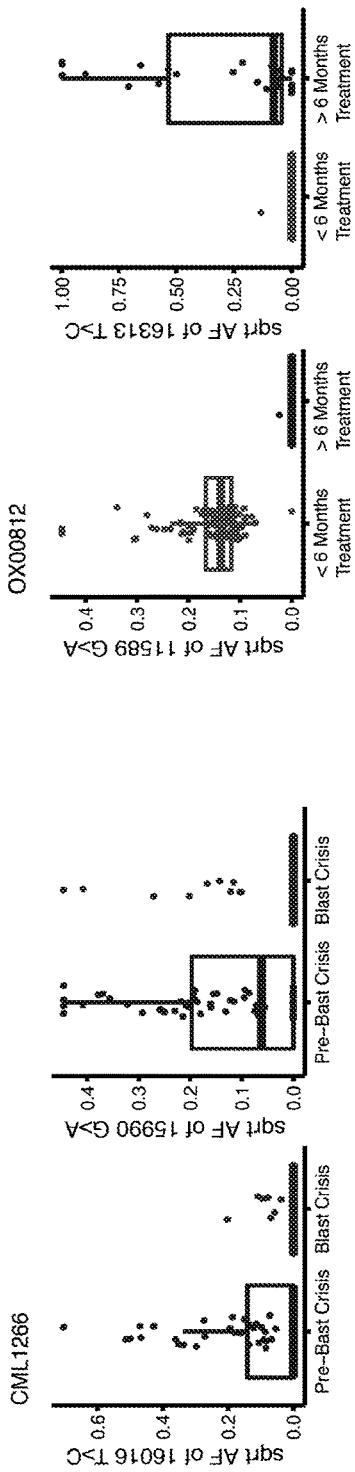
FIG. 11A
FIG. 11B
FIG. 11C

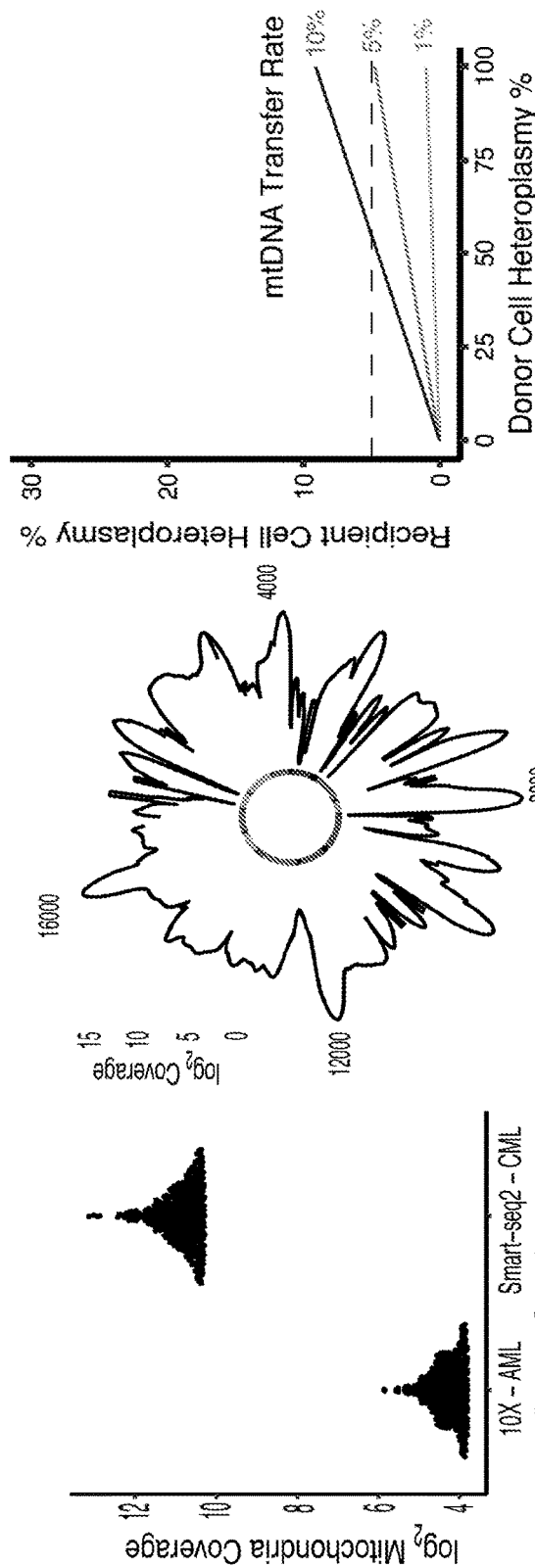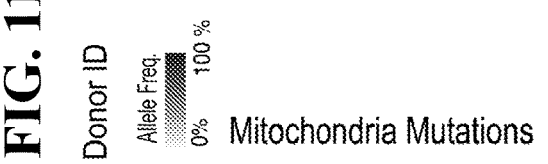

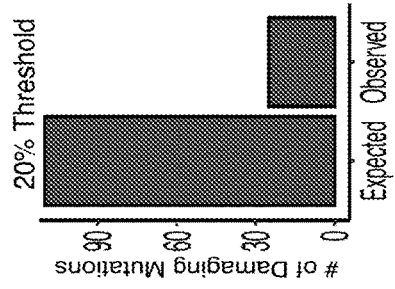
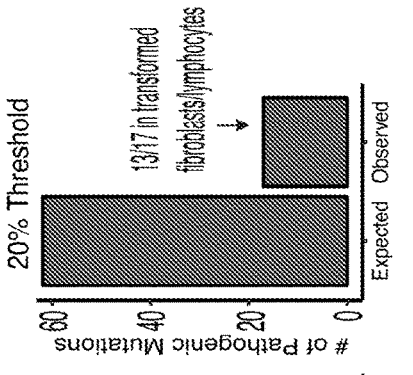
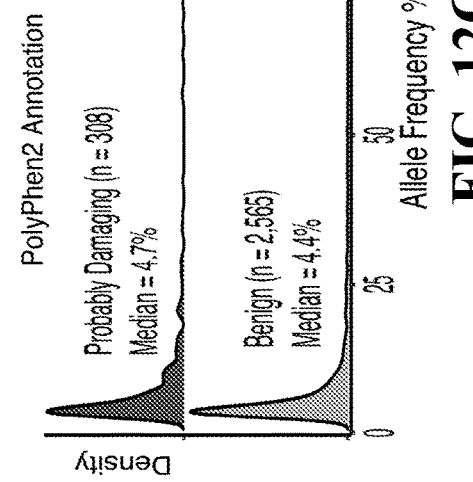
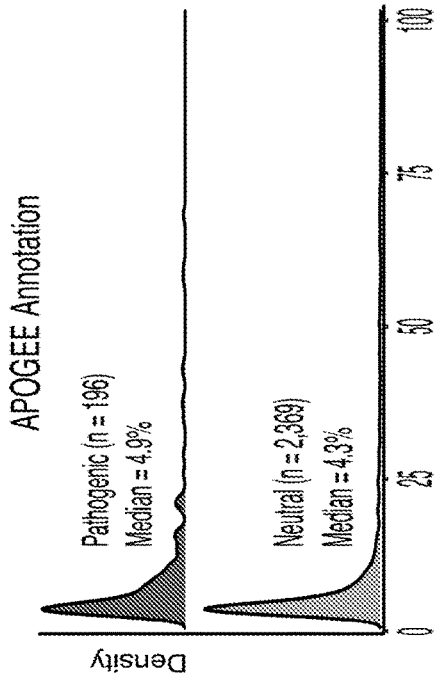
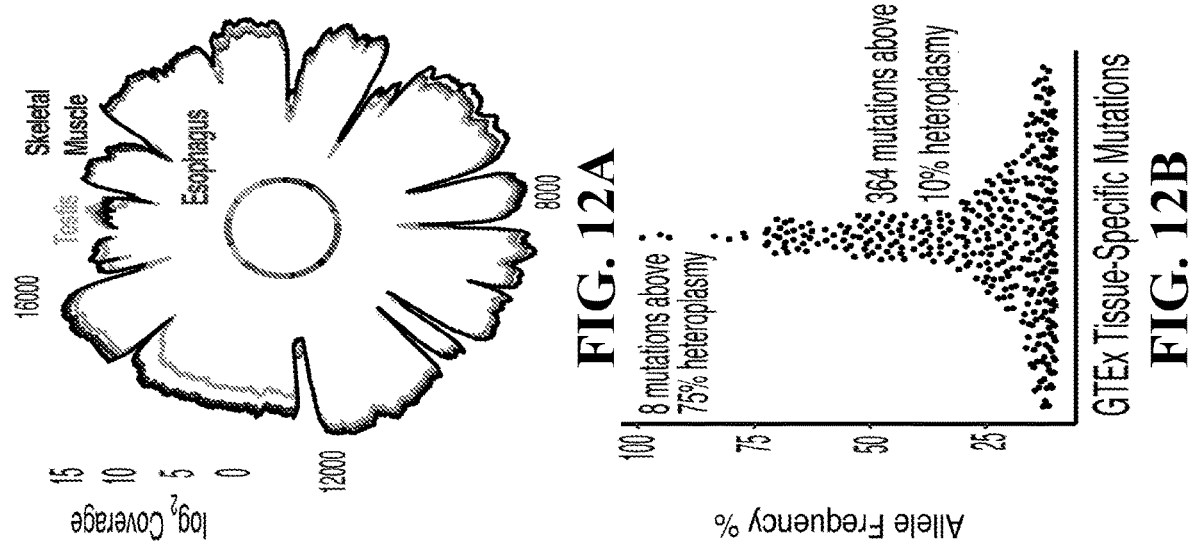

LINEAGE TRACING USING MITOCHONDRIAL GENOME MUTATIONS AND SINGLE CELL GENOMICS

CROSS-REFERENCE TO RELATED APPLICATIONS

This application claims the benefit of U.S. Provisional Application Nos. 62/683,502, filed Jun. 11, 2018 and 62/838,639, filed Apr. 25, 2019. The entire contents of the above-identified applications are hereby fully incorporated herein by reference.

STATEMENT REGARDING FEDERALLY SPONSORED RESEARCH

This invention was made with government support under Grant Nos. DK103794 and HL120791 awarded by the National Institutes of Health. The government has certain rights in the invention.

TECHNICAL FIELD

The subject matter disclosed herein is generally directed to inferring cell lineages in native contexts and measuring clonal dynamics in complex cellular populations.

BACKGROUND

All cells in the human body are derived from the zygote, but we lack a detailed map integrating cell division (lineage) and differentiation (fate) and their dynamics from stem cells to their differentiated progeny. Such a map would significantly expand our understanding of cellular processes underlying human development, tissue homeostasis, and disease. To date, C. elegans remains the only multicellular organism in which the fate of every cell has been mapped and assembled into a complete organismal lineage tree (1). However, the direct approach applied in the developing nematode, where each of 1,031 cells was directly observed by microscopy, cannot be applied in larger, more complex, and less stereotyped organisms.

Two sets of alternatives have been developed to study cellular relationships and clonal dynamics in increasingly complex tissues. In model organisms, most approaches to date (2) rely on an engineered genetic label to tag individual cells or populations with heritable marks such as fluorescent or reporter genes, high diversity DNA barcode libraries, mobile transposable elements, Polylox/Cre, or CRISPR-based barcodes (3-6). In human tissues in vivo, where such genetic manipulations are not readily possible (7), we must rely on naturally occurring somatic mutations, including single nucleotide variants (SNVs), copy number variants (CNVs), and variation in short tandem repeat sequences (microsatellites or STRs), which are stably propagated to daughter cells, but absent in distantly related cells (8, 9).

Although single cell approaches have been developed to detect somatic mutations in the nuclear genome in human cells, they are costly, difficult to apply at scale, have substantial error rates, and do not provide information on cell state. In particular, reliable mutation detection from a single genomic copy remains technically challenging (10-12), with high error rates during whole genome amplification of single cells, leading to allelic dropout, false positive artifacts, and non-uniform coverage (13-15). Moreover, single-cell sequencing of the entire human genome is cost-prohibitive and currently has limited throughput. Finally, most methods have not been or cannot be readily combined with methods that would report on the cell type and state based on RNA profiles or chromatin organization.

SUMMARY

In one aspect, the present invention provides for a method of determining a lineage and/or clonal structure of single cells in a multicellular eukaryotic organism comprising: detecting mutations in mitochondrial genome sequencing reads of single cells obtained from a subject; and clustering the cells based on the presence of the mutations in the single cells, whereby a lineage and/or clonal structure for the single cells is retrospectively inferred. As used herein the terms "retrospectively inferred" refer to determining a cell lineage or clonal structure after the lineage or clonal structure has formed as opposed to observing cells as they divide and generate a cell lineage or clonal populations. In certain embodiments, the method comprises sequencing the mitochondrial genomes in single cells obtained from the subject. Thus, the method can be performed on a sequencing data set already generated.

In certain embodiments, the mutations are detected in at least 5 sequencing reads and have at least 0.5% heteroplasmy in the single cells obtained from the subject. In certain embodiments, the mutations have at least 5% heteroplasmy in the single cells obtained from the subject.

In certain embodiments, the method further comprises detecting mutations in mitochondrial genome sequencing reads of a bulk sample obtained from the subject, wherein step (a) further comprises selecting heteroplasmic mutations detected in the bulk sample. In certain embodiments, the method comprises sequencing mitochondrial genomes in a bulk sample obtained from the subject. Thus, the method can be performed on a bulk sequencing data set already generated. The bulk sequencing may comprise DNA-seq, RNA-seq, ATAC-seq or RCA-seq. DNA-seq may comprise whole genome, whole exome or targeted sequencing. In certain embodiments, the selected mutations are detected in at least 5 sequencing reads and have at least 0.5% heteroplasmy in the bulk sample obtained from the subject.

In certain embodiments, the mutations are detected in the D loop of the mitochondrial genomes.

In certain embodiments, the method further comprises detecting mutations in the nuclear genome and clustering the cells based on the presence of the mitochondrial and nuclear genome mutations in the single cells. In certain embodiments, the method comprises sequencing the nuclear genome in single cells obtained from the subject.

In certain embodiments, the detected mutations have a Phred quality score greater than 20. Thus, the mutations detected for determining a lineage or clonal structure are selected based on a base quality score.

In certain embodiments, the clustering is hierarchical clustering. In certain embodiments, the method further comprises generating a lineage map.

In certain embodiments, detecting mutations in single cells comprises lysing the cells under conditions capable of lysing mitochondria. Prior methods for sequencing a transcriptome may have milder conditions that are capable of lysing a cell, but not all mitochondria. The lysing conditions may comprise one or more of NP-40™ detergent, Triton X-100™ detergent, SDS, guanidine isothiocyante, guanidine hydrochloride or guanidine thiocyanate.

In certain embodiments, detecting mutations in the mitochondrial genomes and/or nuclear genome of single cells comprises single cell RNA sequencing (scRNA-seq). In certain embodiments, detecting mutations in the mitochondrial genomes and/or nuclear genome comprises analyzing scRNA-seq data obtained from a subject. The method may further comprise excluding RNA modifications, RNA transcription errors and/or RNA sequencing errors from the mutations detected. The RNA modifications may comprise previously identified RNA modifications. These include RNA modifications known in the art and modifications identified by sequencing mitochondrial genomes and comparing the sequences to mitochondrial transcripts. In certain embodiments, RNA modifications, RNA transcription errors and/or RNA sequencing errors are determined by comparing the mutations detected by scRNA-seq to mutations detected by DNA-seq, ATAC-seq or RCA-seq in a bulk sample from the subject. In certain embodiments, the method further comprises determining the cell state of the single cells in the lineage and/or clonal structure by measuring the expression of the nuclear genome obtained by scRNA-seq. Thus, in certain embodiments, scRNA-seq can be used to simultaneously determine mitochondrial mutations, mutations in the transcriptome and gene expression in single cells. Gene expression may be used to determine the transcriptional cell state of the single cells.

In certain embodiments, detecting mutations in the mitochondrial genomes and/or nuclear genome of single cells comprises single cell ATAC-seq (scATAC-seq). In certain embodiments, the method further comprises determining the cell state of the single cells in the lineage and/or clonal structure by measuring chromatin accessibility obtained by scATAC-seq. Thus, in certain embodiments, scATAC-seq can be used to simultaneously determine mitochondrial mutations, mutations in the nuclear genome and chromatin accessibility in single cells. Measuring chromatin accessibility may be used to determine the chromatin cell state of the single cells.

In certain embodiments, heritable cell states are identified. In certain embodiments, the establishment of a cell state along a lineage is identified.

In certain embodiments, the single cells comprise related cell types. The related cell types may be from a tissue. The tissue may be associated with a disease state. The disease may be a degenerative disease. The tissue may be healthy tissue. Thus, healthy tissue may be studied to understand a disease state. The tissue may be diseased tissue. Thus, diseased tissue may be studied to understand a disease state.

In certain embodiments, the cells obtained from a subject are selected for a cell type. In certain embodiments, stem and progenitor cells are selected. CD34+ hematopoietic stem and progenitor cells may be selected (e.g., to study blood diseases). In certain embodiments, the method further comprises determining a lineage and/or clonal structure for single cells from two or more tissues and identifying tissue specific mitochondrial mutations for the subject. In certain embodiments, the related cell types are from a tumor sample. In certain embodiments, peripheral blood mononuclear cells (PBMCs) and/or bone marrow mononuclear cells (BMMCs) are selected. The PBMCs and/or BMMCs may be selected before and after stem cell transplantation in a subject.

In another aspect, the present invention provides for a method of detecting clonal populations of cells in a tumor sample obtained from a subject in need thereof comprising determining the clonal structure for single cells in the tumor sample based on the presence of mutations according to any embodiment herein and on the presence of somatic mutations associated with the cancer, whereby clonal populations of cells are identified based on the presence of the mitochondrial mutations and somatic mutations associated with the cancer in the single cells. The tumor sample may be obtained before a cancer treatment. The method may further comprise obtaining a sample after treatment and comparing the presence of clonal populations before and after treatment, wherein clonal populations of cells sensitive and resistant to the treatment are identified. The cancer treatment may be selected from the group consisting of chemotherapy, radiation therapy, immunotherapy, targeted therapy and a combination thereof.

In another aspect, the present invention provides for a method of identifying a cancer therapeutic target comprising: detecting clonal populations of cells in a tumor sample according to any embodiment herein; identifying differential cell states (e.g., transcriptional or chromatin) between the clonal populations; identifying a cell state present in resistant clonal populations, thereby identifying a therapeutic target. The cell state may be a differentially expressed gene, differentially expressed gene signature, or a differentially accessible chromatin loci.

In another aspect, the present invention provides for a method of treatment comprising administering a treatment targeting a differentially expressed gene, differentially expressed gene signature, or a differentially accessible chromatin loci.

In another aspect, the present invention provides for a method of screening for a cancer treatment comprising: growing a tumor sample obtained from a subject in need thereof, determining clonal populations in the tumor sample based on the presence of mutations according to any embodiment herein; treating the tumor sample with one or more agents; determining the effect of the one or more agents on the clonal populations. The tumor cells may be grown in vitro. The tumor cells may be grown in vivo. The tumor cells may be grown as a patient derived xenograft (PDX). The method may further comprise identifying differential cell states between sensitive and resistant clonal populations.

In another aspect, the present invention provides for a method of identifying changes in clonal populations having a cell state between healthy and diseased tissue comprising determining clonal populations of cells having a cell state in healthy and diseased cells according to claim 1 and comparing the clonal populations. Thus, clonal populations are determined in healthy and diseased tissues. The cell states in the clonal populations can be determined. The tissues may be obtained from the same subject. The cell states are then determined for the clonal populations. Clonal populations shared between the diseased and healthy tissues, as well as clonal populations differentially present or absent between the diseased and healthy tissues can be determined. The present invention allows for improved determination of clonal populations and thus can provide for novel therapeutic targets present in specific populations.

In certain embodiments, the methods of the present invention can be performed using single nuclei isolated from cells. In certain embodiments, nuclei are isolated with enhanced mtDNA yield.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 11—(A) The t-SNE coordinates separating donors from FIG. 5A do not co-vary with the total coverage or the proportion of mitochondrial reads in each cell. (B, C) Specific mutations associated with the patient sub-phenotypes shown in FIG. 5B, C at different timepoints of disease. (D) Plots of the top 500 barcodes and cells from the two public data sources show substantially lower coverage of the mitochondrial transcriptome from the 10× platform. (E) Coverage of all cells analyzed (coverage of all single cells summed together) from the 10× platform. Rounded edges represent 3' ends of transcripts, which are relatively well-covered (compare to FIG. 2E). (F) Simulations of heteroplasmy at different rates of horizontal mtDNA transfer from donor cell (x-axis) to recipient cell (y-axis) assuming fixed mtDNA content per cell. The dashed line indicates a heteroplasmy of 5% in the recipient cell. (G) Heatmap of 164 mutations with near-homoplasmy in one or more samples. Cells were grouped along columns using apriori donor annotations.

FIG. 12—(A) Additional coverage plots across the mitochondrial genome for 3 additional tissues: testis, skeletal muscle, and the esophagus. (B) Depiction of all tissue-specific mutations with a heteroplasmy >10%, including 8 mutations with more than 75% heteroplasmy. Distribution of tissue-specific allele frequencies for variants annotated as protein-damaging from (C) PolyPhen2 and pathogenic from (D) APOGEE shows little variation and a low median heteroplasmy (all medians <5%). The number of observed and expected mutations for protein damaging mutations from (E) PolyPhen2 and pathogenic mutations from (F) APOGEE. Expectations are computed using the product of the number of mutations and the marginal proportions in each category.

Figure 1A:
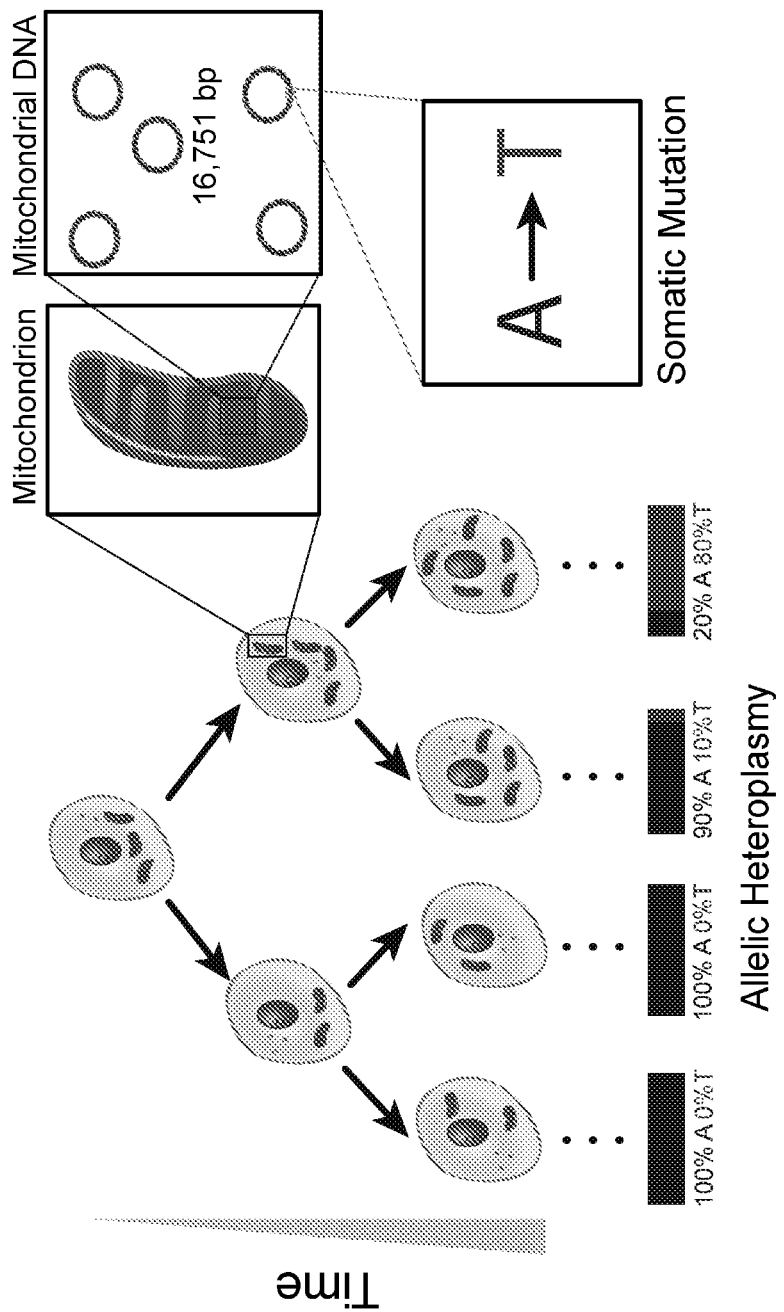
FIG. 1—Mitochondrial mutations are propagated through human cell lineages in vitro. (A) Dynamics of mtDNA heteroplasmy in single cells. Each cell contains multiple mitochondria, which in turn contain many copies of mtDNA that may acquire somatic mutations over time at different heteroplasmy. (B) Proof-of-principle design using TF1 cells to derive clonal lines using single cell sorting. Each clone and sub-clone is assayed with ATAC-seq to generate chromatin accessibility profiles and deep mitochondrial genotypes. (C) Supervised (true) experimental TF1 lineage tree. Colors indicate each primary clone from initial split. (D) Allelic heteroplasmy of four selected variants reveals stable propagation and clone-specificity. (E) Unsupervised hierarchical clustering of TF1 lineage tree. (F) Quantifications of between-clone and within-clone accuracy of identifying the most-recent common ancestor (MRCA) per trio of clones. (G) Schematic of mitochondrial relatedness matrix $K_{mito}$ where each pairs of clones are scored based on mitochondrial genotype similarity. (H) Random effects model for variance decomposition of epigenomic peaks. (I) Two examples of peaks inherited in the clonal lineages. Peaks represent the sum of open chromatin for the clones with the most samples.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboraotry Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to Ludwig, et al., Lineage Tracing in Humans Enabled by Mitochondrial Mutations and Single-Cell Genomics, Cell. 2019 Mar. 7; 176(6):1325-1339.e22. doi: 10.1016/j.cell.2019.01.022. Epub 2019 Feb. 28. All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide methods of using somatic mutations in mitochondrial genomes to retrospectively infer cell lineages in native contexts and to serve as genetic barcodes to measure clonal dynamics in complex cellular populations.

Lineage tracing provides unprecedented insights into the fate of individual cells and their progeny in complex organisms. While effective genetic approaches have been developed in vitro and in animal models, these cannot be used to interrogate human physiology in vivo. Instead, naturally occurring somatic mutations have been utilized to infer clonality and lineal relationships between cells in human tissues, but current approaches are limited by high error rates and scale, and provide little information about the state or function of the cells. Here, Applicants show how somatic mutations in mitochondrial DNA (mtDNA) can be tracked by current single cell genomic approaches for simultaneous analysis of single cell lineage and state.

Somatic mutations in the mitochondrial genome (mtDNA) provide a compelling alternative (16, 17), as multiple studies have shown that each human cell contains hundreds-to-thousands of mitochondrial genomes with diverse and often manifold mutations at detectable levels of heteroplasmy (18-21). Previous studies identified cells with mutations that result in the loss of expression of cytochrome C oxidase (MT-CCO), a gene encoded by the mitochondrial genome (16, 17). Applicants hypothesized that mitochondrial DNA (mtDNA) sequence variation could provide an innate and natural barcode, allowing for inference of lineal relationships and clonal contributions of stem and progenitor cells to complex tissues. Recently, several studies have focused on the dynamics of mitochondrial genetic variation and their relation to disease on a single cell and single organelle level (22, 23). However, the utility of somatic mtDNA mutations, specifically low heteroplasmic mutations, has not been systematically investigated for lineage tracing applications using contemporary scalable single cell genomics, nor have they been combined with cell state profiles.

As disclosed herein, Applicants leverage somatic mtDNA mutations as natural genetic barcodes and demonstrate their use as clonal markers to infer lineal relationships. Applicants trace the lineage of human cells by somatic mtDNA mutations in a native context both in vitro and in vivo. Applicants further show that mitochondrial mutations can be readily detected with contemporary single cell transcriptomic and epigenomic technologies to concomitantly capture gene expression profiles and chromatin accessibility, respectively. The approach can allow lineage tracing at a 100- to 1,000-fold greater scale than with single cell whole genome sequencing, while providing information on cell state, opening the way to chart detailed cell lineage and fate maps in human health and disease.

As disclosed herein, Applicants show that single-cell RNA-Seq (scRNA-seq) and single cell ATAC-Seq (scATAC-Seq) capture mitochondrial RNA and DNA sequences and provide a reliable measurement of mtDNA allelic heteroplasmy in individual cells along with their transcriptional or epigenomic profile. Applicants present several lines of evidence that mitochondrial mutations in human cells can be stably propagated both in vitro and in vivo in physiological settings. Applicants demonstrate that these heteroplasmic mutations can be used to retrospectively infer cell lineages in native contexts and can serve as genetic barcodes to measure clonal dynamics in complex cellular populations. Finally, Applicants show that these mutations are ubiquitous across human tissues, indicating that the approach may be valuable in a variety of systems.

Mitochondrial Genomes

Mitochondria are dynamic organelles that are present in almost all eukaryotic cells and play a crucial role in several cellular pathways (see, e.g., Taanman, Biochimica et Biophysica Acta (BBA)—Bioenergetics, Volume 1410, Issue 2, 9 Feb. 1999, Pages 103-123). The human mitochondrial DNA (mtDNA) is a double-stranded, circular molecule of 16,569 bp and contains 37 genes coding for two rRNAs, 22 tRNAs and 13 polypeptides. These mRNAs are transcribed and then translated within the mitochondrial matrix by a dedicated, unique, and highly specialized machinery. Mitochondrial mRNAs are polyadenylated by a mitochondrial poly(A) polymerase during or immediately after cleavage, whereas the 3'-ends of the two rRNAs are post-transcriptionally modified by the addition of only short adenyl stretches.

Sequencing

In certain embodiments, sequencing comprises high-throughput (formerly "next-generation") technologies to generate sequencing reads. In DNA sequencing, a read is an inferred sequence of base pairs (or base pair probabilities) corresponding to all or part of a single DNA fragment. A typical sequencing experiment involves fragmentation of the genome into millions of molecules or generating complementary DNA (cDNA) fragments, which are size-selected and ligated to adapters. The set of fragments is referred to as a sequencing library, which is sequenced to produce a set of reads. Methods for constructing sequencing libraries are known in the art (see, e.g., Head et al., Library construction for next-generation sequencing: Overviews and challenges. Biotechniques. 2014; 56(2): 61-77). In certain embodiments, the library members (e.g., genomic DNA, cDNA) may include sequencing adaptors that are compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242. 84-9); Shendure et al (Science 2005 309: 1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92.255-64), which are incorporated by reference for the general descriptions of the methods and the particular steps of the methods, including all starting products, reagents, and final products for each of the steps.

In certain embodiments, the present invention includes whole genome sequencing. Whole genome sequencing (also known as WGS, full genome sequencing, complete genome sequencing, or entire genome sequencing) is the process of determining the complete DNA sequence of an organism's genome at a single time. This entails sequencing all of an organism's chromosomal DNA as well as DNA contained in the mitochondria and, for plants, in the chloroplast.

In certain embodiments, the present invention includes whole exome sequencing. Exome sequencing, also known as whole exome sequencing (WES), is a genomic technique for sequencing all of the protein-coding genes in a genome (known as the exome) (see, e.g., Ng et al., 2009, Nature volume 461, pages 272-276). It consists of two steps: the first step is to select only the subset of DNA that encodes proteins. These regions are known as exons—humans have about 180,000 exons, constituting about 1% of the human genome, or approximately 30 million base pairs. The second step is to sequence the exonic DNA using any high-throughput DNA sequencing technology. In certain embodiments, whole exome sequencing is used to determine somatic mutations in genes associated with disease (e.g., cancer mutations).

In certain embodiments, targeted sequencing is used in the present invention (see, e.g., Mantere et al., PLoS Genet 12 e1005816 2016; and Carneiro et al. BMC Genomics, 2012 13:375). Targeted gene sequencing panels are useful tools for analyzing specific mutations in a given sample. Focused panels contain a select set of genes or gene regions that have known or suspected associations with the disease or phenotype under study. In certain embodiments, targeted sequencing is used to detect mutations associated with a disease in a subject in need thereof. Targeted sequencing can increase the cost-effectiveness of variant discovery and detection.

In certain embodiments, the mitochondrial genome is specifically sequenced in a bulk sample using MitoRCA-seq (see e.g., Ni et al., MitoRCA-seq reveals unbalanced cytocine to thymine transition in Polg mutant mice. Sci Rep. 2015 Jul. 27; 5:12049. doi: 10.1038/srep12049). The method employs rolling circle amplification, which enriches the full-length circular mtDNA by either custom mtDNA-specific primers or a commercial kit, and minimizes the contamination of nuclear encoded mitochondrial DNA (Numts). In certain embodiments, RCA-seq is used to detect low-frequency mtDNA point mutations starting with as little as 1 ng of total DNA.

In certain embodiments, single cell Mito-seq (scMito-seq) is used to sequence the mitochondrial genome in single cells. The method is based on performing rolling circle amplification of mitochondrial genomes in single cells.

In certain embodiments, multiple displacement amplification (MDA) is used to generate a sequencing library (e.g., single cell genome sequencing). Multiple displacement amplification (MDA, is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. U.S.A. 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535).

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p 666-673, 2012).

In certain embodiments, the present invention involves single cell RNA sequencing (scRNA-seq). In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves the Assay for Transposase Accessible Chromatin using sequencing (ATAC-seq) as described. (see, e.g., Buenrostro, et al., Transposition of native chromatin for fast and sensitive epigenomic profiling of open chromatin, DNA-binding proteins and nucleosome position. Nature methods 2013; 10 (12): 1213-1218; Buenrostro et al., Single-cell chromatin accessibility reveals principles of regulatory variation. *Nature* 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. *Science*. 2015 May 22; 348(6237): 910-4. doi: 10.1126/science.aab1601. Epub 2015 May 7; US20160208323A1; US20160060691A1; and WO2017156336A1). The term "tagmentation" refers to a step in the Assay for Transposase Accessible Chromatin using sequencing (ATAC-seq) as described. Specifically, a hyperactive Tn5 transposase loaded in vitro with adapters for high-throughput DNA sequencing, can simultaneously fragment and tag a genome with sequencing adapters.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

In certain embodiments, cells to be sequenced according to any of the methods herein are lysed under conditions specific to sequencing mitochondrial genomes. In certain embodiments, lysis using mild conditions does not result in sequencing of all of the mitochondrial genomes. In certain embodiments, use of harsher lysing conditions allows for increase sequencing of mitochondrial genomes due to improved lysis of mitochondria. In certain embodiments, lysis buffers include one or more of NP-40™ detergent, Triton X-100™ detergent, SDS, guanidine isothiocyante, guanidine hydrochloride or guanidine thiocyanate.

In certain embodiments, the sequencing cost is lower in sequencing mitochondrial genomes because of the size of the mitochondrial genome. The terms "depth" or "coverage" as used herein refers to the number of times a nucleotide is read during the sequencing process. In regards to single cell RNA sequencing, "depth" or "coverage" as used herein refers to the number of mapped reads per cell. Depth in regards to genome sequencing may be calculated from the length of the original genome (G), the number of reads (N), and the average read length (L) as N×L/G. For example, a hypothetical genome with 2,000 base pairs reconstructed from 8 reads with an average length of 500 nucleotides will have 2× redundancy.

The terms "low-pass sequencing" or "shallow sequencing" as used herein refers to a wide range of depths greater than or equal to 0.1× up to 1×. Shallow sequencing may also refer to about 5000 reads per cell (e.g., 1,000 to 10,000 reads per cell).

The term "deep sequencing" as used herein indicates that the total number of reads is many times larger than the length of the sequence under study. The term "deep" as used herein refers to a wide range of depths greater than 1× up to 100×. Deep sequencing may also refer to 100× coverage as compared to shallow sequencing (e.g., 100,000 to 1,000,000 reads per cell).

The term "ultra-deep" as used herein refers to higher coverage (>100-fold), which allows for detection of sequence variants in mixed populations.

Selecting Mutations

In certain embodiments, somatic mutations occur over time in long lived organisms. In certain embodiments, somatic mutations occur and are propagated over years. Thus, in preferred embodiments, the subjects according to the present invention include higher eukaryotes (e.g., mammals, humans, livestock, cats, dogs, rodents).

As used herein, the term "homoplasmic" refers to a eukaryotic cell whose copies of mitochondrial DNA are all identical or alleles that are identical in all mitochondria. As used herein, the term "homoplasmic" also refers to identical sequencing reads for a specific genomic region.

In certain embodiments, heteroplasmic mitochondrial mutations are selected and used to cluster single cells. As used herein, the term "heteroplasmic" refers to the presence of more than one type of organellar genome (mitochondrial DNA or plastid DNA) within a cell or individual or mutations only occurring in some copies of mitochondrial DNA. Because most eukaryotic cells contain many hundreds of mitochondria with hundreds of copies of mitochondrial DNA, it is common for mutations to affect only some mitochondria, leaving most unaffected. For example, 5% heteroplasmy refers to a mutation being present in 5% of all mitochondrial genomes. As used herein, "heteroplasmic" also refers to the percentage of mutations in terms of number of reads spanning a specific genomic region. For example, if there are 100 sequencing reads across a region, 5% means that this mutation is in 5 out of 100 reads.

In certain embodiments, mitochondrial mutations used for clustering are selected. In certain embodiments, mutations having a certain heteroplasmy are selected. In certain embodiments, heteroplasmy above a threshold is used because these mutations have a higher probability of being passed onto progeny during multiple generations. In certain embodiments, the mutations are 0.1, 0.25, 0.5, 1, 2, 3, 4, 5, 10, 20 or 25% heteroplasmic.

In certain embodiments, mutations are selected in terms of number of reads spanning a specific genomic region. In certain embodiments, mutations are observed in more than 5 reads. For example, if there is only 1 read with the mutation out of 20 reads spanning this region, this mutation may be eliminated as a low confidence mutation. The low confidence mutations may not be "real". Therefore, in certain embodiments, mutations are selected based on the heteroplasmy in sequencing reads and the number of reads is above a minimum threshold greater than 1 sequencing read having a mutation.

In certain embodiments, heteroplasmy is determined in terms of sequencing reads in all of the single cells analyzed. In certain embodiments, mutations are selected that have greater than 0.5% heteroplasmy. In certain embodiments, mutations are selected based on a conservative threshold and have greater than 5% heteroplasmy.

In certain embodiments, mutations are selected based on mutations detected in mitochondrial genome sequencing reads of a bulk sample obtained from the subject. The bulk sample may be sequenced according to any of the methods for sequencing the mitochondrial genome described above (e.g., DNA-seq, RNA-seq, ATAC-seq or RCA-seq). In certain embodiments, the mitochondrial genome is sequenced directly to determine somatic mutations and not mutations detected due to RNA modifications or reverse transcription errors. In certain embodiments, mutations are selected independently based on detection in the bulk samples and are not further selected based on heteroplasmy. In certain embodiments, the mutations are further selected based on heteroplasmy and mutations are selected from the bulk sample that are greater than 0.5% heteroplasmy. In certain embodiments, the mutations detected in the bulk sample are observed in greater than 1 sequencing read.

In certain embodiments, mutations are selected based on a base quality score. In certain embodiments, the detected mutations have a Phred quality score greater than 20. A Phred quality score is a measure of the quality of the identification of the nucleobases generated by automated DNA sequencing (see, e.g., Ewing et al., (1998). "Base-calling of automated sequencer traces using phred. I. Accuracy assessment". Genome Research. 8 (3): 175-185; and Ewing and Green (1998). "Base-calling of automated sequencer traces using phred. II. Error probabilities". Genome Research. 8 (3): 186-194). It was originally developed for Phred base calling to help in the automation of DNA sequencing in the Human Genome Project. Phred quality scores are assigned to each nucleotide base call in automated sequencer traces. Phred quality scores have become widely accepted to characterize the quality of DNA sequences, and can be used to compare the efficacy of different sequencing methods. Perhaps the most important use of Phred quality scores is the automatic determination of accurate, quality-based consensus sequences.

The method may further comprise excluding RNA modifications, RNA transcription errors and/or RNA sequencing errors from the mutations detected. The RNA modifications may comprise previously identified RNA modifications. These include RNA modifications known in the art and modifications identified by sequencing mitochondrial genomes and comparing the sequences to mitochondrial transcripts. In certain embodiments, RNA modifications, RNA transcription errors and/or RNA sequencing errors are determined by comparing the mutations detected by scRNA-seq to mutations detected by DNA-seq, ATAC-seq or RCA-seq in a bulk sample from the subject.

Determining a Lineage or Clonal Structure

As used herein the terms "lineage" or "clonal structure" refer to the relationship between any two or more cells. As used herein, the term "cell lineage" refers to the developmental path by which a fertilized egg gives rise to the cells of a multicellular organism or the developmental history of a tissue or organ.

As used herein the terms "lineage map" refer to a diagram showing a cell lineage.

As used herein, the term "clone" is a group of cells that share a common ancestry, meaning they are derived from the same cell. In certain embodiments, new mutations arise over time in a clonal population giving rise to sub-clonal populations of cells. As used herein, the term "clonal structure" allows to assess clonal contributions of clones and sub-clones, for example in a tumor. In certain embodiments, the clonal structure is determined before and after a treatment.

In certain embodiments, such as in multicellular organisms, the progeny of single dividing cells cannot be followed and a cell lineage or clonal structure is inferred retrospectively (e.g., after cell division has already occurred). The present invention provides for improved methods of inferring a cell lineage or clonal structure by detecting somatic mutations, specifically somatic mutations that occur in the mitochondrial genome.

Determination of somatic mutations (e.g., including mitochondrial mutations) allows cells derived from a tissue or tumor to be clustered based on the mutations. In certain embodiments, the method further comprises detecting mutations in the nuclear genome and clustering the cells based on the presence of the mitochondrial and nuclear genome mutations in the single cells. In certain embodiments, the method comprises sequencing the nuclear genome in single cells obtained from the subject according to a sequencing method described herein (e.g., whole genome, whole exome sequencing). The clustering provides for related cells.

As used herein, the term "clustering" or "cluster analysis" refers to the task of grouping a set of objects (e.g., cells) in such a way that objects in the same group (called a cluster) are more similar (in some sense) to each other than to those in other groups (clusters). It is a main task of exploratory data mining, and a common technique for statistical data analysis, used in many fields, including machine learning, pattern recognition, image analysis, information retrieval, bioinformatics, data compression, and computer graphics.

Cluster analysis itself is not one specific algorithm, but the general task to be solved. It can be achieved by various algorithms that differ significantly in their understanding of what constitutes a cluster and how to efficiently find them. Popular notions of clusters include groups with small distances between cluster members, dense areas of the data space, intervals or particular statistical distributions. Clustering can therefore be formulated as a multi-objective optimization problem. The appropriate clustering algorithm and parameter settings (including parameters such as the distance function to use, a density threshold or the number of expected clusters) depend on the individual data set and intended use of the results. Cluster analysis as such is not an automatic task, but an iterative process of knowledge discovery or interactive multi-objective optimization that involves trial and failure. It is often necessary to modify data preprocessing and model parameters until the result achieves the desired properties. In certain embodiments, clustering is performed based on somatic mutations present in single cells. In certain embodiments, clustering is performed based on the transcriptomes of single cells.

Clustering can employ different algorithms to generate cluster models. Typical cluster models include:

Connectivity models: for example, hierarchical clustering builds models based on distance connectivity.

Centroid models: for example, the k-means algorithm represents each cluster by a single mean vector.

Distribution models: clusters are modeled using statistical distributions, such as multivariate normal distributions used by the expectation-maximization algorithm.

Density models: for example, DBSCAN and OPTICS defines clusters as connected dense regions in the data space.

Subspace models: in biclustering (also known as co-clustering or two-mode-clustering), clusters are modeled with both cluster members and relevant attributes.

Group models: some algorithms do not provide a refined model for their results and just provide the grouping information.

Graph-based models: a clique, that is, a subset of nodes in a graph such that every two nodes in the subset are connected by an edge can be considered as a prototypical form of cluster. Relaxations of the complete connectivity requirement (a fraction of the edges can be missing) are known as quasi-cliques, as in the HCS clustering algorithm.

Neural models: the most well-known unsupervised neural network is the self-organizing map and these models can usually be characterized as similar to one or more of the above models, and including subspace models when neural networks implement a form of Principal Component Analysis or Independent Component Analysis.

A "clustering" is essentially a set of such clusters, usually containing all objects in the data set. Additionally, it may specify the relationship of the clusters to each other, for example, a hierarchy of clusters embedded in each other. Clusterings can be roughly distinguished as:

Hard clustering: each object belongs to a cluster or not

Soft clustering (also: fuzzy clustering): each object belongs to each cluster to a certain degree (for example, a likelihood of belonging to the cluster)

There are also finer distinctions possible, for example:

Strict partitioning clustering: each object belongs to exactly one cluster

Strict partitioning clustering with outliers: objects can also belong to no cluster, and are considered outliers Overlapping clustering (also: alternative clustering, multi-view clustering): objects may belong to more than one cluster; usually involving hard clusters Hierarchical clustering: objects that belong to a child cluster also belong to the parent cluster Subspace clustering: while an overlapping clustering, within a uniquely defined subspace, clusters are not expected to overlap In certain embodiments, single cells are clustered by hierarchical clustering using somatic mutations.

Cell States

In certain embodiments, the cell states of the clusters are determined. Thus, cell states can be mapped to specific lineage or clonal structures. As used herein, the term "cell state" includes, but is not limited to the gene expression, epigenetic configuration, and/or nuclear structure of single cells. The cell state may be a differentially expressed gene, differentially expressed gene signature, or a differentially accessible chromatin loci.

In certain embodiments, the cell state is determined by analyzing the sequencing data generated for determining somatic mutations (e.g., scRNA-seq, scATAC-seq). Single cell RNA sequencing allows for detecting mitochondrial genome mutations in the transcribed mitochondrial RNA. Mitochondrial RNA is polyadenylated and can be captured by methods that use poly T to reverse transcribe and/or capture mRNA. Single cell ATAC-seq a high-throughput sequencing technique that identifies open chromatin. Depending on the cell type, ATAC-seq samples may contain ~20-80% of mitochondrial sequencing reads and is normally removed as it increases the cost of sequencing. In certain embodiments, single cells are analyzed in separate reaction vessels to preserve the ability to analyze the single cells. Analysis may include proteomic and genomic analysis on the single cells.

In certain embodiments, heritable cell states are identified. Heritable cell states may be cell states that are passed down through a lineage (e.g., specific gene signatures shared by cells in a lineage). In certain embodiments, the establishment of a cell state along a lineage is identified (e.g., when a cell state is established).

Use of Signature Genes

As used herein a "signature" may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any of gene or genes, protein or proteins, or epigenetic element(s) may be substituted. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity or prevalence of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub)population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory the presence of specific cells and cell subtypes are indicative of a particular response to treatment, such as including increased or decreased susceptibility to treatment. The signature may indicate the presence of one particular cell type. In one embodiment, the novel signatures are used to detect multiple cell states or hierarchies that occur in subpopulations of cancer cells that are linked to particular pathological condition (e.g. cancer grade), or linked to a particular outcome or progression of the disease (e.g. metastasis), or linked to a particular response to treatment of the disease.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular tumor cell or tumor cell (sub)population if it is upregulated or only present, detected or detectable in that particular tumor cell or tumor cell (sub)population, or alternatively is downregulated or only absent, or undetectable in that particular tumor cell or tumor cell (sub)population. In this context, a signature consists of one or more differentially expressed genes/proteins or differential epigenetic elements when comparing different cells or cell (sub)populations, including comparing different tumor cells or tumor cell (sub)populations, as well as comparing tumor cells or tumor cell (sub)populations with non-tumor cells or non-tumor cell (sub)populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population level, refer to genes that are differentially expressed in all or substantially all cells of the population (such as at least 80%, preferably at least 90%, such as at least 95% of the individual cells). This allows one to define a particular subpopulation of tumor cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferable is meant induction or alternatively suppression (or upregulation or downregulation) of at least one gene/protein and/or epigenetic element of the signature, such as for instance at least to, at least three, at least four, at least five, at least six, or all genes/proteins and/or epigenetic elements of the signature.

Signatures may be functionally validated as being uniquely associated with a particular immune responder phenotype. Induction or suppression of a particular signature may consequentially be associated with or causally drive a particular immune responder phenotype.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In further aspects, the invention relates to gene signatures, protein signature, and/or other genetic or epigenetic signature of particular tumor cell subpopulations, as defined herein elsewhere. The invention hereto also further relates to particular tumor cell subpopulations, which may be identified based on the methods according to the invention as discussed herein; as well as methods to obtain such cell (sub)populations and screening methods to identify agents capable of inducing or suppressing particular tumor cell (sub)populations.

The invention further relates to various uses of the gene signatures, protein signature, and/or other genetic or epigenetic signature as defined herein, as well as various uses of the tumor cells or tumor cell (sub)populations as defined herein. Particular advantageous uses include methods for identifying agents capable of inducing or suppressing particular tumor cell (sub)populations based on the gene signatures, protein signature, and/or other genetic or epigenetic signature as defined herein. The invention further relates to agents capable of inducing or suppressing particular tumor cell (sub)populations based on the gene signatures, protein signature, and/or other genetic or epigenetic signature as defined herein, as well as their use for modulating, such as inducing or repressing, a particular gene signature, protein signature, and/or other genetic or epigenetic signature. In one embodiment, genes in one population of cells may be activated or suppressed in order to affect the cells of another population. In related aspects, modulating, such as inducing or repressing, a particular a particular gene signature, protein signature, and/or other genetic or epigenetic signature may modify overall tumor composition, such as tumor cell composition, such as tumor cell subpopulation composition or distribution, or functionality.

The signature genes of the present invention may be discovered by analysis of expression profiles of single-cells within a population of cells from freshly isolated tumors, thus allowing the discovery of novel cell subtypes that were previously invisible in a population of cells within a tumor. The presence of subtypes may be determined by subtype specific signature genes. The presence of these specific cell types may be determined by applying the signature genes to bulk sequencing data in a patient tumor. Not being bound by a theory, a tumor is a conglomeration of many cells that make up a tumor microenvironment, whereby the cells communicate and affect each other in specific ways. As such, specific cell types within this microenvironment may express signature genes specific for this microenvironment. Not being bound by a theory the signature genes of the present invention may be microenvironment specific, such as their expression in a tumor. Not being bound by a theory, signature genes determined in single cells that originated in a tumor are specific to other tumors. Not being bound by a theory, a combination of cell subtypes in a tumor may indicate an outcome. Not being bound by a theory, the signature genes can be used to deconvolute the network of cells present in a tumor based on comparing them to data from bulk analysis of a tumor sample. Not being bound by a theory the presence of specific cells and cell subtypes may be indicative of tumor growth, invasiveness and resistance to treatment. The signature gene may indicate the presence of one particular cell type. In one embodiment, the signature genes may indicate that tumor infiltrating T-cells are present. The presence of cell types within a tumor may indicate that the tumor will be resistant to a treatment. In one embodiment, the signature genes of the present invention are applied to bulk sequencing data from a tumor sample obtained from a subject, such that information relating to disease outcome and personalized treatments is determined. In one embodiment, the novel signature genes are used to detect multiple cell states that occur in a subpopulation of tumor cells that are linked to resistance to targeted therapies and progressive tumor growth.

In one embodiment, the signature genes are detected by immunofluorescence, immunohistochemistry, fluorescence activated cell sorting (FACS), mass cytometry (CyTOF), Drop-seq, RNA-seq, scRNA-seq, InDrop, single cell qPCR, MERFISH (multiplex (in situ) RNA FISH) and/or by in situ hybridization. Other methods including absorbance assays and colorimetric assays are known in the art and may be used herein.

In one embodiment, tumor cells are stained for sub-clonal cell type specific signature genes. In one embodiment, the cells are fixed. In another embodiment, the cells are formalin fixed and paraffin embedded. Not being bound by a theory, the presence of the cell subtypes in a tumor indicate outcome and personalized treatments. Not being bound by a theory, the cell subtypes may be quantitated in a section of a tumor and the number of cells indicates an outcome and personalized treatment.

Lineages and Clonal Populations in Tissues

In certain embodiments, the single cells comprise related cell types. The related cell types may be from a tissue. In certain embodiments, lineage or clonal structures are determined for specific tissues. The tissue may be associated with a disease state. The disease may be a degenerative disease. The tissue may be healthy tissue. Thus, healthy tissue may be studied to understand a disease state. The tissue may be diseased tissue. Thus, diseased tissue may be studied to understand a disease state.

the present invention provides for a method of identifying changes in clonal populations having a cell state between healthy and diseased tissue comprising determining clonal populations of cells having a cell state in healthy and diseased cells according to claim 1 and comparing the clonal populations. Thus, clonal populations are determined in healthy and diseased tissues. The cell states in the clonal populations can be determined. The tissues may be obtained from the same subject. The cell states are then determined for the clonal populations. Clonal populations shared between the diseased and healthy tissues, as well as clonal populations differentially present or absent between the diseased and healthy tissues can be determined. The present invention allows for improved determination of clonal populations and thus can provide for novel therapeutic targets present in specific populations.

The disease may be selected from the group consisting of autoimmune disease, bone marrow failure, hematological conditions, aplastic anemia, beta-thalassemia, diabetes, motor neuron disease, Parkinson's disease, spinal cord injury, muscular dystrophy, kidney disease, liver disease, multiple sclerosis, congestive heart failure, head trauma, lung disease, psoriasis, liver cirrhosis, vision loss, cystic fibrosis, hepatitis C virus, human immunodeficiency virus, inflammatory bowel disease (IBD), and any disorder associated with tissue degeneration.

As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body.

Non-limiting examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behçet's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myoxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

In certain embodiments, tissue specific mitochondrial mutations are determined for a subject. The tissue specific mitochondrial mutations may be used to better characterize tissues in healthy tissues and diseased tissue. In certain embodiments, tissue specific mutations may be used to determine the cell origin of metastatic cancer of unknown primary origin.

Clonal Populations in Tumors

In another aspect, the present invention provides for a method of detecting clonal populations of cells in a tumor sample obtained from a subject in need thereof. In certain embodiments, clonal populations of cells are identified based on the presence of the mitochondrial mutations and somatic mutations associated with the cancer in the single cells.

Somatic mutations associated with cancer may include mutations associated with prognosis, treatment or resistance to treatment. Mutations associated across the spectrum of human cancer types have been identified (e.g., Hodis E. et al., Cell. (2012) Jul. 20; 150(2):251-63; and Vogelstein, et al., Science (2013) Mar. 29: Vol. 339, Issue 6127, pp. 1546-1558). A directory of cancer mutations, including gene specific mutations may be found at cancer.sanger.ac.uk/cosmic, the Catalogue of Somatic Mutations in Cancer (COSMIC) (Forbes, et al.; COSMIC: somatic cancer genetics at high-resolution. Nucleic Acids Res 2017; 45 (Dl): D777-D783. doi: 10.1093/nar/gkw1121) and www.mycancergenome.org. In certain embodiments, any of these known mutations may be detected depending on the cancer type.

The tumor sample may be obtained before a cancer treatment. The method may further comprise obtaining a sample after treatment and comparing the presence of clonal populations before and after treatment, wherein clonal populations of cells sensitive and resistant to the treatment are identified. The method may comprise determining mutations and subclonal populations on at least one time point after administration of the therapy. The at least one time point may be a week, a month, a year, two years, three years, or five years after initiation of a therapy. The time point may be after a relapse in the disease is detected. Relapse may be any recurrence of symptoms of a disease after a period of improvement. Time points may be taken at any point after the initial treatment of the disease and includes time points following a change to the treatment or after the treatment has been completed.

The cancer treatment may be selected from the group consisting of chemotherapy, radiation therapy, immunotherapy, targeted therapy and a combination thereof.

The therapeutic agent is for example, a chemotherapeutic or biotherapeutic agent, radiation, or immunotherapy. Any suitable therapeutic treatment for a particular cancer may be administered. Examples of chemotherapeutic and biotherapeutic agents include, but are not limited to an angiogenesis inhibitor, such as angiostatin Kl-3, DL-a-Difluoromethylornithine, endostatin, fumagillin, genistein, minocycline, staurosporine, and thalidomide; a DNA intercalator/crosslinker, such as Bleomycin, Carboplatin, Carmustine, Chlorambucil, Cyclophosphamide, cis-Diammineplatinum (II) dichloride (Cisplatin), Melphalan, Mitoxantrone, and Oxaliplatin; a DNA synthesis inhibitor, such as (±)-Amethopterin (Methotrexate), 3-Amino-1,2,4-benzotriazine 1,4-di oxide, Aminopterin, Cytosine β-D-arabinofuranoside, 5-Fluoro-5'-deoxyuridine, 5-Fluorouracil, Ganciclovir, Hydroxyurea, and Mitomycin C; a DNA-RNA transcription regulator, such as Actinomycin D, Daunorubicin, Doxorubicin, Homoharringtonine, and Idarubicin; an enzyme inhibitor, such as S(+)-Camptothecin, Curcumin, (−)-Deguelin, 5,6-Dichlorobenzimidazole 1-β-D-ribofuranoside, Etoposide, Formestane, Fostriecin, Hispidin, 2-Imino-1-imidazoli-dineacetic acid (Cyclocreatine), Mevinolin, Trichostatin A, Tyrphostin AG 34, and Tyrphostin AG 879; a gene regulator, such as 5-Aza-2'-deoxycytidine, 5-Azacytidine, Cholecalciferol (Vitamin D3), 4-Hydroxytamoxifen, Melatonin, Mifepristone, Raloxifene, all trans-Retinal (Vitamin A aldehyde), Retinoic acid, all trans (Vitamin A acid), 9-cis-Retinoic Acid, 13-cis-Retinoic acid, Retinol (Vitamin A), Tamoxifen, and Troglitazone; a microtubule inhibitor, such as Colchicine, docetaxel, Dolastatin 15, Nocodazole, Paclitaxel, Podophyllotoxin, Rhizoxin, Vinblastine, Vincristine, Vindesine, and Vinorelbine (Navelbine); and an unclassified antitumor agent, such as 17-(Allylamino)-17-demethoxygeldanamycin, 4-Amino-1,8-naphthalimide, Apigenin, Brefeldin A, Cimetidine, Dichloromethylene-diphosphonic acid, Leuprolide (Leuprorelin), Luteinizing Hormone-Releasing Hormone, Pifithrin-a, Rapamycin, Sex hormone-binding globulin, Thapsigargin, Vismodegib (Erivedge™), and Urinary trypsin inhibitor fragment (Bikunin). The antitumor agent may be a monoclonal antibody or antibody drug conjugate, such as rituximab (Rituxan®), alemtuzumab (Campath®), Ipilimumab (Yervoy®), Bevacizumab (Avastin®), Cetuximab (Erbitux®), panitumumab (Vectibix®), and trastuzumab (Herceptin®), Tositumomab and 1311-tositumomab (Bexxar®), ibritumomab tiuxetan (Zevalin®), brentuximab vedotin (Adcetris®), siltuximab (Sylvant™), pembrolizumab (Keytruda®), ofatumumab (Arzerra®), obinutuzumab (Gazyva™), 90Y-ibritumomab tiuxetan, 1311-tositumomab, pertuzumab (Perjeta™), ado-trastuzumab emtansine (Kadcyla™), Denosumab (Xgeva®), and Ramucirumab (Cyramza™). The antitumor agent may be a small molecule kinase inhibitor, such as Vemurafenib (Zelboraf®), imatinib mesylate (Gleevec®), erlotinib (Tarceva®), gefitinib (Iressa®), lapatinib (Tykerb®), regorafenib (Stivarga®), sunitinib (Sutent®), sorafenib (Nexavar®), pazopanib (Votrient®), axitinib (Inlyta®), dasatinib (Sprycel®), nilotinib (Tasigna®), bosutinib (Bosulif®), ibrutinib (Imbruvica™), idelalisib (Zydelig®), crizotinib (Xalkori®), afatinib dimaleate (Gilotrif®), ceritinib (LDK378/Zykadia), trametinib (Mekinist®), dabrafenib (Tafinlar®), Cabozantinib (Cometriq™), vandetanib (Caprelsa®), The antitumor agent may be a proteosome inhibitor, such as bortezomib (Velcade®) and carfilzomib (Kyprolis®). The antitumor agent may be a cytokine such as interferons (INFs), interleukins (ILs), or hematopoietic growth factors. The antitumor agent may be INF-a, IL-2, Aldesleukin IL-2, Erythropoietin, Granulocyte-macrophage colony-stimulating factor (GM-CSF) or granulocyte colony-stimulating factor. The antitumor agent may be a targeted therapy such as toremifene (Fareston®), fulvestrant (Faslodex®), anastrozole (Arimidex®), exemestane (Aromasin®), letrozole (Femara®), ziv-aflibercept (Zaltrap®), Alitretinoin (Panretin®), temsirolimus (Torisel®), Tretinoin (Vesanoid®), denileukin diftitox (Ontak®), vorinostat (Zolinza®), romidepsin (Istodax®), bexarotene (Targretin®), pralatrexate (Folotyn®), lenaliomide (Revlimid®), belinostat (Beleodaq™), lenaliomide (Revlimid®), pomalidomide (Pomalyst®), Cabazitaxel (Jevtana®), enzalutamide (Xtandi®), abiraterone acetate (Zytiga®), radium 223 chloride (Xofigo®), or everolimus (Afinitor®). The antitumor agent may be a checkpoint inhibitor such as an inhibitor of the programmed death-1 (PD-1) pathway, for example an anti-PDI antibody (Nivolumab). The inhibitor may be an anti-cytotoxic T-lymphocyte-associated antigen (CTLA-4) antibody. The inhibitor may target another member of the CD28 CTLA4 Ig superfamily such as BTLA, LAG3, ICOS, PDL1 or KIR. A checkpoint inhibitor may target a member of the TNFR superfamily such as CD40, OX40, CD 137, GITR, CD27 or TIM-3. Additionally, the antitumor agent may be an epigenetic targeted drug such as HDAC inhibitors, kinase inhibitors, DNA methyltransferase inhibitors, histone demethylase inhibitors, or histone methylation inhibitors. The epigenetic drugs may be Azacitidine (Vidaza), Decitabine (Dacogen), Vorinostat (Zolinza), Romidepsin (Istodax), or Ruxolitinib (Jakafi).

The immunotherapy may be adoptive cell transfer therapy. As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis. Additionally, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

The immunotherapy may be an inhibitor of check point protein. Specific check point inhibitors include, but are not limited to anti-CTLA4 antibodies (e.g., Ipilimumab), anti-PD-1 antibodies (e.g., Nivolumab, Pembrolizumab), and anti-PD-L1 antibodies (e.g., Atezolizumab).

Screening

In another aspect, the present invention provides for a method of identifying a cancer therapeutic target. In certain embodiments, clonal populations of cells in a tumor sample are detected. Differential cell states may be identified (e.g., transcriptional or chromatin) between the clonal populations. Cell states present in resistant clonal populations as determined by determining clonal populations after treatment, preferably before and after treatment. The cell states identified between clonal populations can be used to identify a therapeutic target. The cell state may be a differentially expressed gene, differentially expressed gene signature, or a differentially accessible chromatin loci. The current method provides for improved determination of clonal populations of cells, thus differential expression or cell states between clonal populations can be determined. Previous methods may not identify a therapeutic target.

In another aspect, the present invention provides for a method of screening for a cancer treatment. A tumor sample may be obtained from a subject in need thereof. The tumor sample may be grown ex vivo. The tumor sample may be used to generate a patient derived xenograft. Patient derived xenografts (PDX) are models of cancer, where tissue or cells from a patient's tumor are implanted into an immunodeficient mouse. PDX models are used to create an environment that resembles the natural growth of cancer, for the study of cancer progression and treatment. Humanized-xenograft models are created by co-engrafting the patient tumor fragment and peripheral blood or bone marrow cells into a NOD/SCID mouse (Siolas D, Hannon G J (September 2013). "Patient-derived tumor xenografts: transforming clinical samples into mouse models". Cancer Research (Perspective). 73 (17): 5315-9). The co-engraftment allows for reconstitution of the murine immune system enabling researchers to study the interactions between xenogenic human stroma and tumor environments in cancer progression and metastasis (Talmadge J E, Singh R K, Fidler I J, Raz A (March 2007). "Murine models to evaluate novel and conventional therapeutic strategies for cancer". The American Journal of Pathology (Review). 170 (3): 793-804). Clonal populations may be detected in the tumor sample. The tumor sample or mouse model can be treated according to the standard of care for the cancer (e.g., targeting BCR-ABL in CML). The effect of the treatment on the clonal populations can be determined. In one embodiment, it can be determined that the treatment will be effective for the subject's tumor. The effect of the treatment on the clonal populations can be determined and differentially expressed genes between resistant and sensitive clonal populations can be used to determine therapeutic targets. Determining the effects on clonal populations may be determined by measuring expression of a gene signature associated with the clonal populations.

In certain embodiments, tumor clonal structures are measured, cancer therapeutic targets are identified, and/or therapeutics are screened for a specific cancer. The cancer may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

The cancer may include, without limitation, solid tumors such as sarcomas and carcinomas. Examples of solid tumors include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, epithelial carcinoma, bronchogenic carcinoma, hepatoma, colorectal cancer (e.g., colon cancer, rectal cancer), anal cancer, pancreatic cancer (e.g., pancreatic adenocarcinoma, islet cell carcinoma, neuroendocrine tumors), breast cancer (e.g., ductal carcinoma, lobular carcinoma, inflammatory breast cancer, clear cell carcinoma, mucinous carcinoma), ovarian carcinoma (e.g., ovarian epithelial carcinoma or surface epithelial-stromal tumour including serous tumour, endometrioid tumor and mucinous cystadenocarcinoma, sex-cord-stromal tumor), prostate cancer, liver and bile duct carcinoma (e.g., hepatocelluar carcinoma, cholangiocarcinoma, hemangioma), choriocarcinoma, seminoma, embryonal carcinoma, kidney cancer (e.g., renal cell carcinoma, clear cell carcinoma, Wilm's tumor, nephroblastoma), cervical cancer, uterine cancer (e.g., endometrial adenocarcinoma, uterine papillary serous carcinoma, uterine clear-cell carcinoma, uterine sarcomas and leiomyosarcomas, mixed mullerian tumors), testicular cancer, germ cell tumor, lung cancer (e.g., lung adenocarcinoma, squamous cell carcinoma, large cell carcinoma, bronchioloalveolar carcinoma, non-small-cell carcinoma, small cell carcinoma, mesothelioma), bladder carcinoma, signet ring cell carcinoma, cancer of the head and neck (e.g., squamous cell carcinomas), esophageal carcinoma (e.g., esophageal adenocarcinoma), tumors of the brain (e.g., glioma, glioblastoma, medullablastoma, astrocytoma, medulloblastoma, craniopharyngioma, ependymoma, pinealoma, hemangioblastoma, acoustic neuroma, oligodenroglioma, schwannoma, meningioma), neuroblastoma, retinoblastoma, neuroendocrine tumor, melanoma, cancer of the stomach (e.g., stomach adenocarcinoma, gastrointestinal stromal tumor), or carcinoids. Lymphoproliferative disorders are also considered to be proliferative diseases.

Selecting Cell Types

In certain embodiments, the cells obtained from a subject are selected for a cell type. In certain embodiments, stem and progenitor cells are selected. In certain embodiments, progenitor cells specific for generating a specific tissue are identified. In certain embodiments, cells along a lineage specific for generating a specific tissue are identified. In certain embodiments, CD34+ hematopoietic stem and progenitor cells may be selected (e.g., to study blood diseases).

In certain embodiments, the method further comprises determining a lineage and/or clonal structure for single cells from two or more tissues and identifying tissue specific mitochondrial mutations for the subject. In certain embodiments, the related cell types are from a tumor sample. In certain embodiments, peripheral blood mononuclear cells (PBMCs) and/or bone marrow mononuclear cells (BMMCs) are selected. The PBMCs and/or BMMCs may be selected before and after stem cell transplantation in a subject.

In certain embodiments, lineages or clonal structures for populations of immune cells may be determined (e.g., T cells specific for an antigen).

The term "immune cell" generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Thαβ, CD4+, CD8+, effector Th, memory Th, regulatory Th, CD4+/CD8+ thymocytes, CD4−/CD8− thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2, B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

The present invention provides a novel analytic framework, methods and systems that are widely applicable across diseases, and specifically different types of cancer. The present invention provides for the detection and grouping of subclonal populations of cells or disease causing entities based upon mitochondrial mutations present in each cell or disease causing entity. The subclones may be present in less than 10%, less than 5%, less than 1%, less than 0.1%, less than 0.01%, less than 0.001% or less than 0.0001% of the diseased cells or malignant cells. The disease can be any disease where drug resistance mutations occur or where clonal evolution occurs.

In one aspect, the present invention provides a method of individualized or personalized treatment for a disease undergoing clonal evolution and for preventing relapse after treatment in a patient in need thereof comprising: determining mutations present in a disease cell fraction from the patient before and/or after administration of a therapy; determining subclonal populations within the disease cell fraction, selecting at least one subclonal population to treat.

The invention is further described in the following examples, which do not limit the scope of the invention described in the claims.

EXAMPLES

Example 1—Sequence Variation in Human mtDNA

Human mtDNA sequence variation has several promising attributes for its utility in lineage tracing. First, the human mitochondrial genome is 16,571 bp long, providing a substantial target for genetic diversity to serve as a natural barcode, while being sufficiently small to allow cost-effective and complete sequencing. Second, the reported mutation rate for mtDNA is 10- to 100-fold higher than for nuclear genomic DNA. Third, these mutations often reach high levels of heteroplasmy or even homoplasmy, due to a combination of vegetative segregation, random genetic drift, and relaxed replication (24, 25). Finally, the relatively high mitochondrial copy number per cell (100 s-1,000 s; compared to two copies of nuclear DNA), should readily facilitate confident detection of higher frequency heteroplasmic mutations in individual cells (FIG. 1A) (26). Thus, Applicants hypothesized that examining mitochondrial mutations may enable faithful reconstruction of cell lineages.

Example 2—mtDNA Based Genotyping with ATAC-Seq Enables Lineage Tracing

Figure 1B:
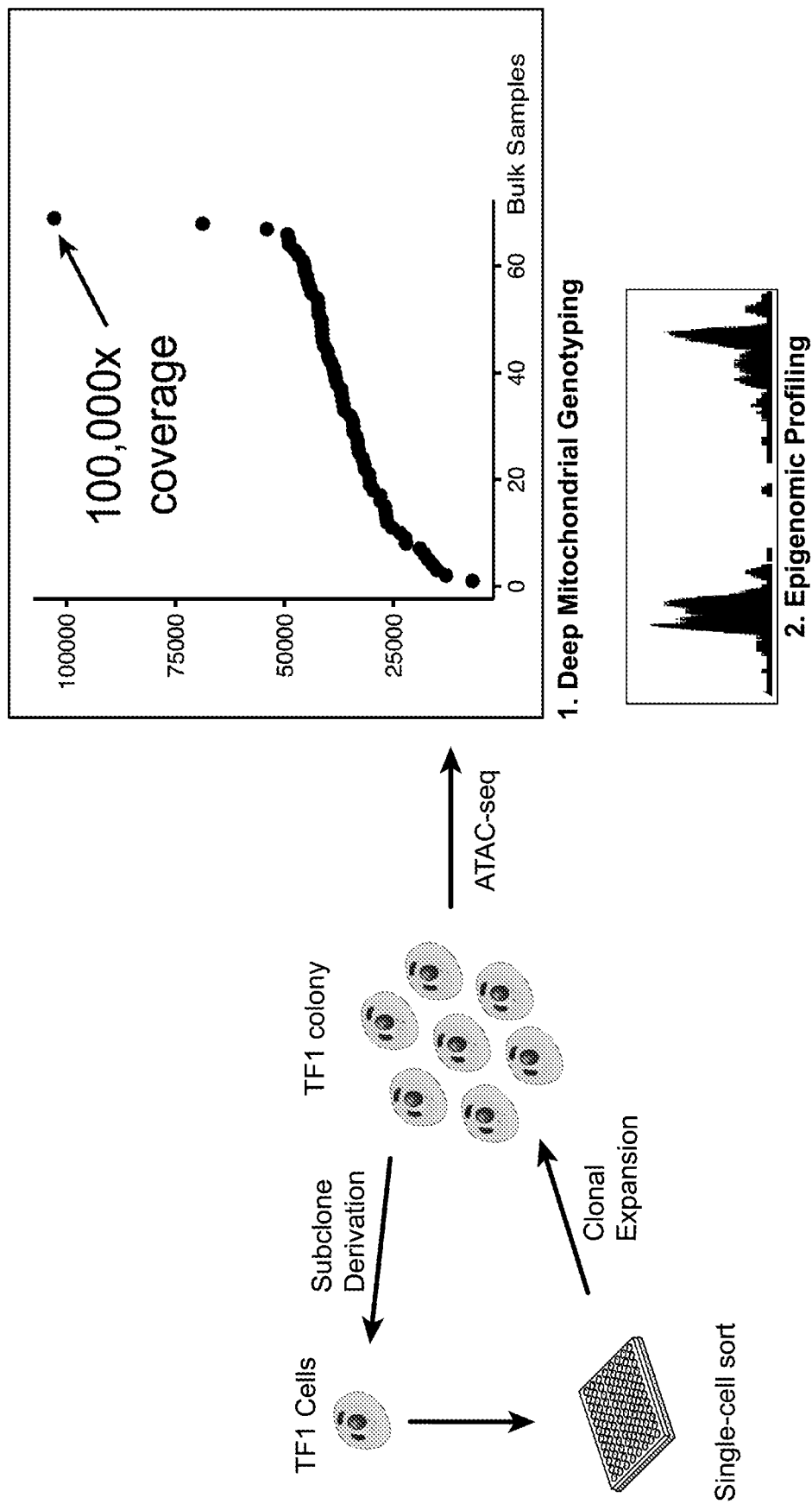
Figure 1C:
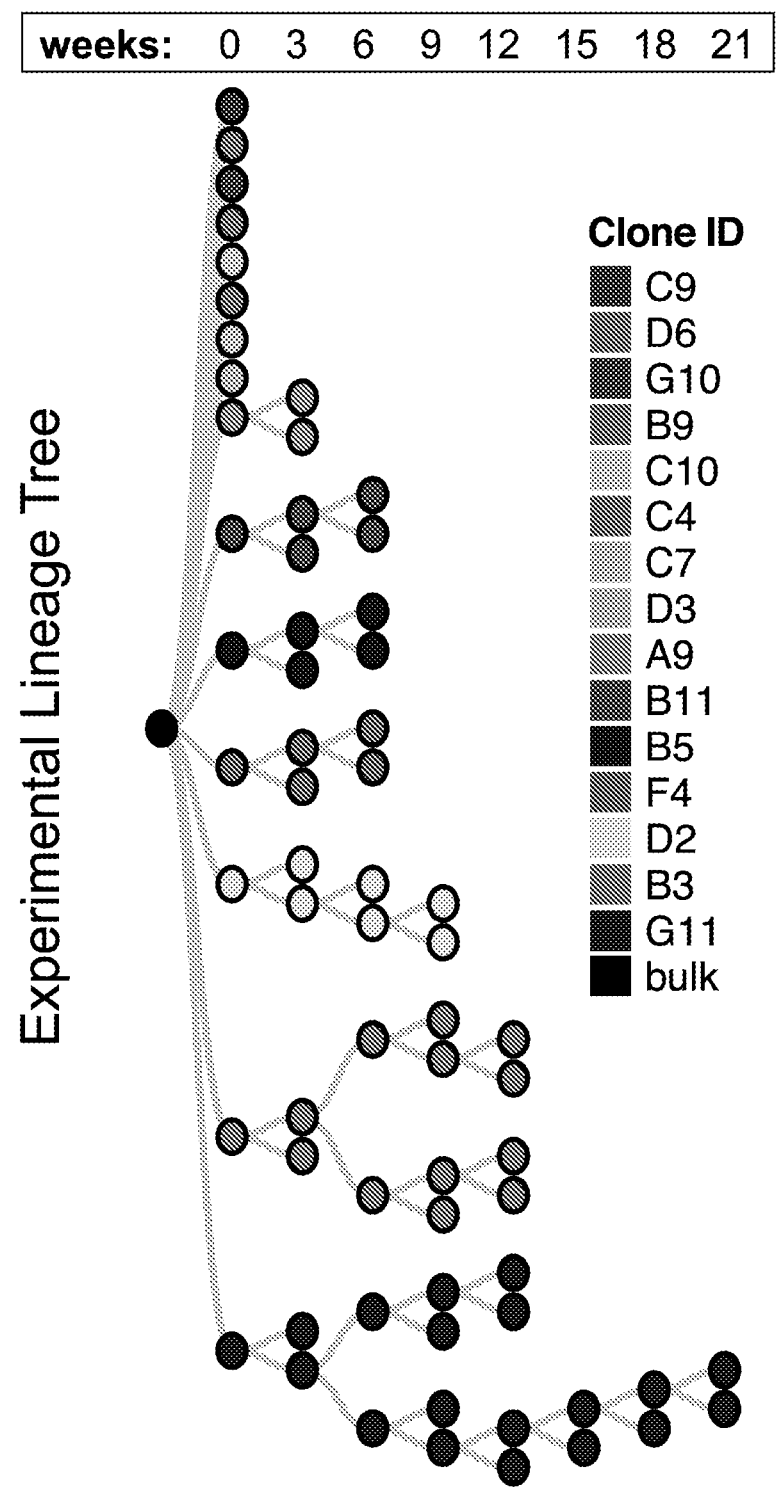

Applicants conducted a proof of principle experiment, where Applicants derived and propagated clonal populations from the hematopoietic TF1 cell line (FIG. 1B). Applicants generated a "ground truth" experimental phylogenetic tree of 65 individual (sub-) clonal populations up to 8 generations (generation time ~3 weeks between two consecutive bottlenecks) (FIG. 1C). For each generation Applicants isolated single cells from the parental colony, and expanded each clone to derive sub-clones in an iterative process. The original population and each expanded sub-clone were profiled by ATAC-seq, which is known to capture the full mitochondrial genome as an unwanted by-product (27) (FIG. 7A, table S1). On average, each of the 16,571 mtDNA basepairs was covered at 3,380-fold per million mapped reads, indicating the potential for low cost lineage tracing using mtDNA mutations. Applicants determined high-confidence heteroplasmic mitochondrial genotypes with a computational variant-calling pipeline Applicants developed that utilizes individual per-base, per-allele quality scores (BQ) and verified that the calls were reproducible across sequencing runs (FIG. 7B,C; SOM).

Figure 1D:
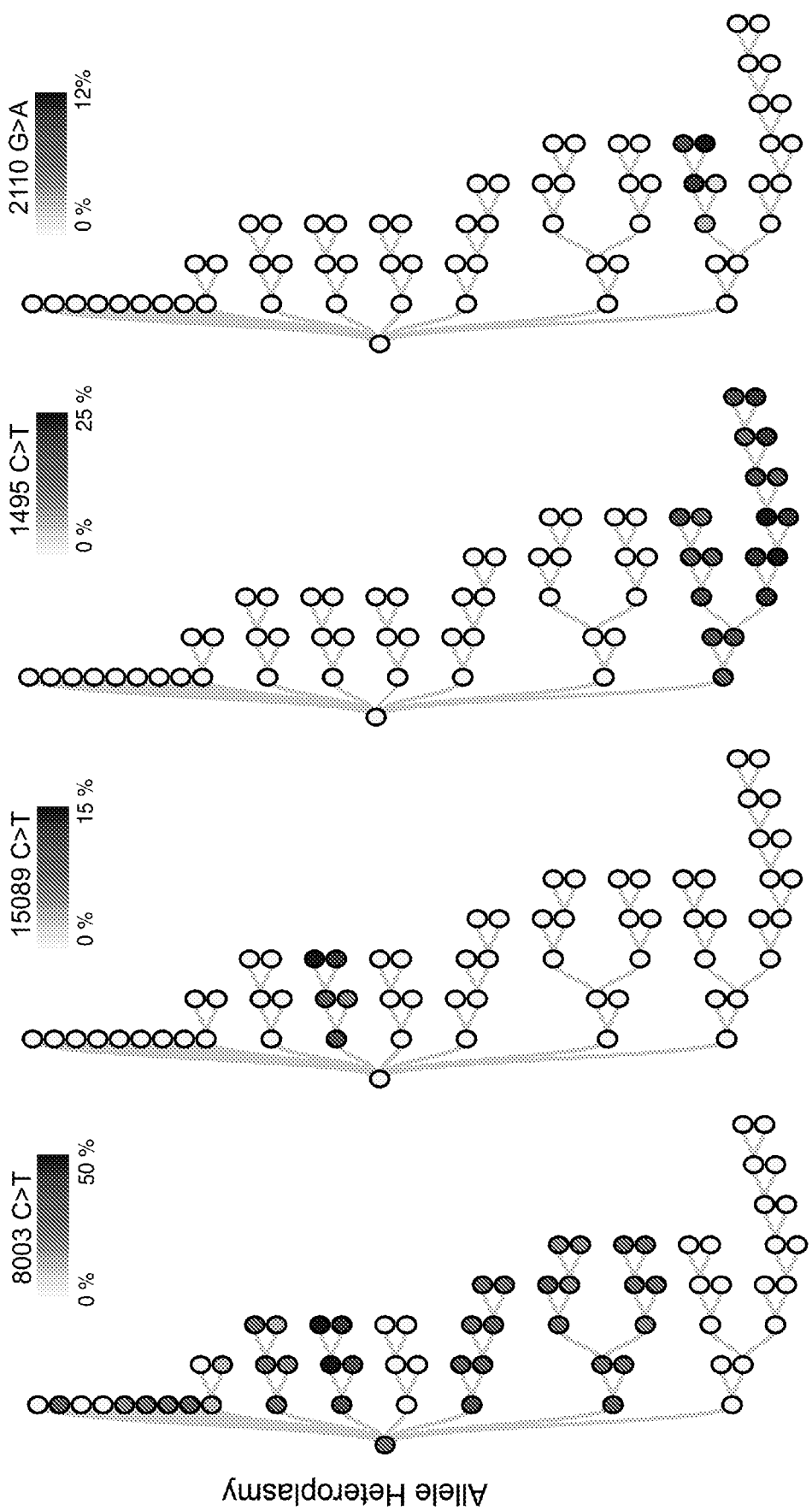
Figure 1I:
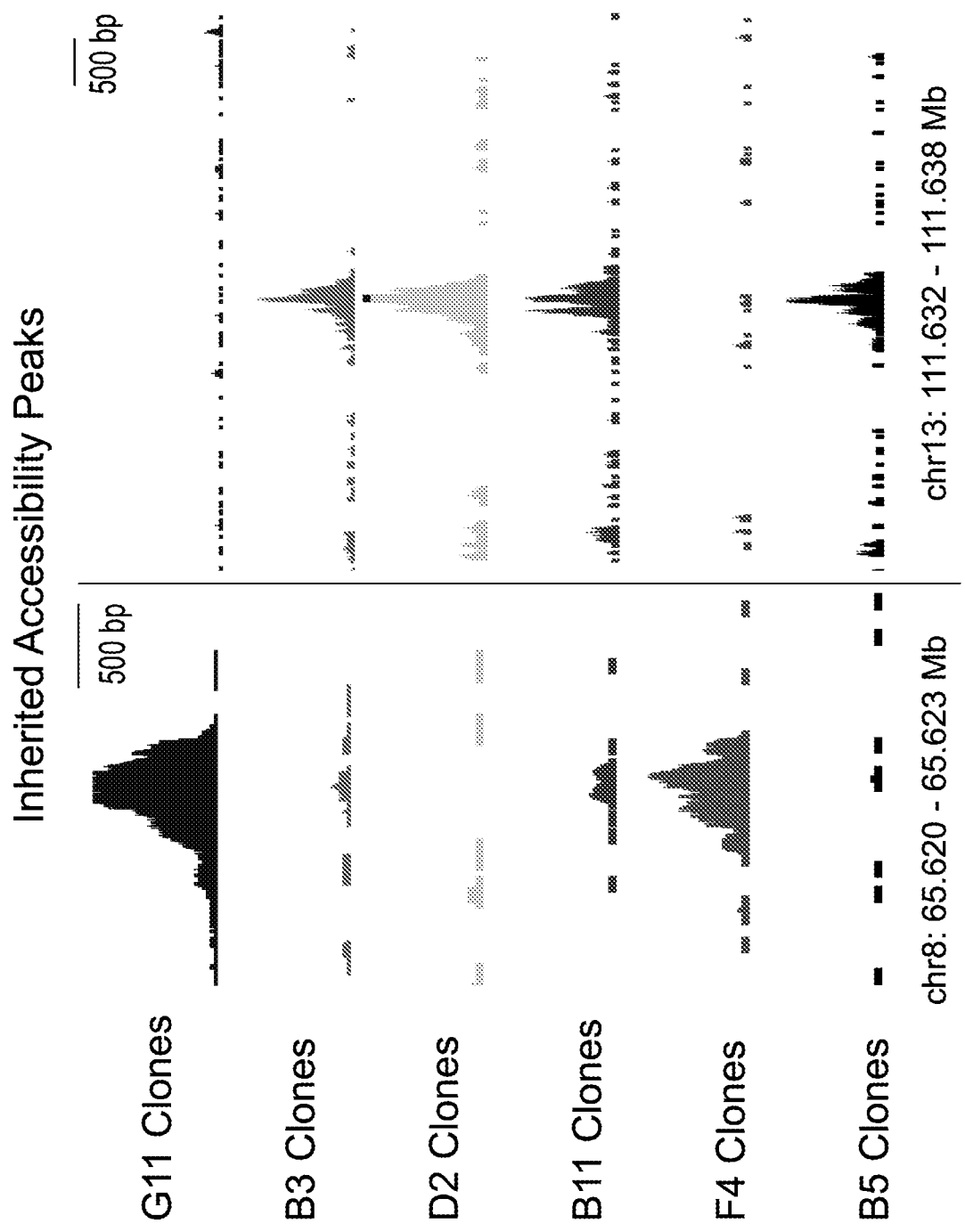
Figures 7F, 7G:
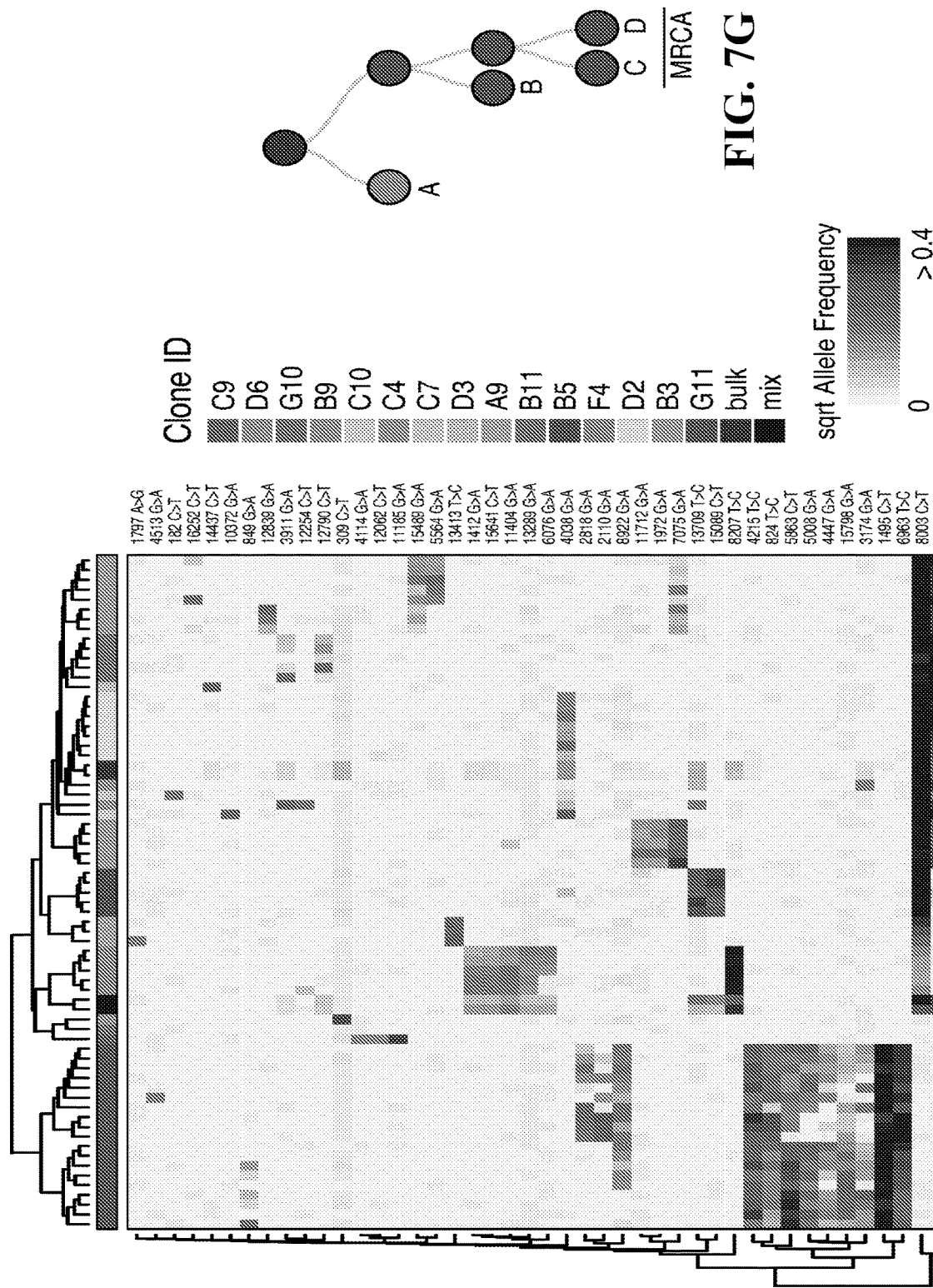
FIG. 7—(A) Distribution of mitochondrial coverage per million reads for each bulk ATAC-seq sample; color indicates the parent clone. (B) mtDNA mutations can be consistently detected across replicate sequencing runs. (C) Gaussian mixture model fit over per-base pair, per-allele base qualities. The dotted line indicates the threshold for 99% probability of belonging to the blue distribution, indicating a high-quality variant. (D) Summary of variance component model for structure determined by mitochondrial genotypes (red) and the clone ID (black). Each point represents one accessibility peak ranked in terms of variance explained by the sample structure. (E) Results of deconvoluting synthetic samples. The experimental proportions were determined based on varying concentrations of second-generation clones before ATAC-seq processing whereas the inferred is based on a computational model. (F) Heatmap with hierarchical clustering of the bulk TF1 clonal families and called high-confidence variants. (G) Schematic of most recent common ancestor (MRCA) analysis to quantify lineage reconstruction accuracy. Here, trios are analyzed to determine the pair that has the MCRA, including between-clone example (A,C,D) and a within-clone example (B,C,D).

Applicants detected a large breadth of mutations including robust, clone- and sub-clone-specific mutations that were propagated through its progeny and in subsequent sub-clones once they arose (FIG. 7F). Most mutations were C>T transitions, consistent with previous reports (28-30). Although some somatic mutations were shared amongst multiple first generation clones and their progeny (e.g., 8003 C>T, FIG. 1D, left), nearly all progeny of one clone shared mutations that were unique to that clone, but not to other independently derived clones, and were stably propagated over the course of the experiment (e.g., 15089 C>T, 1495 C>T, FIG. 1D, two middle panels, FIG. 7F). These results are consistent with previous in vivo and in vitro studies that observed stable levels of heteroplasmic variants over long time periods (24). Furthermore, Applicants could detect new somatic mutations (2110 G>A) that arose within sub-clones (FIG. 1D, right, FIG. 7F).

The high-confidence mutations allowed us to reconstruct the clonal family structure with high accuracy (FIG. 1E,F). To achieve this, Applicants performed an ordinal hierarchical clustering on individual samples, resulting in near-perfect clustering of all (sub-)clones belonging to a single clonal family (FIG. 1C,E), Specifically, Applicants note accuracies of identifying the most recent common ancestor (MRCA) at 95% between first-generation clones and 68% within sub-clones derived from first-generation clones (FIG. 1F, FIG. 7G; SOM). Moreover, Applicants could infer clonal contributions to heterogeneous bulk populations using mitochondrial variation. In particular, Applicants experimentally mixed 3 clones at various concentrations, performed ATAC-seq, calculated allelic heteroplasmy, and robustly deconvolved the clonal contributions computationally (FIG. 7E; SOM). Thus, the proof of principle demonstrates that mitochondrial mutations can be used to retrospectively infer cellular lineage.

Notably, the approach pairs mitochondrial genotypes with chromatin state information for each clone. To identify differences in chromatin state that follow inferred relationships, Applicants approximated the pairwise colony-colony mitochondrial relatedness (FIG. 1G; SOM) and performed a random effects variance decomposition of each chromatin accessibility peak in the TF1 clones (FIG. 1H), asking how "heritable" a chromatin feature is in a population. Of 91,607 peaks tested, 8,570 peaks were highly heritable (>90% variance explained; FIG. 1H, FIG. 7D). Taken together, the proof-of-principle experiments demonstrate the utility of mtDNA genotyping for cellular lineage tracing and the integration of cell state data for paired inference.

Example 3—Detection of Heteroplasmy Using Single Cell Genomics

To determine the utility of lineage tracing using mtDNA at single-cell resolution, Applicants next systematically investigated the ability of prevalent methods for either scRNA- or scATAC-seq to identify mitochondrial genotypes. Because the human mitochondrial genome is completely transcribed (FIG. 2E), Applicants hypothesized that heteroplasmic mitochondrial mutations might be detected by scRNA-seq, as demonstrated for other transcribed sequences (31, 32). Indeed, full length scRNA-seq methods showed much more extensive coverage of the mtDNA genome than 3' end directed scRNA-seq (FIG. 2A, FIG. 8A,B), when comparing six scRNA-seq protocols, all applied to mouse embryonic stem cells (mESCs) (33). Moreover, there was a high concordance between heteroplasmic allele frequency estimates from scRNA-seq and single cell whole genome DNA-seq from the same cell (34) (FIG. 2B). Interestingly, several highly heteroplasmic mutations were specific to RNA: some may be real RNA-editing events, including one that has been previously validated (2619 A>G) (35), but many are observed at low frequencies (<20%) and reflect either RNA transcription errors or technical errors in scRNA-seq, as previously reported (31, 32).

Figure 2A:
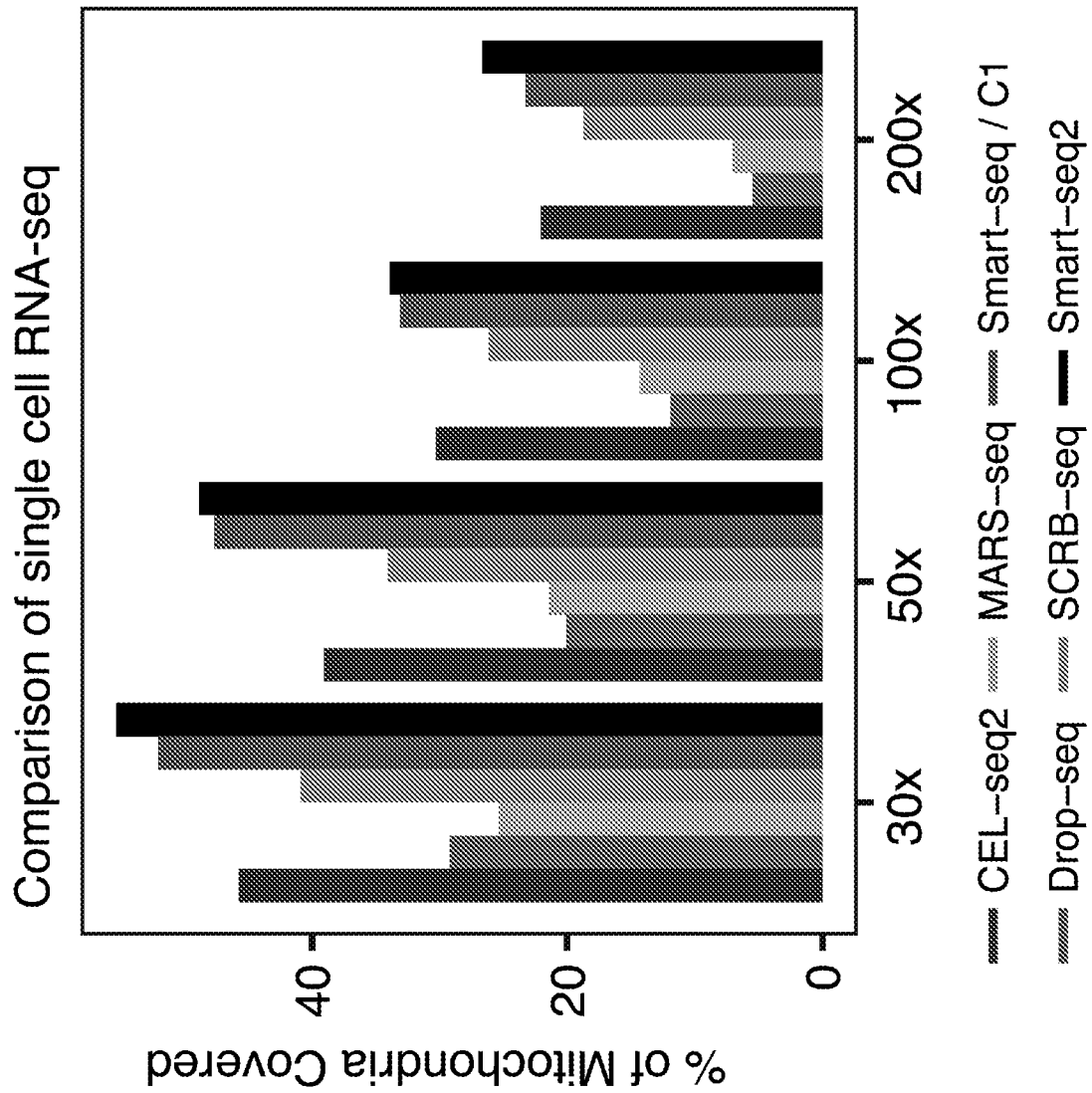
FIG. 2—Mitochondrial mutations are reliably detected using contemporary single-cell assays. (A) Comparison of 6 scRNA-seq technologies and their coverage across the mouse mitochondrial genome. (B) Comparison of allelic heteroplasmy from mtDNA and mRNA derived from the same single cells. (C) Bulk and single-cell data collected for three TF1 clones. (D) Comparison of allele frequencies derived from bulk ATAC- and bulk RNA-seq from TF1 clones. (E) Comparison of mitochondrial coverage across all samples for TF clone G10. For the single cell assays, coverage represents the sum of single cells. (F) Examples of four clone-specific mutations that are reliably detected by various single-cell assays with heteroplasmies as low as 3.8%.
Figure 2B:
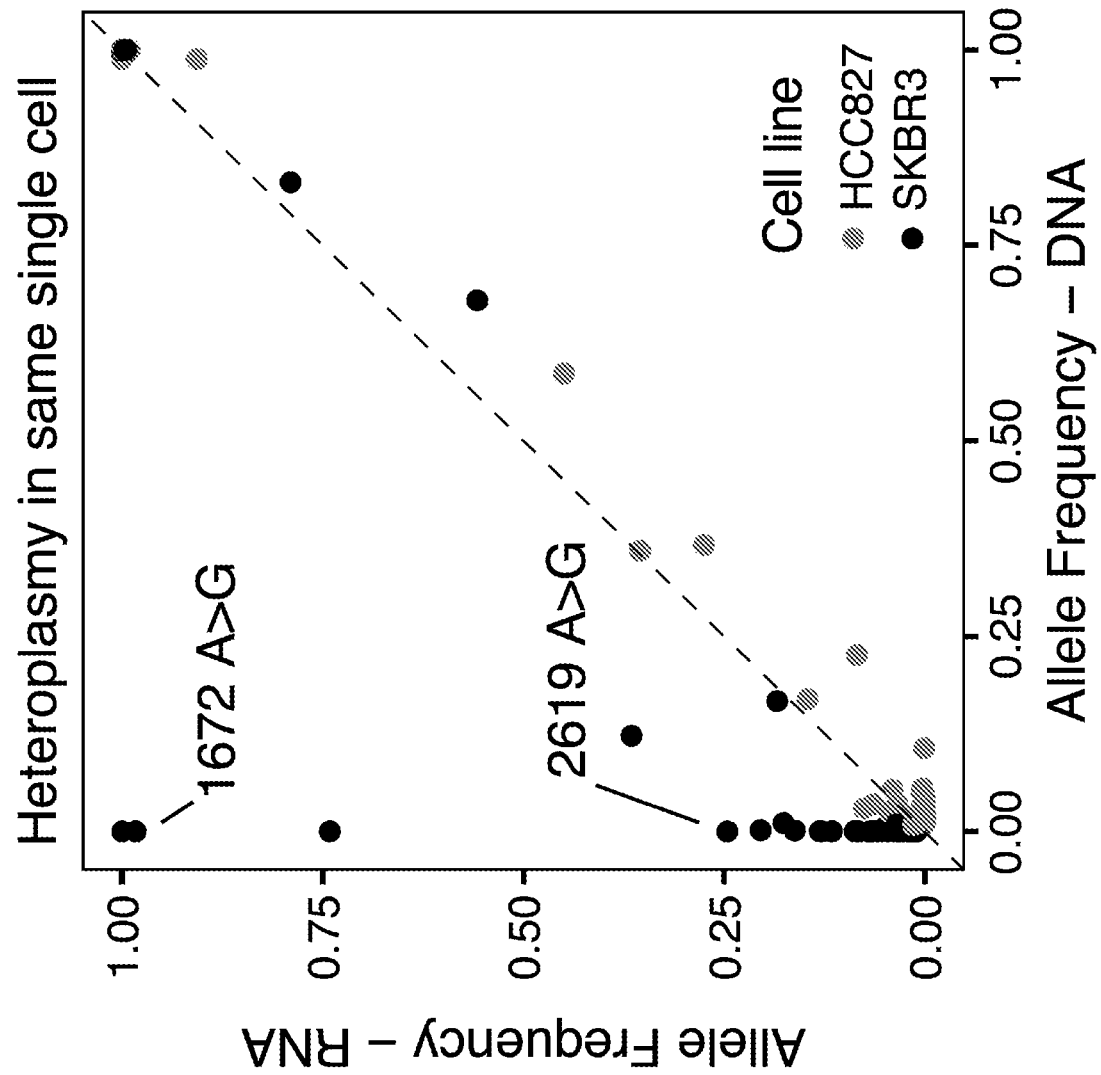
Figure 2C:
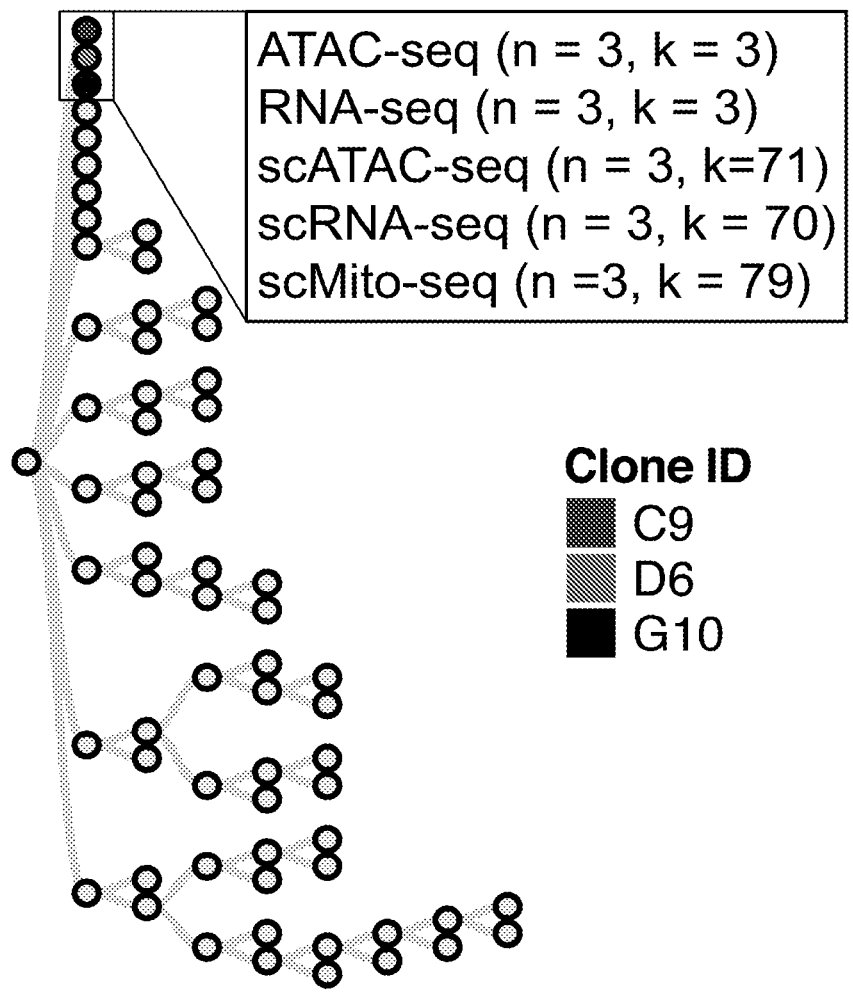
Figure 8C:
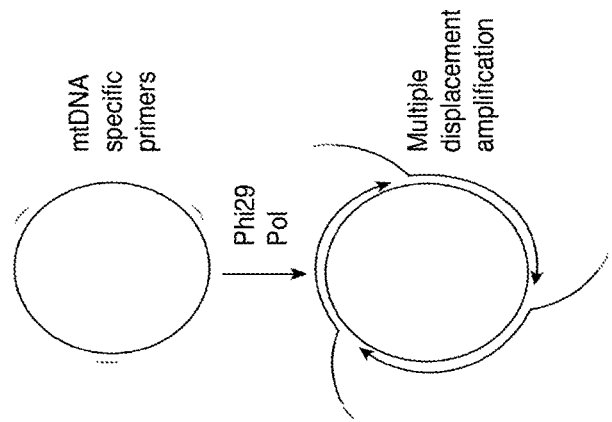
FIG. 8—(A) Mean transcriptome coverage per cell across mm10 mitochondrial genomes for mESC samples. Arrows indicate a specific gene uniformly covered by Smart-seq technologies but 3' biased in most other technologies. (B) Cumulative density plot of mean base pair coverage for each technology. While the Smart-Seq approaches have superior coverage for most base pairs, including 50% at 30× coverage in this data set, CEL-seq2 and SCRB-seq cover 3' transcript ends more deeply. (C) Schematic of scMito-seq using rolling circle amplification for high-fidelity amplification of mitochondrial DNA. (D) Mitochondrial coverage per million sequence reads across three different technologies. The median cell coverage per million reads is noted. (E) Allele frequencies as ascertained by single-cell technologies compared to population ATAC-seq. The sum of reads for single cells is used to compute the allele frequencies. (F) Hierarchical clustering of all TF1 genotyping data, including bulk and single-cells from independent technologies, across the three clones assayed. 210/220 cells readily cluster and show a genotype consistent with the bulk data.
Figure 8B:
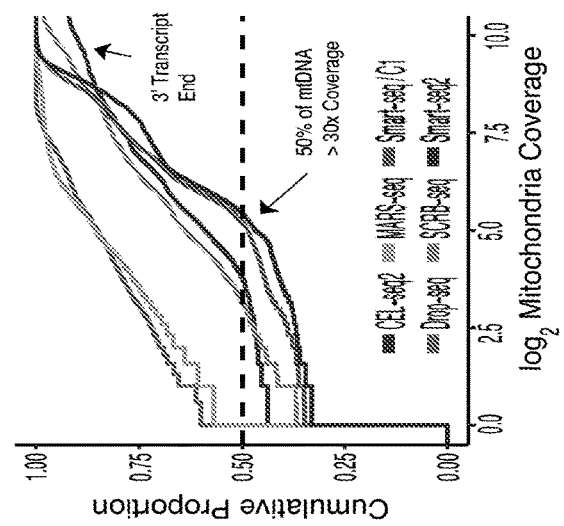
Figure 8A:
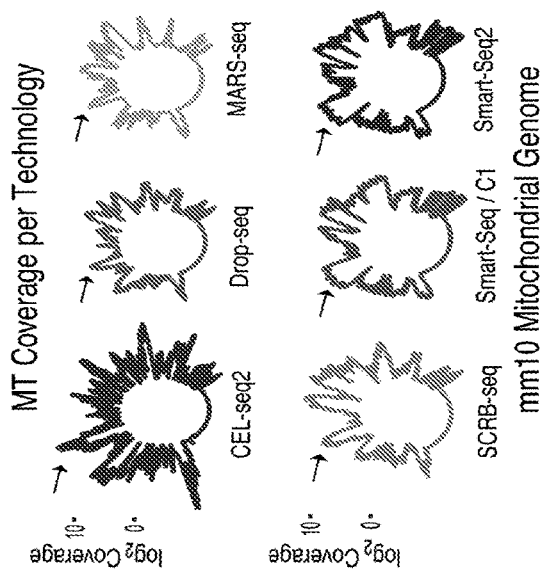

Next, Applicants systematically compared the ability to detect mtDNA mutations at various levels of heteroplasmy in three TF1 cell clones using bulk ATAC-seq (as in FIG. 1B,C), bulk and scRNA-seq (SMART-seq2), scATAC-seq (C1, Fluidigm), and a single cell mtDNA sequencing approach (by single cell adapted rolling circle based mtDNA amplification; scMito-seq, (30)) (FIG. 2C, FIG. 8C). There was high concordance in the frequencies of RNA and DNA-derived mitochondrial genotypes across all methods (in addition to RNA-specific mutations, as described above)

Figure 2D:
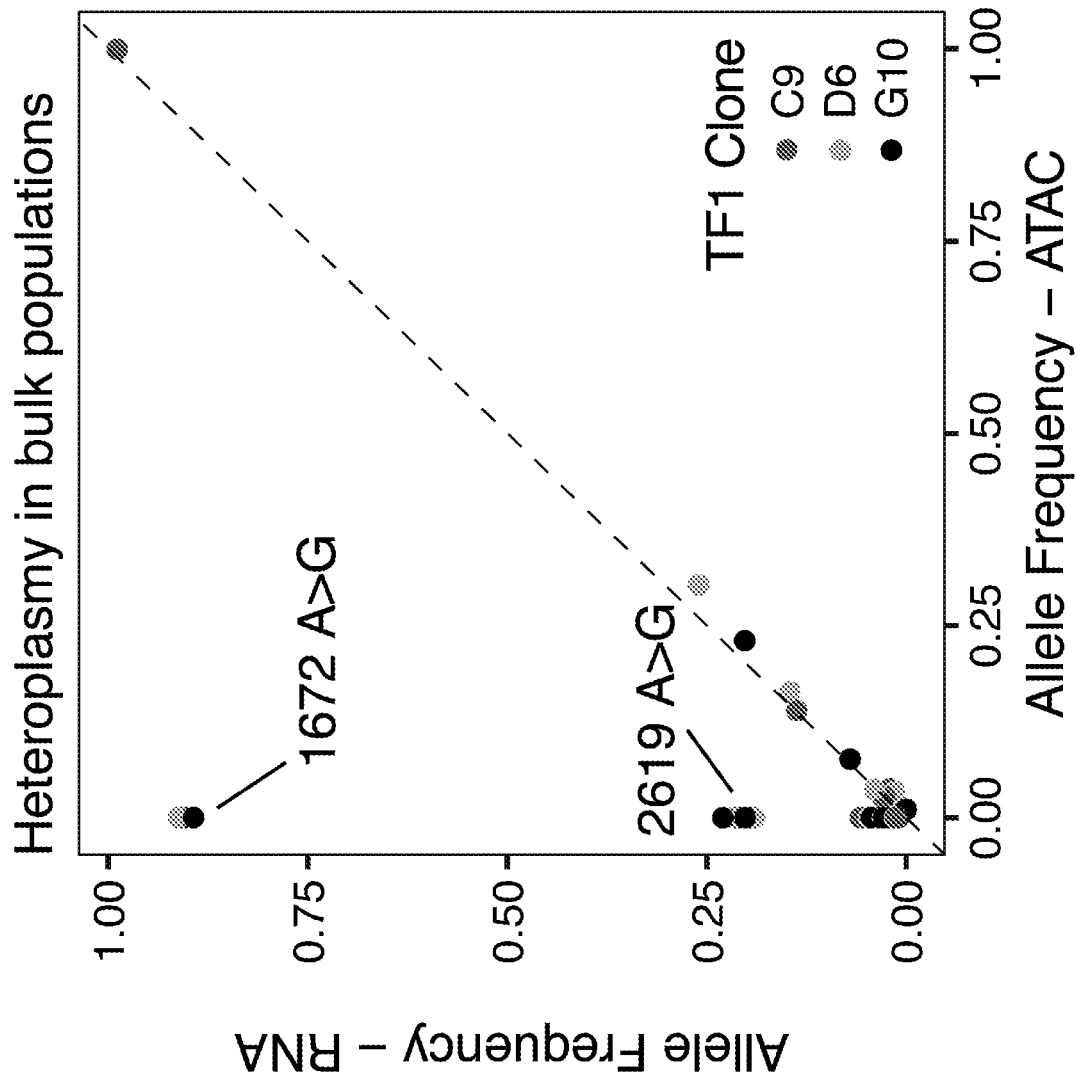
Figure 2E:
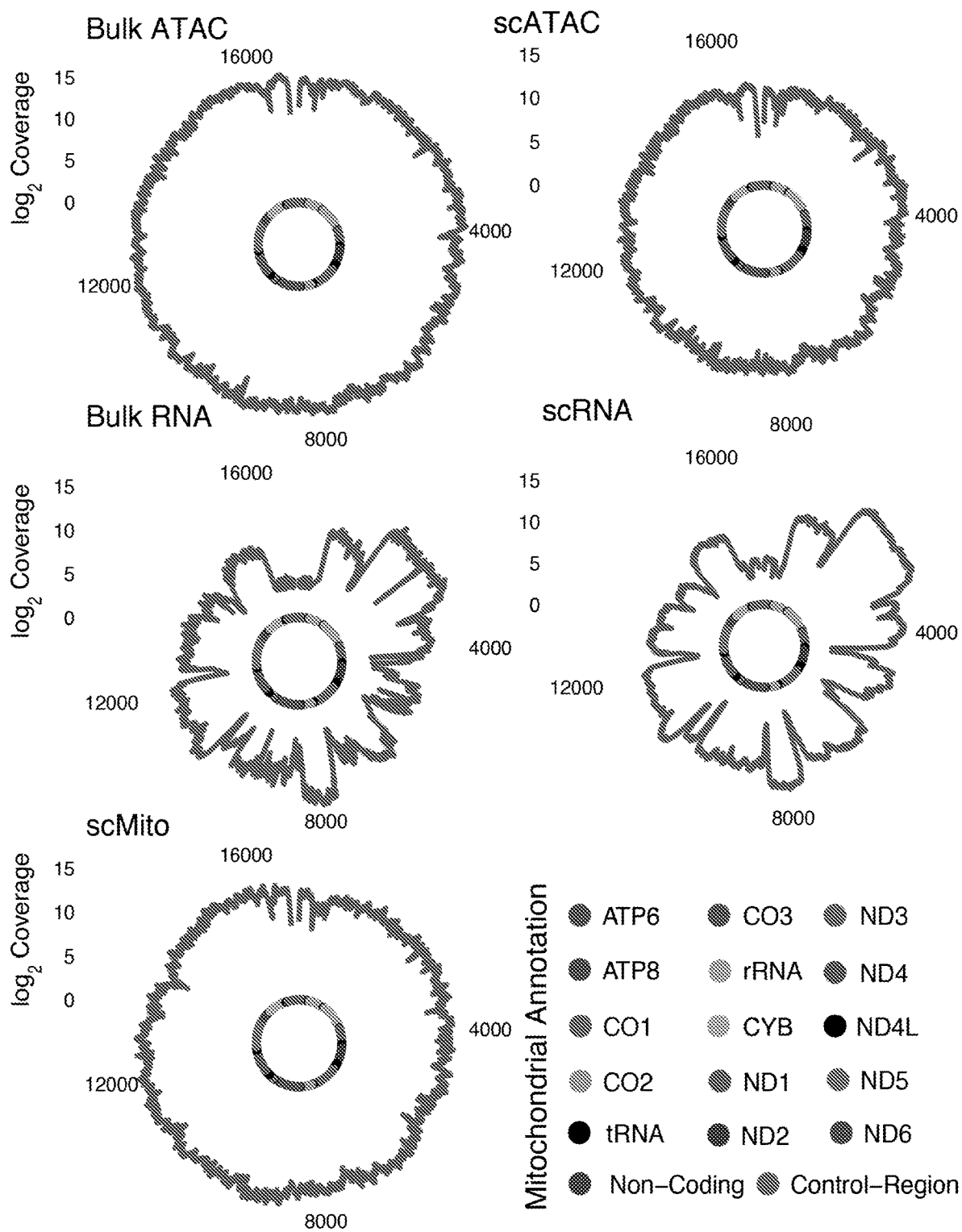
Figure 2F:
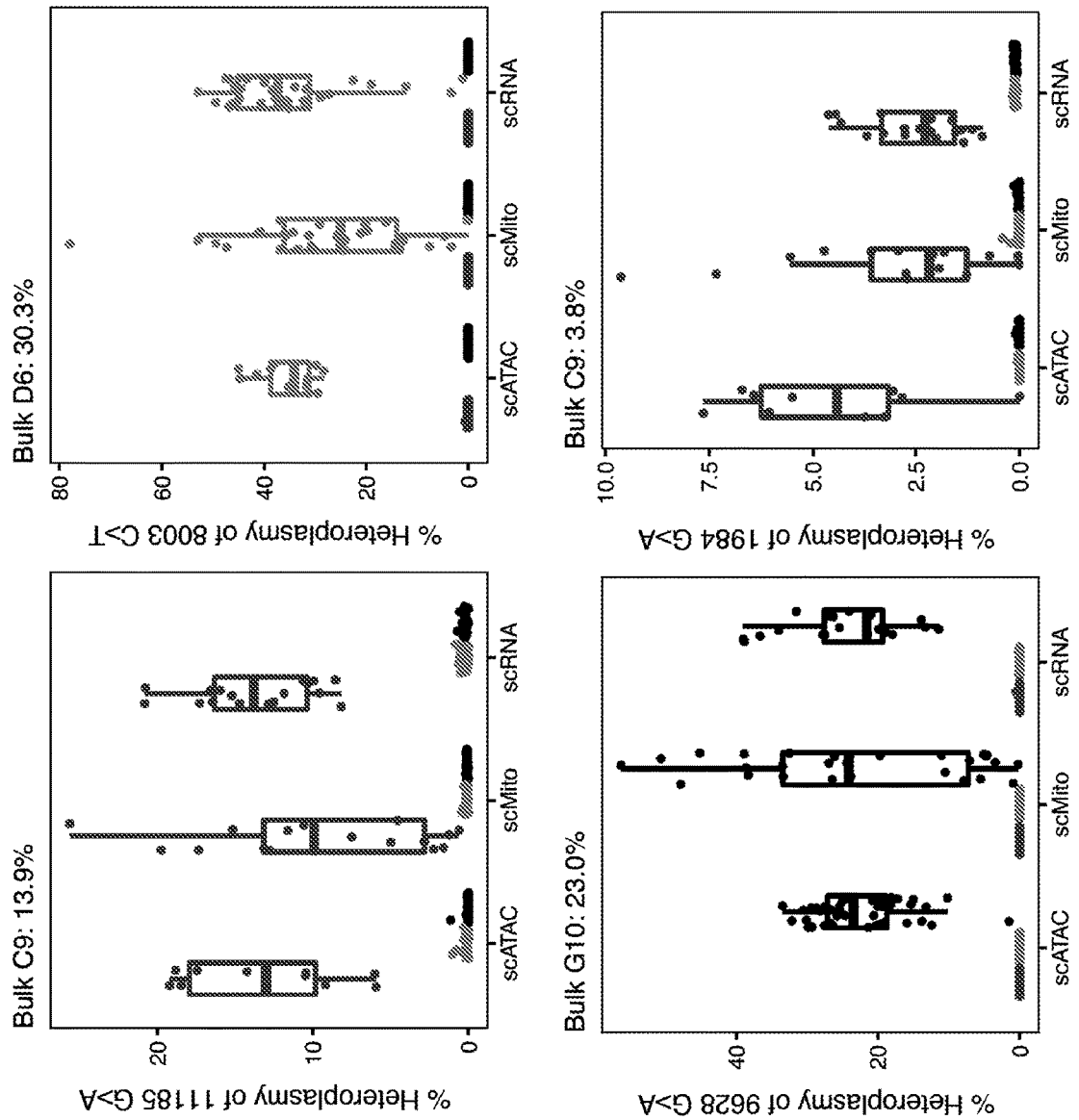
Figure 8D:
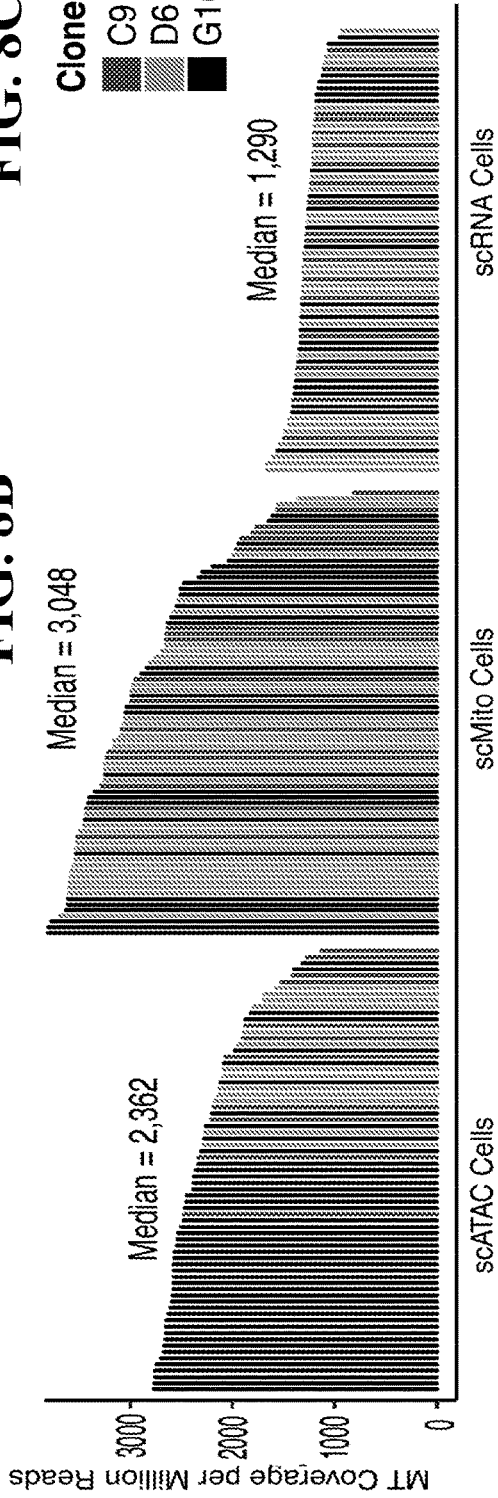
Figure 8E:
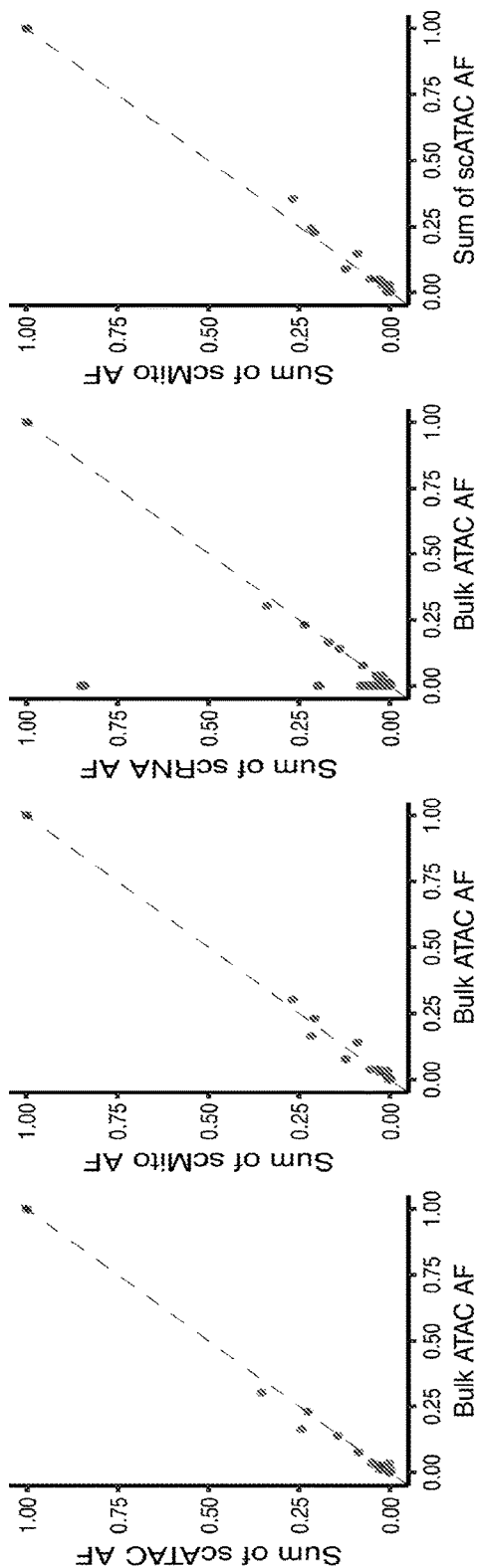
Figure 8F:
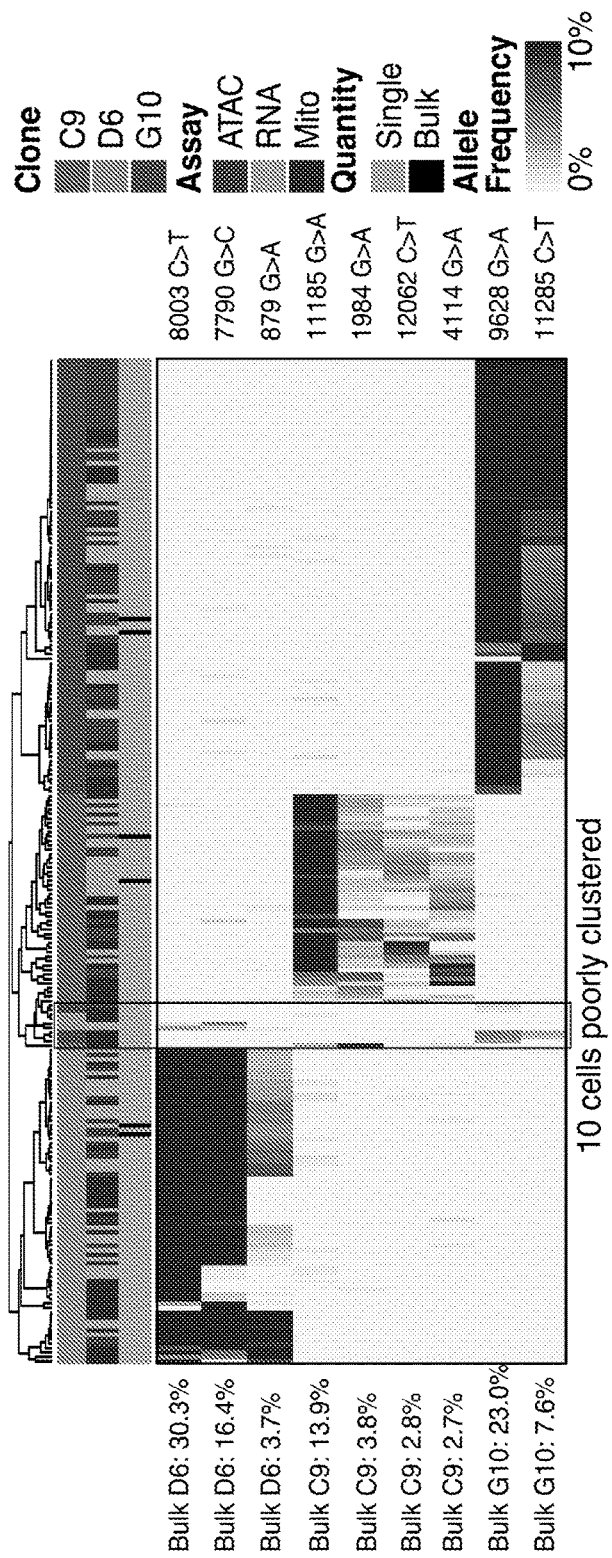

(FIG. 2D, FIG. 8E). As expected, scATAC-seq and scMito-seq had more uniform coverage of the mitochondrial genome than SMART-seq2 (FIG. 2E, FIG. 8D). Data from all methods allowed us to detected the previously identified unique clonal genotype for 95.4% (210/220) of cells at similar allele frequencies (FIG. 2F), and to infer clonal ancestry by hierarchical clustering (FIG. 8F). In particular, with additional filters to exclude common RNA modifications and artefactual variants (FIG. 4, SOM), the common SMART-seq2 technique can accurately identify heteroplasmic mitochondrial mutations for lineage tracing, while also providing a paired measurement of cell state.

Figure 3A:
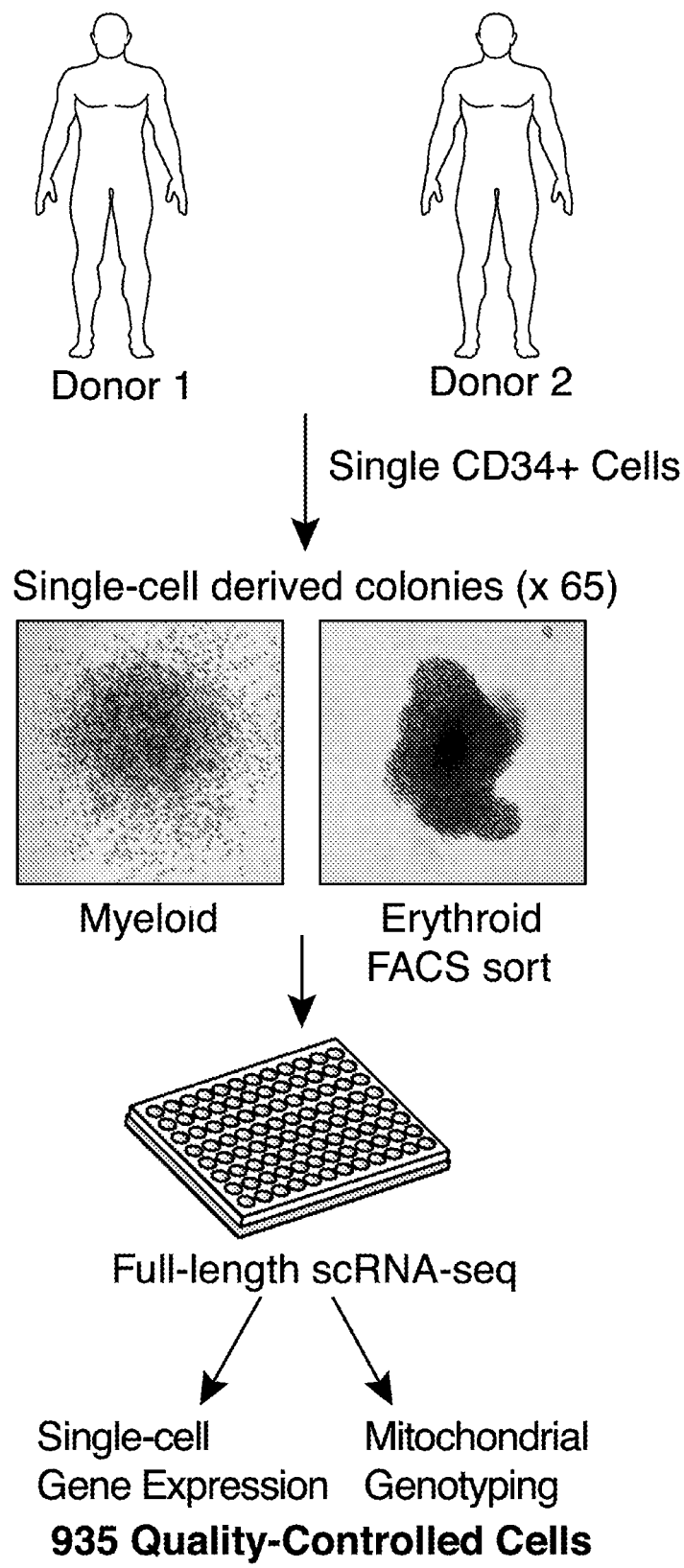
FIG. 3—Mitochondrial mutations are stably propagated in primary hematopoietic cells. (A) Schematic of experiment where hematopoietic colonies are derived from single primary CD34$^+$ HSPCs in semi-solid media, which were then picked and sorted before performing scRNA-seq. (B) Dimensionality reduction on gene expression profiles derived from cells shows donor mixing but separation of erythroid and myeloid cells defined by (C) HBB and (D) MPO mRNA expression. (E) Dimensionality reduction on mtDNA heteroplasmy shows donor separation. (F) Polymorphic mutation present uniquely in donor 1, and (G) heteroplasmic mutation present only in a specific colony. (H) Depiction of colony-specific mutations for Donor 1. (I) Boxplots for 14 selected colony-specific mutations in individual cells from 14 separate colonies derived from Donor 1.
Figure 3B:
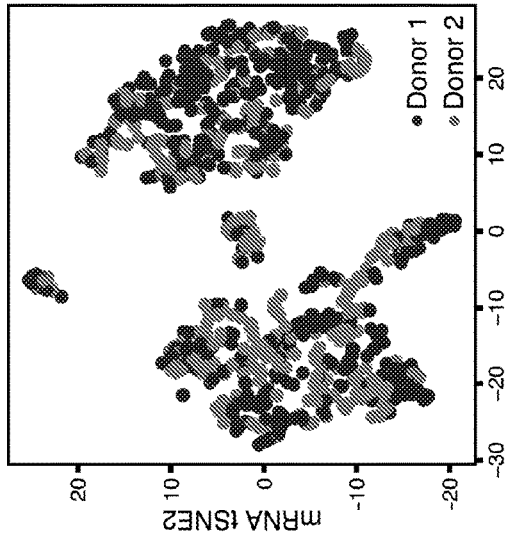
Figure 3C:
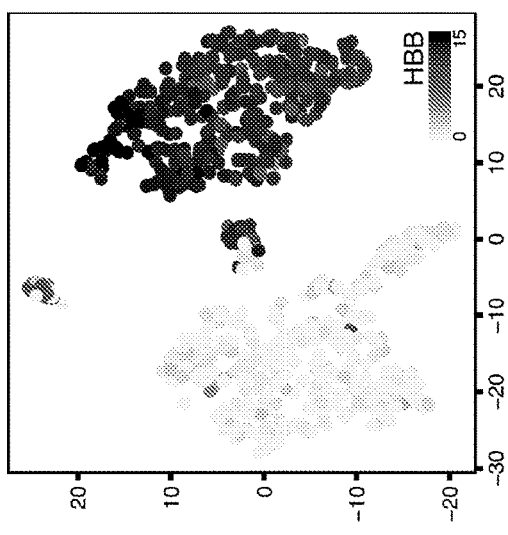
Figure 3D:
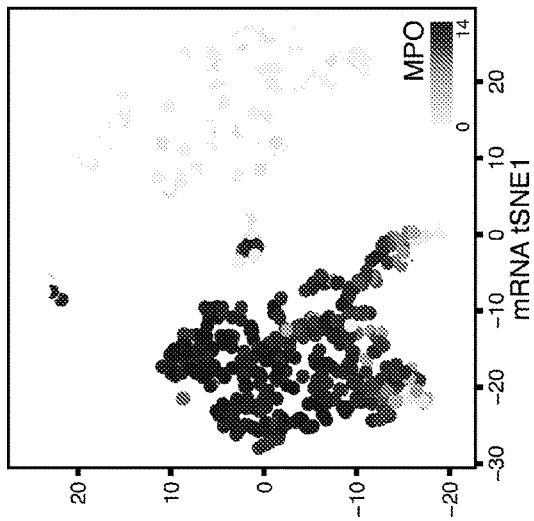
Figure 3E:
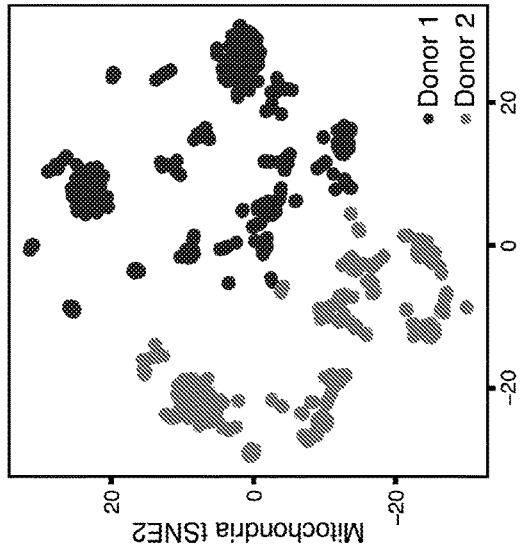
Figure 3F:
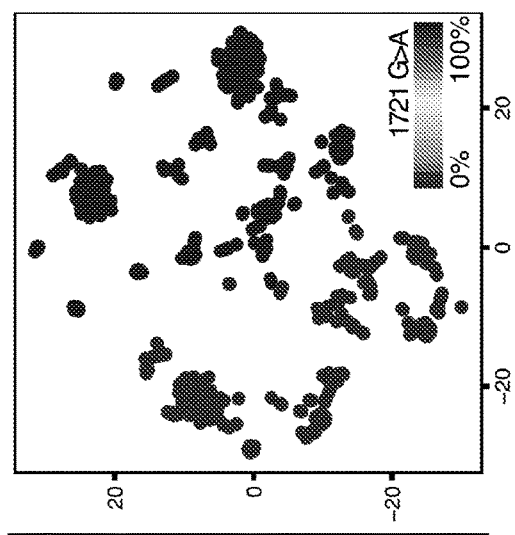
Figure 3G:
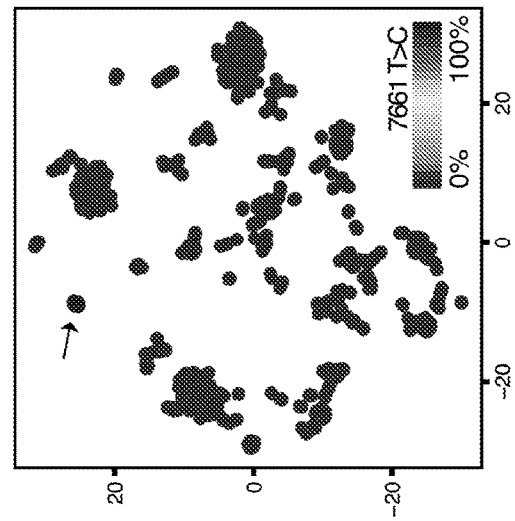
Figure 3H:
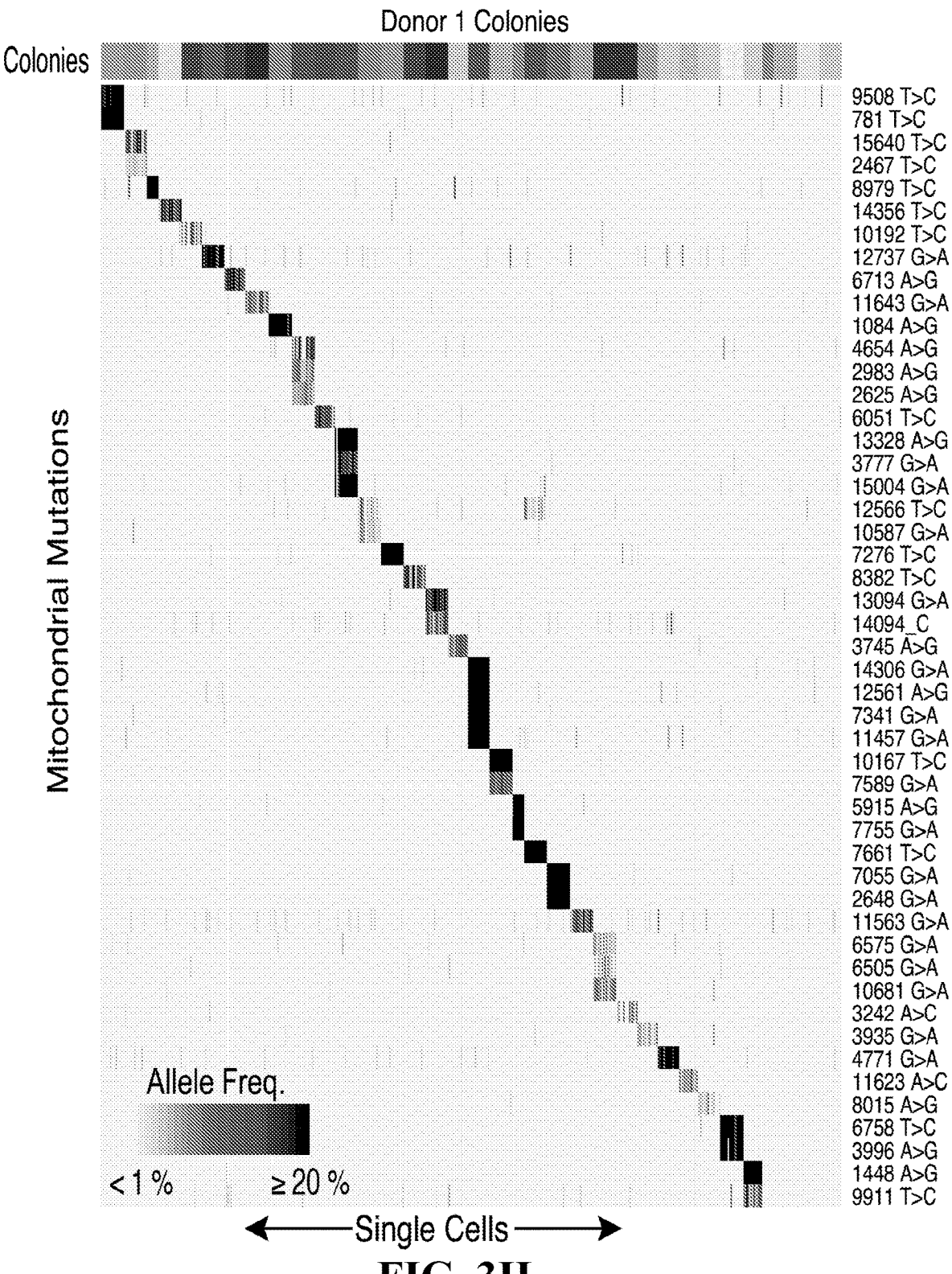
Figure 3I:
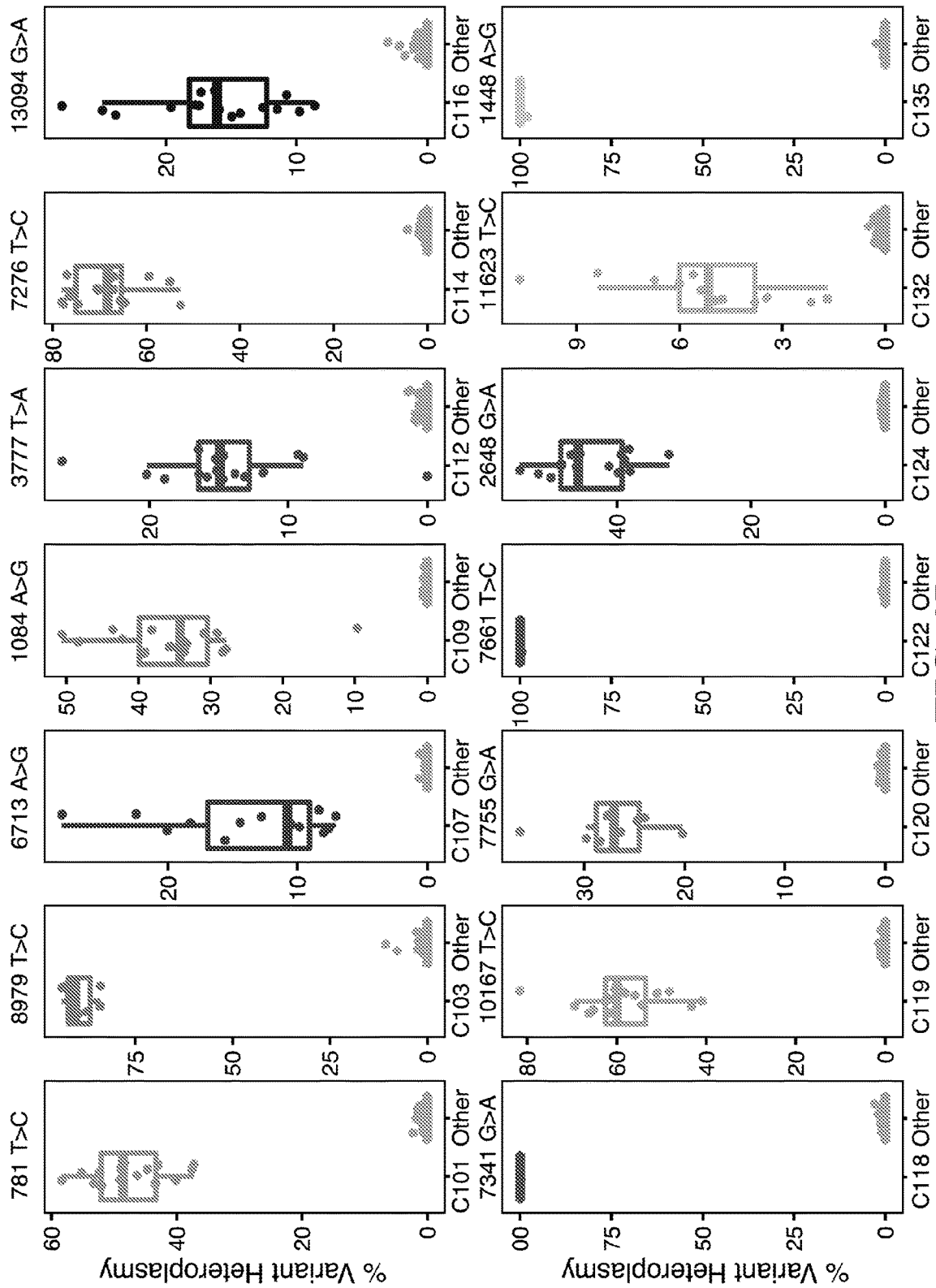
Figure 9F:
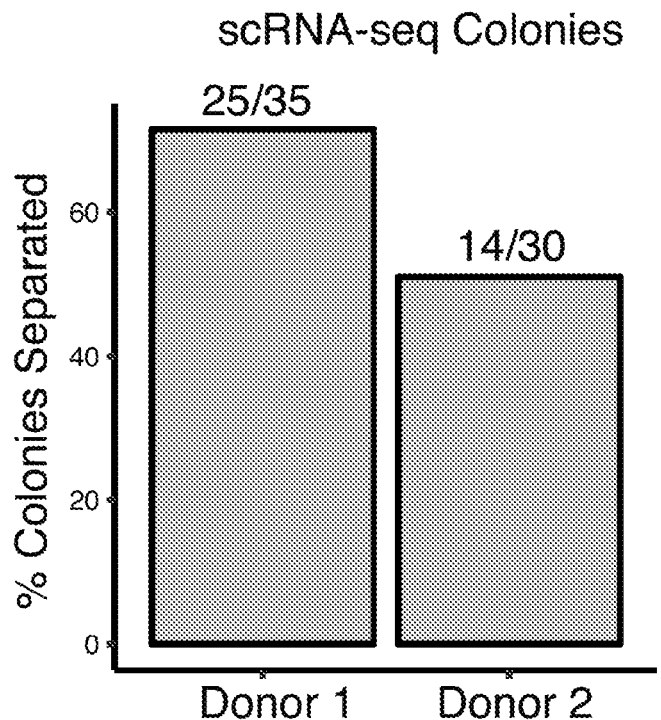
FIG. 9—(A) Both t-SNE plots computed on mRNA gene expression profiles (top) and mitochondrial genotypes (bottom) colored by the number of genes detected (min. 5 counts) per cell. (B) Both t-SNE plots computed on mRNA gene expression profiles (top) and mitochondrial genotypes (bottom) colored by the fold coverage of the mitochondrial genome per cell. (C) Colony-specific mitochondrial mutations for donor 2. (D) Depiction of colony 105, a mixture of two hematopoietic colonies as confirmed by imaging, gene expression data, and mtDNA genotypes. (E) Identification of potential contaminant cell in colony 112 based on expression and mtDNA genotype. (F) Percent of colonies separated based on mitochondrial mutations for donor 1 and donor 2 for scRNA-seq colony experiment (see FIG. 3A). (G) Colony-specific mutations for donor 1 and donor 2 identified in FIG. 3H and FIG. 9C are non-overlapping. (H) Mitochondrial mutations assayed through bulk ATAC-seq in hematopoietic colonies derived from individual CD34+ HSPCs separate 85% and 100% of colonies in two separate donors. (I) Sorted phenotypic HSCs (CD34+CD38-CD45RA-CD90) assayed with scATAC for three additional donors show unique mutations in >75% of cells. (J) These mutations that distinguish individual HSCs are mostly non-overlapping between donors.
Figure 9G:
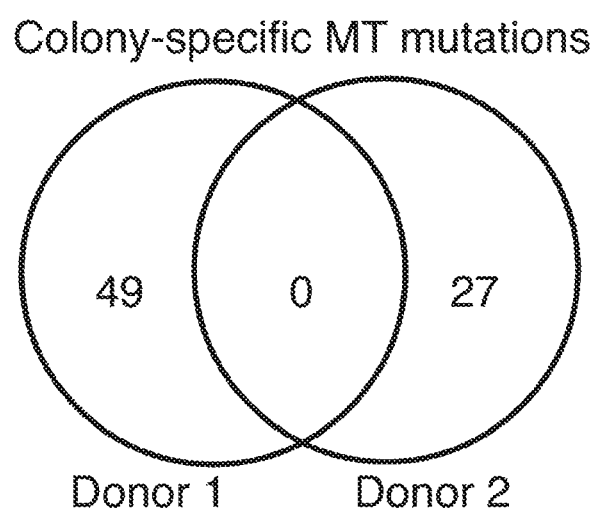
Figure 9H:
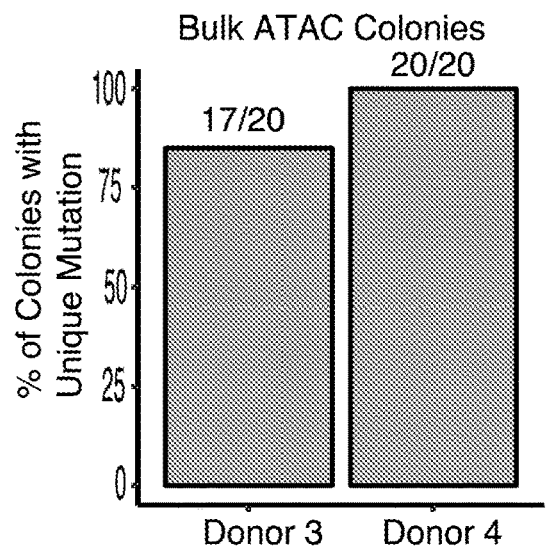
Figure 9I:
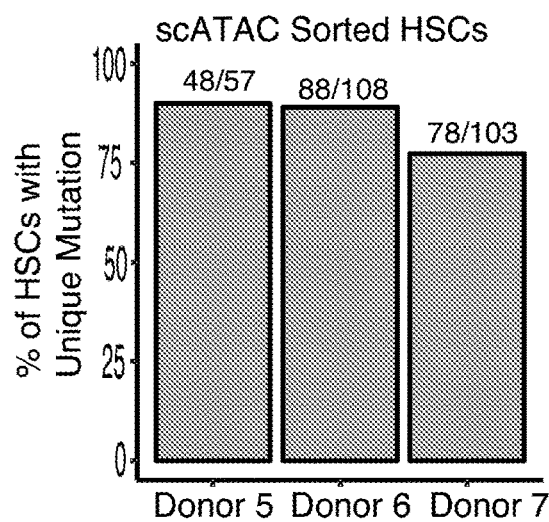
Figure 9J:
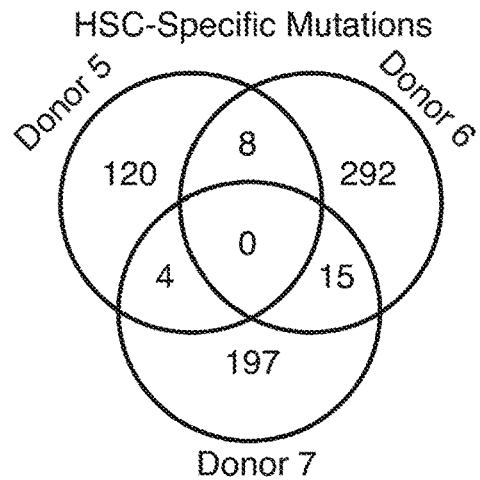

Example 4—Identification of Stable, Diverse Heteroplasmic Mutations in Primary Hematopoietic Cells To extend the findings to primary human cells, Applicants plated human CD34+ hematopoietic stem and progenitor cells (HSPCs) from two independent donors at low density in semi-solid media, derived 65 erythroid and myeloid colonies, and profiled 8-16 cells per colony by scRNA-seq with SMART-seq2 (FIG. 3A). The cells composing any individual colony are derived from a single distinct hematopoietic progenitor cell. Of 993 profiled cells, Applicants retained 935 (94.1%) after transcriptomic and mitochondrial genotype quality metrics (SOM). As expected, based on expression profiles alone, the cells partitioned to two major clusters, corresponding to erythroid and myeloid cells, consistent with colony morphology and irrespective of donor (FIG. 3A-D, FIG. 9A,B). Conversely, the mitochondrial DNA mutation landscape readily enables separation of different donor cells as well as single cells from individual colonies based on highly heteroplasmic mutations (FIG. 3E-G, FIG. 9A,B). Supervised analysis shows the presence of colony-specific mutations within each donor (Mann-Whitney U Test p-value <$10^{-10}$), a subset of which distinguishes most cells in each colony from all other cells from the same donor (table S2; FIG. 3H, FIG. 9C). Specifically, Applicants identified unique clonal mutations in 71% of colonies for donor 1 and 47% for donor 2, each detected at similar frequencies in at least 80% of cells of the same colony (FIG. 9F; SOM). The extent of heteroplasmy varied considerably across colony-specific mutations, with three mutations that achieved near-homoplasmy (FIG. 3I). Certain experimental challenges, such as mixing between adjacent colonies (FIG. 9D,E) likely result in an underestimate of this percentage and thus the true effectiveness of separation using mitochondrial mutations. Applicants observed similar mutational diversity with bulk ATAC-seq of colonies similarly derived from two other donors (FIG. 9H), and in 268 sorted phenotypic hematopoietic stem cells (HSC) from three additional donors from a previously published scATAC-seq study (36) (FIG. 9I). Thus, high mtDNA mutational diversity is already present in HSCs that are derived directly from bone marrow (FIG. 9I). Importantly, the colony-specific mitochondrial mutations do not overlap between the two donors in the scRNA-seq analysis (FIG. 9G) and show very limited overlap between the three donors in the scATAC-seq analysis (FIG. 9J). Thus, adult human HSPCs show a large spectrum of mtDNA mutational diversity, consistent with previous reports (18), and are stably propagated in daughter cells at a level that may allow for lineage tracing studies of in vivo human hematopoietic differentiation.

Example 5—Inference of Clonal Structure by Combining Single Cell and Bulk Data

Figure 4D:
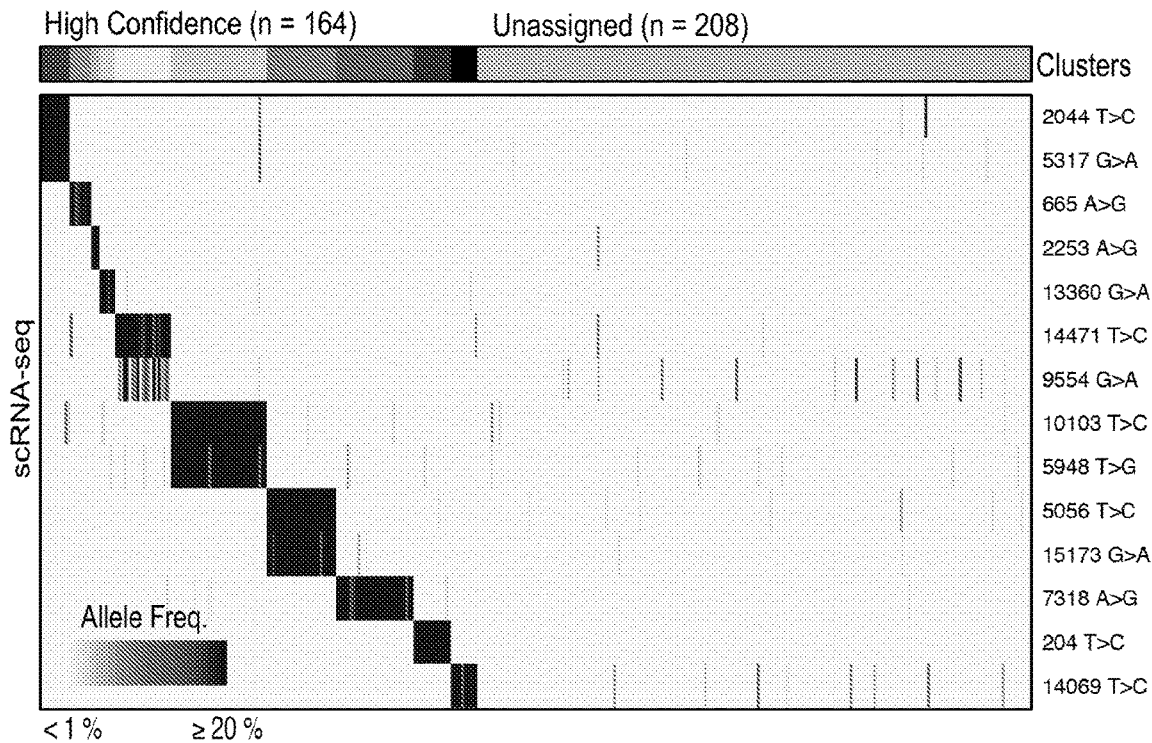
FIG. 4—Mitochondrial mutations deconvolve clonal contributions in mixtures. (A) Schematic of expansion of CD34$^+$ HSPCs followed by genotyping both in bulk and in single cells. These genotypes are used to assign individual cells to the most probable cell of origin. (B) Comparison of base quality scores for the sum of scRNA-seq cells and ATAC-seq implicates a set of high-confidence variants detected by both technologies (BQ>20). (C) Comparison of allele frequencies determined by the sum of single cells from scRNA-seq and the bulk population from ATAC-seq. Probabilistic clustering identifies subsets of cells that can be confidently clustered based on heteroplasmic mutations from (D) scRNA-seq and (E) scATAC-seq. (F) Two examples of peaks inherited from specific clones propagated through the experiment and recovered by mitochondrial clustering. (G) Boxplots for 8 selected cluster-specific mutations in individual cells for 8 separate clusters derived from the scATAC-seq mixing experiment.
Figures 4E, 4F:
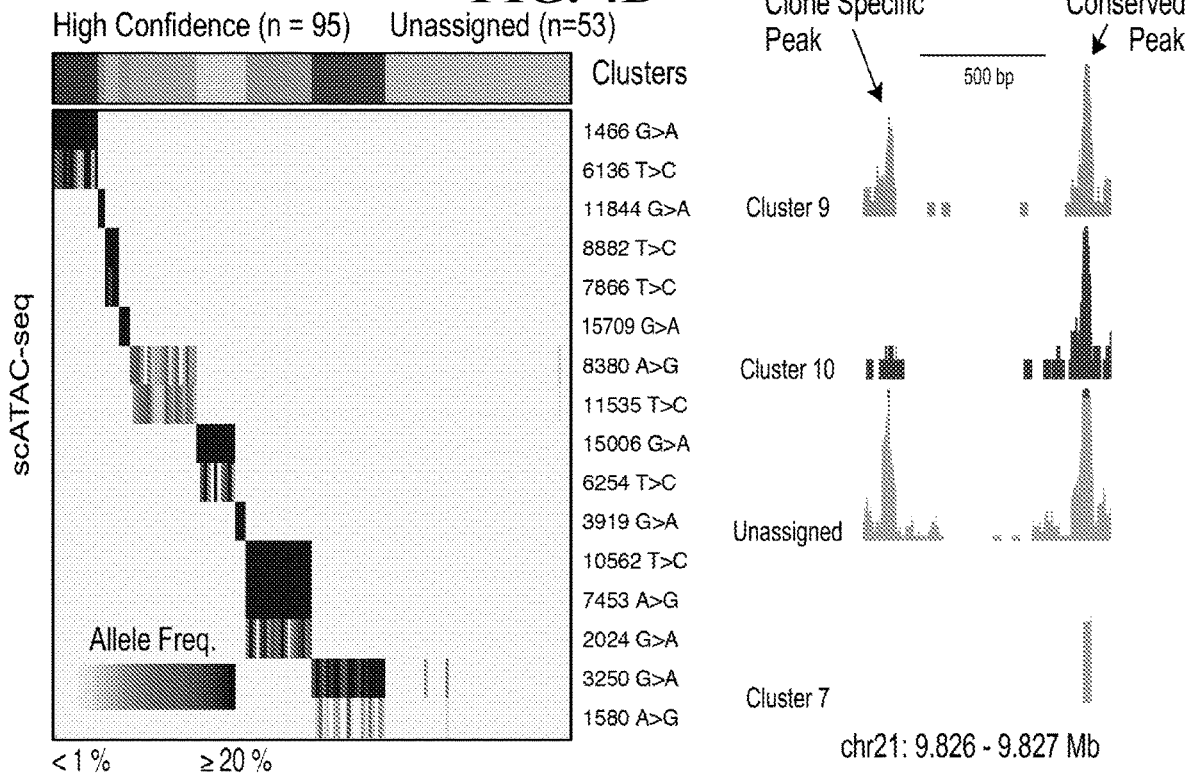
Figures 10E, 10F:
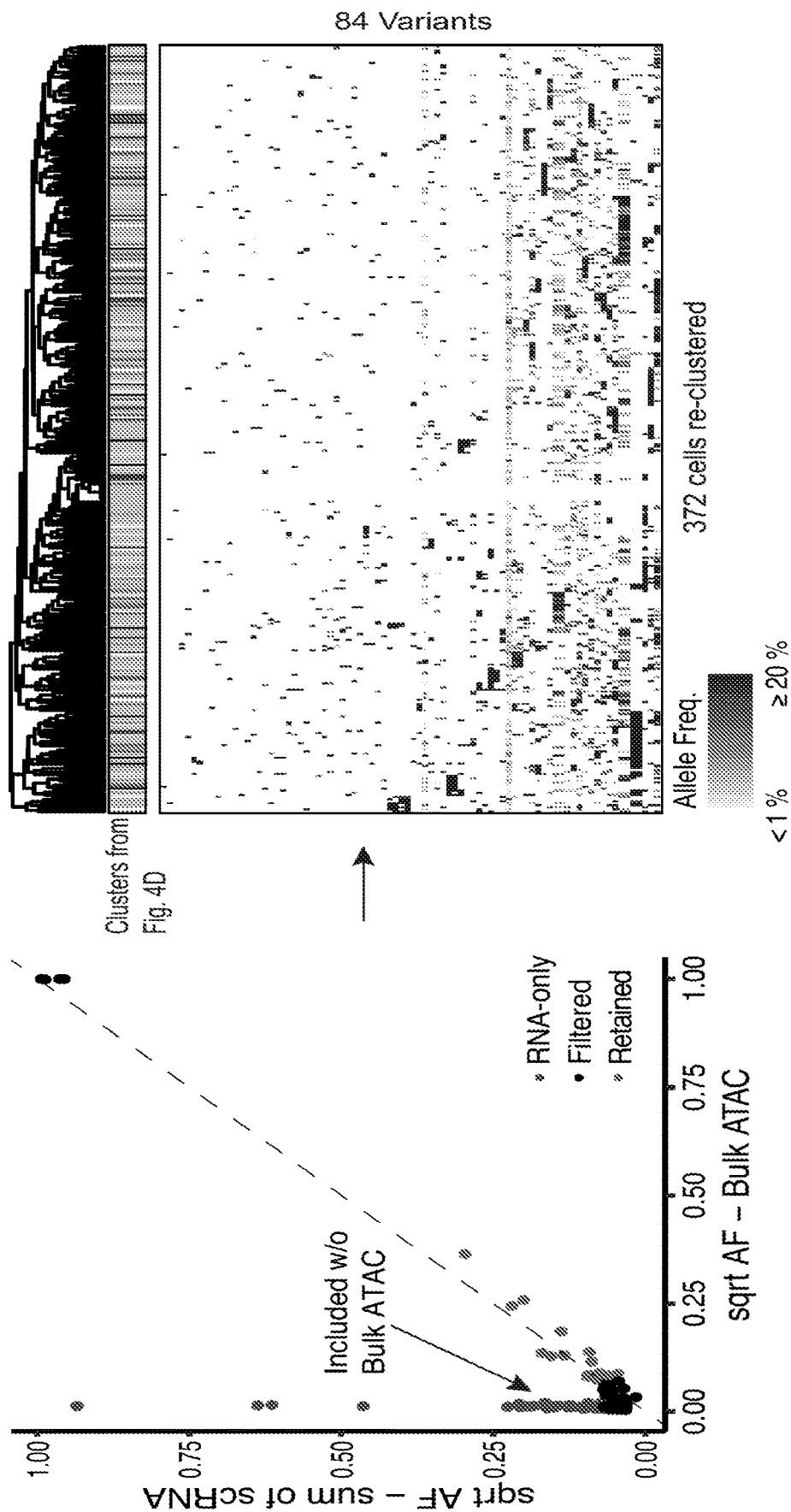
FIG. 10—(A) Comparison of allele frequencies determined by the sum of single cells from scATAC-seq and population ATAC-seq. Simulated number of cells clustered using cell input for (B) scRNA-seq experiment (compare to FIG. 4D) and (C) scATAC-seq experiment (compare to FIG. 4E). (D) Boxplots for 8 selected cluster-specific mutations for 8 separate clusters derived from the scRNA-seq mixing experiment. (E) Inclusion of scRNA-seq-specific mutations (denoted in red) in the clustering analysis. (F) Hierarchical clustering of cells from FIG. 4D using red and blue mutations noted in the previous panel. The color bar shown above the cells is the classification inferred from FIG. 4D.

Despite the clonal mtDNA mutations, reliable assignment of a cell to a specific lineage or clone using an unsupervised mitochondrial mutation profile estimated by scRNA-seq is challenging due to the presence of RNA modifications and the assay's technical noise (32) (FIG. 2B, FIG. 4A-D, FIG. 8E, FIG. 10E,F). To address this challenge, Applicants devised a strategy where Applicants first identify high-confidence heteroplasmic mutations using bulk DNA- or ATAC-seq (FIG. 2B,D), and then call these mutations in individual cells. Similar approaches have been successful for coding mutations in scRNA-seq in tumors (31). To test this, Applicants recovered 30 primary CD34+ HSPCs from donor 2 and expanded them into a single large population over 10 days, and then processed the cells by both bulk ATAC-seq and either scATAC-seq or scRNA-seq (FIG. 4A). Probabilistic k-medoids clustering (SOM) restricted only high-quality mitochondrial variants that were present in the bulk ATAC-seq at allele frequencies >0.5%, and had high per-allele base quality scores (SOM) in bulk and in single cells (FIG. 4B, C) to assign individual cells with high-confidence to 10 clusters consisting of 3-36 cells, with cells in each cluster sharing one or two heteroplasmic mutations at comparable frequencies (FIG. 4D, FIG. 10D). The clusters conformed to expectations under a simulated setting (FIG. 10B,C, SOM). Notably, when all RNA-based mtDNA mutations (including the likely artefactual variants) were included, Applicants could not discern clusters readily (FIG. 10E,F). Applying this approach to cells with mitochondrial mutations called from scATAC-seq, Applicants were similarly able to assign 95 of 148 cells (64%) to 9 different clusters (FIG. 4E,G, FIG. 10A), where Applicants could then identify clone-specific regions of open chromatin (FIG. 4F, SOM).

Example 6—Somatic mtDNA Mutations as Clonal Markers in CML

While the use of mtDNA mutations for lineage tracing appears highly effective in vitro, Applicants wanted to validate the utility of this approach in vivo. Certain malignancies, such as chronic myelogenous leukemia (CML) are known to concomitantly have both somatically mutated and unmutated HSPCs, thus allowing for independent assessments of clonality. Applicants therefore reasoned that the utilization of scRNA-seq data obtained from CML patients at the time of diagnosis, when CML clones predominate, and at 3 and 6 months of therapy, when malignant clones are expected to decrease in frequency relative to unmutated HSPCs (37), could allow for useful insights into how well the mtDNA lineage tracing approach performs in vivo. Applicants analyzed 2,145 cells profiled across 49 samples from 31 chronic myelogenous leukemia (CML) patients by scRNA-seq with the mitochondrial genotyping pipeline. Since neither bulk ATAC- nor DNA-seq were available, Applicants applied a particularly conservative score and identified 242 high-confidence variants (SOM). These mitochondrial genotypes robustly separated donors by unsupervised analysis (FIG. 5A, FIG. 11A,G), consistent with the known mtDNA variation across humans (20, 21).

Figure 5A:
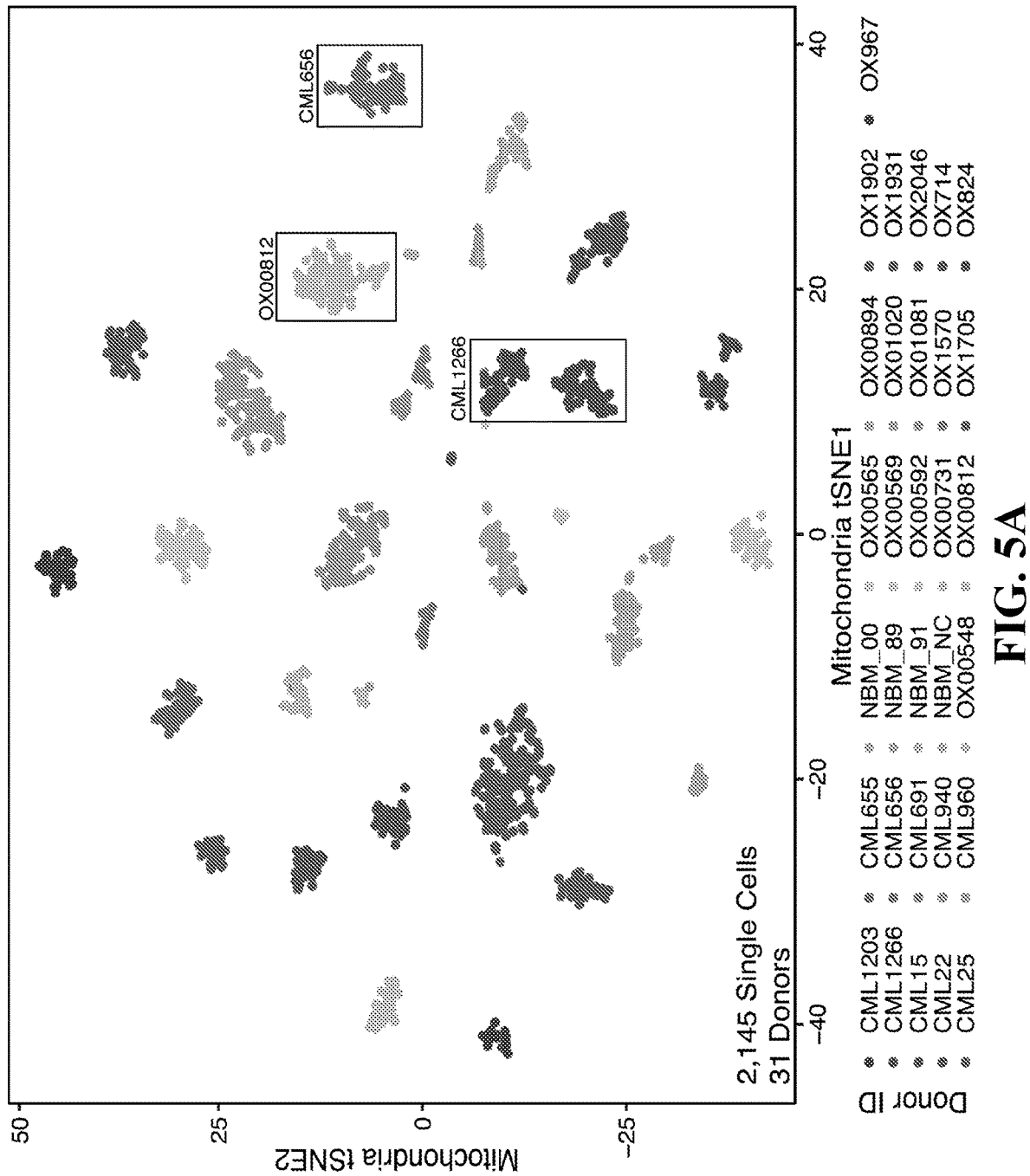
FIG. 5—Utility of mitochondrial mutations in vivo. (A) Two-dimensional tSNE of 31 distinct donors encompassing 2,145 single cells of chronic myelogenous leukemia (CML) shows near-perfect separation of donors based on mitochondrial genotypes. (B) tSNE dimensionality reduction reveals substructure for donor CML1266, separating cells sampled at pre- and during blast crisis. (C) For donor OX00812, cells sampled at 6 months can be separated from cells sampled at diagnosis and <6 months of treatment. (D) Depiction of 3 highly heteroplasmic mutations presently most strongly in BCR-ABL positive cells in donor CML656. (E) Consensus clustering of CML656 transcripts suggests variable annotation in BCR-ABL positive cells at diagnosis. Boxed items indicate potentially erroneous BCR-ABL fusion inference based on mitochondrial mutations. (F) Differentially expressed genes between cells in Cluster 1 comparing cells with and without the 4824 T>C mutation. (G) Sensitive detection of mtDNA genotypes allows identification of recipient- and donor-specific cells after HSCT in AML.
Figure 5B:
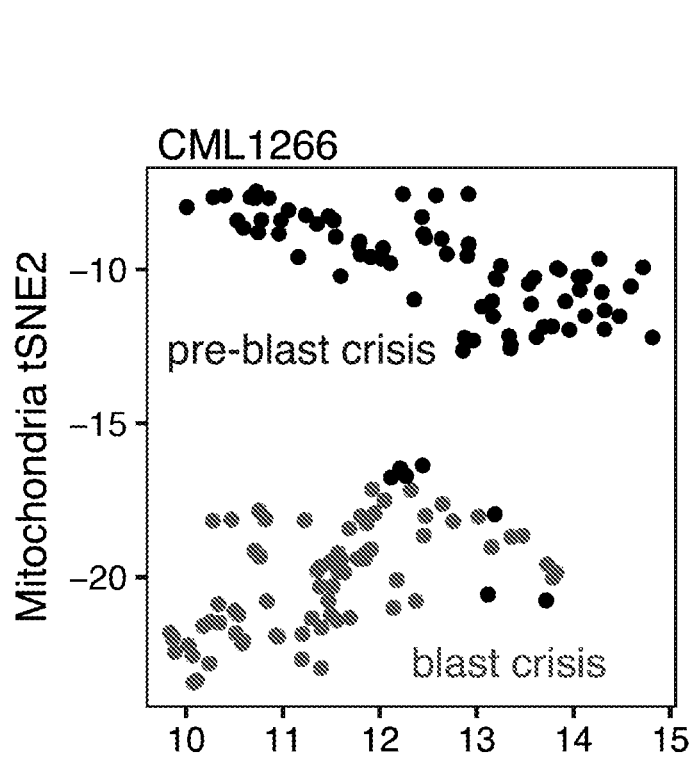
Figure 5C:
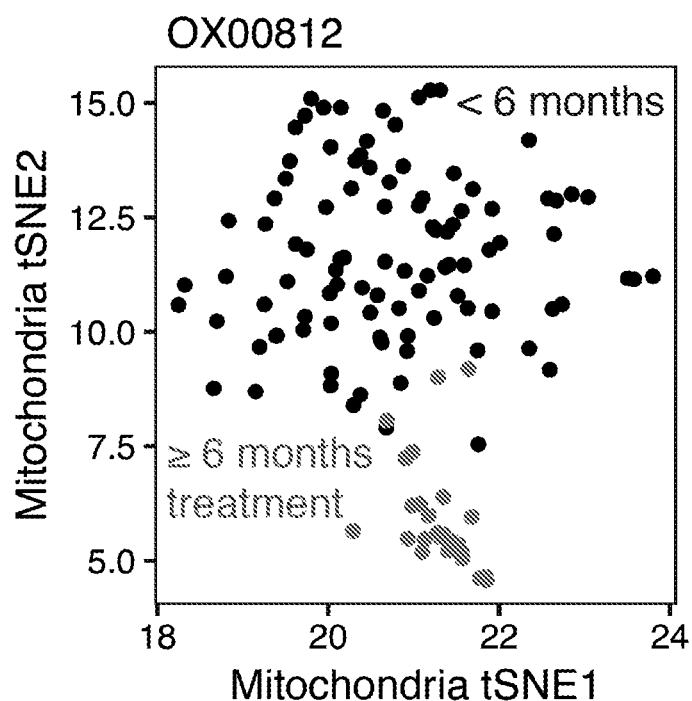
Figure 5D:
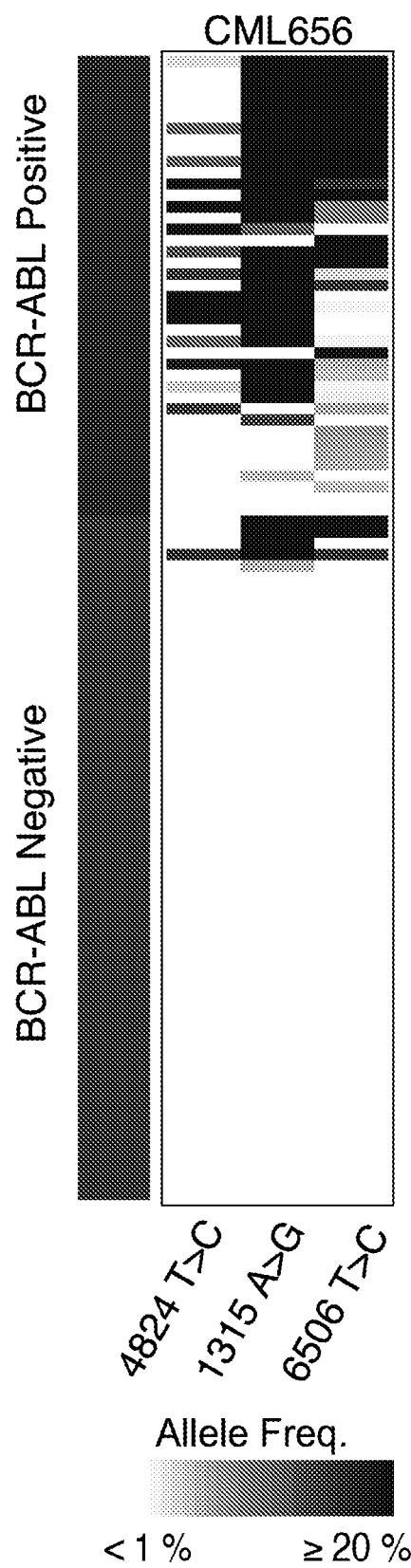

In some patients, mitochondrial genotypes further partitioned cells in a manner consistent with disease stage (FIG. 5B,C, FIG. 11B,C). In one striking example, three heteroplasmic mtDNA mutations were nearly exclusive to BCR-ABL positive cells, but absent in non-leukemic cells from the same donor (FIG. 5D). Importantly, integration of these mtDNA mutations when investigating heterogeneous samples appears to improve stratification of malignant cells from benign cells compared to the BCR-ABL genotyping assay alone, resulting in 100% concordance with transcriptional signatures (FIG. 5E, boxed cells in Cluster 1 and 2). Interestingly, although the frequency of BCR-ABL positive cells decreased with treatment, one mitochondrial mutation (6506 T>C) present in the majority of BCR-ABL positive cells at diagnosis continued to predominately mark the BCR-ABL positive cells post-treatment, thereby also validating the stable propagation of mtDNA mutations over extended periods of time in vivo (FIG. 5E). On the other hand, BCR-ABL positive cells with the 4824 T>C mutation were depleted, implying that this sub-clone was likely more susceptible to therapy.

These clones were associated with distinct transcriptional states. Unsupervised clustering by expression profiles partitioned this patient's cells into three clusters, Clusters 1 and 2 both comprised of cells from the initial sample at diagnosis, but separated by BCR-ABL status as well as by mitochondrial genotype and enriched for mtDNA mutations 6506 T>C and 4824 T>C; Cluster 3 comprised of cells obtained 3 and 6 months after start of treatment, with either BCR-ABL status and either WT or 6506 T>C mitochondrial genotype (FIG. 5E). Differential expression analysis of Cluster 1 cells stratified by the 4824 T>C mutation status (FIG. 5F), identified the induction of PDIA6, a gene implicated in cancer cell proliferation (38), in cells lacking the mutation, suggesting that it may be associated with the observed variation in sub-clone frequencies. Thus, mitochondrial genetic analysis can improve stratification of malignant cells, and enhance understanding of (sub)-clonal evolution.

Example 7—In Vivo Chimerism Inferred from mtDNA Mutations

Mitochondrial genotyping can also readily track donor and recipient chimerism during HSC transplantation (HSCT). Applicants analyzed scRNA-seq profiles of peripheral blood mononuclear cells (PBMCs) from an AML patient before and after HSCT, which were profiled with 3' directed massively parallel scRNA-seq (39). Although such approaches have substantially reduced coverage of mtDNA, (FIGS. 8A and 11D,E), Applicants reasoned that a small number of highly heteroplasmic or homoplasmic mutations should still be detectable. Indeed, the analysis revealed two homoplasmic mitochondrial alleles distinguishing the donor and recipient (FIG. 5G), and inferred that ~99.6% of cells sampled post-transplant were from the donor. These results demonstrate the potential utility of using mitochondrial mutations to measure the dynamics of donor chimerism in transplantation settings and such approaches may demonstrate even greater sensitivity in conjunction with currently employed approaches (39, 40).

Example 8—mtDNA Mutational Diversity Across Human Tissues

Figure 6A:
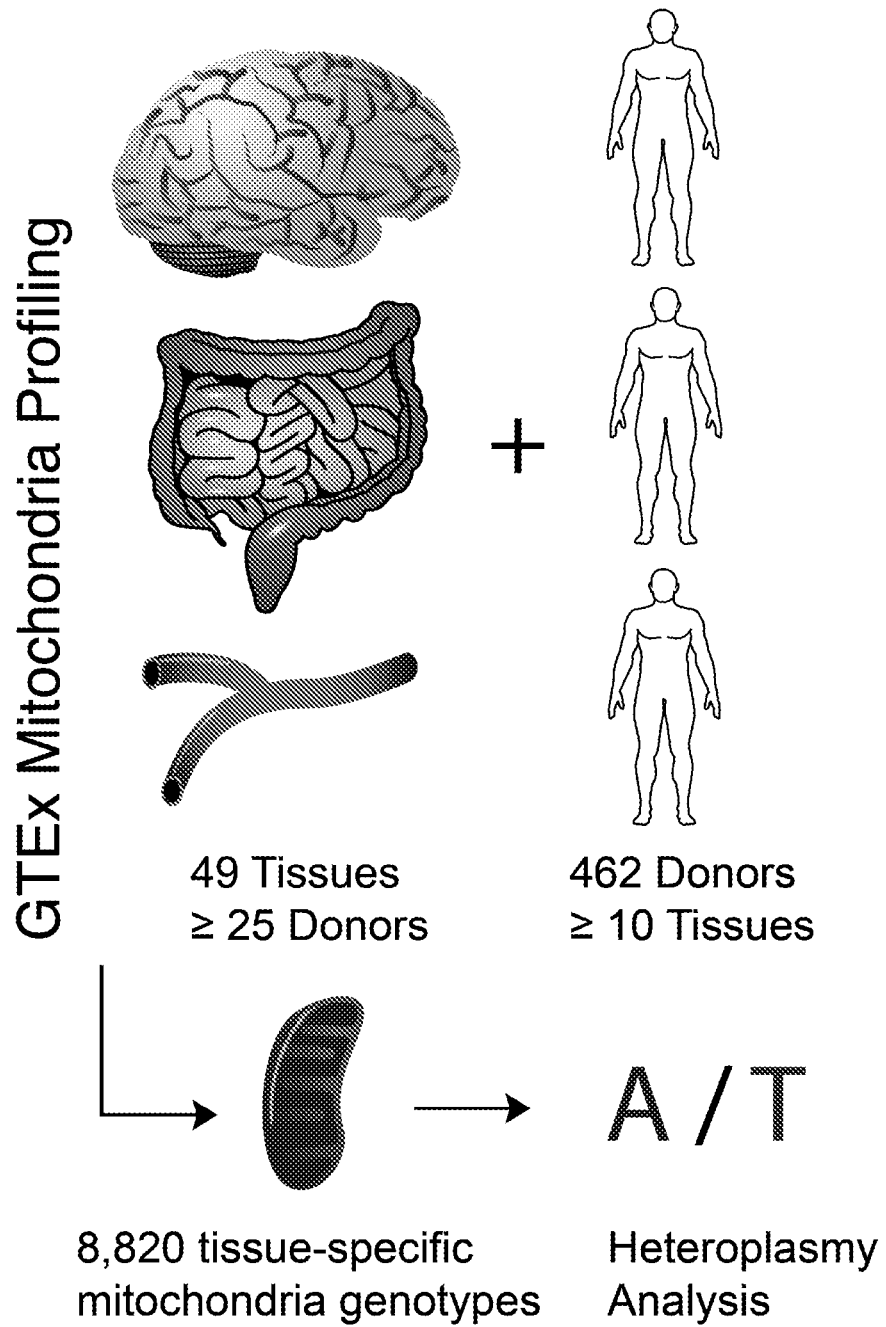
FIG. 6—Presence of widespread tissue-specific mitochondrial heteroplasmic mutations in the GTEx cohort. (A) Schematic of analysis identifying donors and mutations for subsequent analysis. (B) Proportion of aligned reads that map to the mitochondrial genome for each tissue. (C) Comparison of the mean mitochondrial coverage across all donors for heart, liver, and blood. (D) Landscape of tissue-specific heteroplasmic mutations (>3% heteroplasmy) in GTEx RNA-seq data. (E) Bar graphs depicting the number of tissue-specific heteroplasmic mutations at variable allele frequency thresholds. (F) Tissues with frequent specific mutations across tissues sampled in GTEx.
Figure 6B:
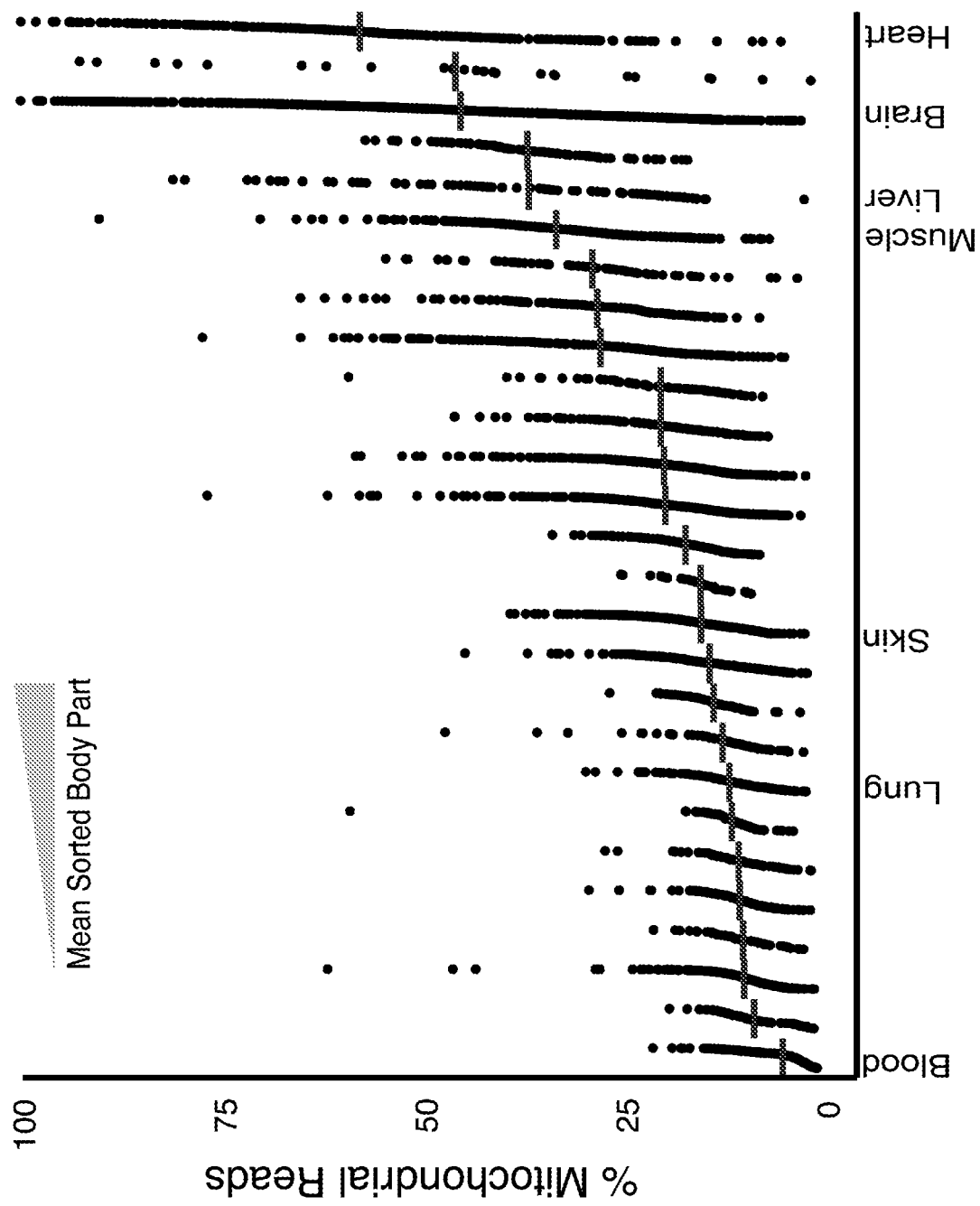
Figure 6C:
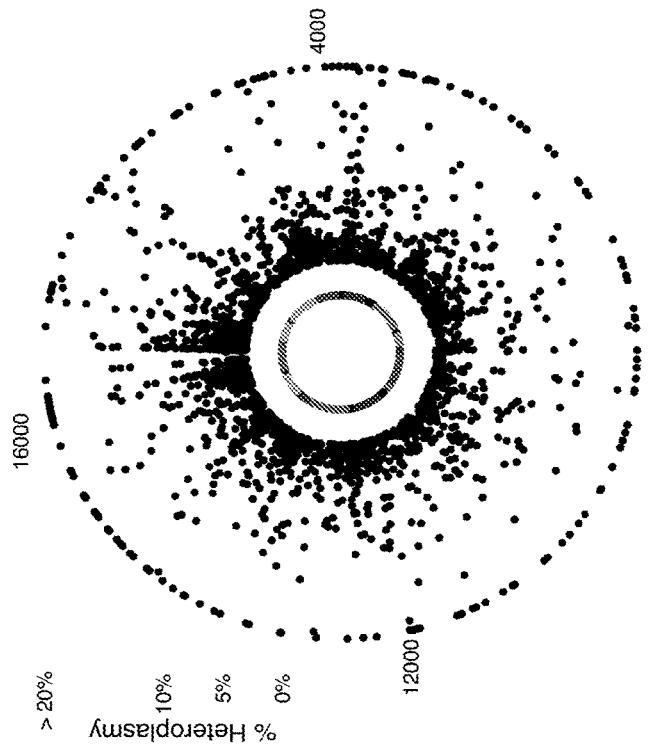
Figure 6E:
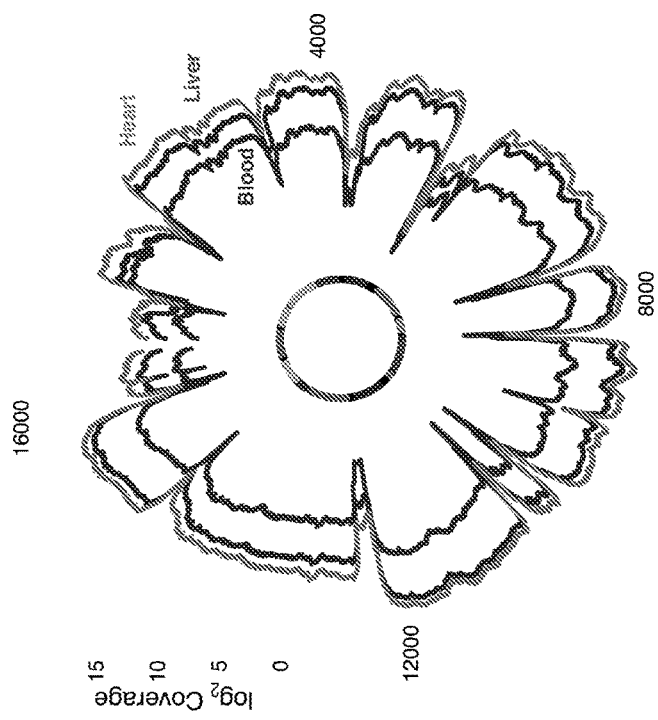
Figure 6D:
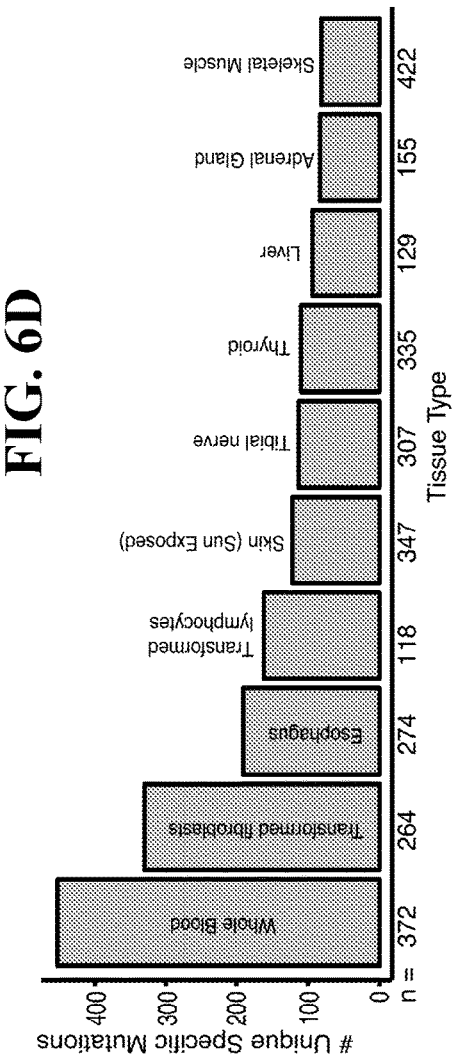
Figure 6F:
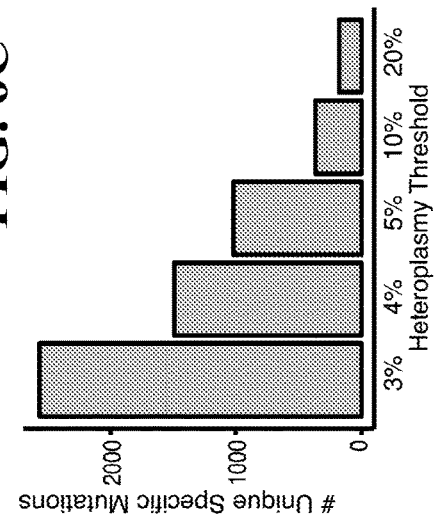

To assess the broader applicability of the approach, Applicants examined putative mitochondrial "barcodes" across diverse human tissues, similar to previous studies that have shown widespread inter- and intra-individual diversity of heteroplasmic mtDNA mutations (20, 21). Applicants analyzed mitochondrial genotypes based on over 424.2 billion aligned bulk RNA-seq reads from 8,820 individual samples in the GTEx project (41), spanning 49 tissues with at least 25 donors and 462 donors with at least 10 tissues (FIG. 6A, table S3, SOM). There was significant variation in the proportion of mitochondrial reads mapping to the mitochondrial transcriptome across tissues, consistent with known differences in the absolute numbers of mitochondria and levels of mitochondrial gene expression in each tissue (FIG. 6B,C; FIG. 12A). After stringent filtering to remove artifacts related to RNA-seq (SOM), Applicants identified 2,762 mutations that were tissue-specific within an individual donor at a minimum of 3% heteroplasmy (FIG. 6D,E, FIG. 12B; table S4), revealing a diverse spectrum of mutations similar to previous reports (20, 21). Importantly, each of the 49 tissues examined had at least one tissue specific mutation from the aggregated samples. Moreover, only 28 non-polymorphic mutations were shared between any two tissues (minimum heteroplasmy of 5%), and no non-polymorphic mutations were shared between three tissues from any one donor, indicating that these mutations arose somatically and in a tissue-specific manner. Importantly, these are likely underestimates of the extent of heteroplasmy at the level of individual cells, due to the bulk measurements (19). Among the observed mutations, most of the predicted deleterious mutations (196-308, SOM) did not show an appreciable difference in median heteroplasmy compared to the benign ones (FIG. 12C,D), but a minority (17-25) were present only at >20% heteroplasmy (FIG. 12E,F), ~3.6- to 4.4-fold fewer than expected given the distribution of predicted benign variants. Thus, even damaging mutations may be tolerated at a heteroplasmy lower than estimated biochemical thresholds (60-90%) (24). This diversity of mitochondrial mutations within individual humans clearly indicates that these can be leveraged to probe questions related to cell lineage and cellular relationships across a range of tissues and cell types.

Example 9—Discussion

Collectively, Applicants have shown that somatic mtDNA mutations with levels as low as 5% heteroplasmy can be stably propagated in primary cells and can serve as clonal markers for lineage tracing applications in primary human cells (FIG. 3I). Additionally, Applicants show that variants at 0.5% heteroplasmy in a complex mixture are useful to infer clonality (FIG. 4C). Applicants have shown that mtDNA mutations are readily detected by commonly used scRNA-seq and scATAC-seq technologies that concomitantly provide cell state readouts from the same single cell. Moreover, Applicants propose a generalized framework where Applicants use a DNA-based bulk sample as a scaffold to substantially improve accuracy and mutation detection in RNA-based measurements. Importantly, mtDNA mutational profiles allow for unsupervised and unbiased identification of lineal relationships and clonal origins. Overall, the approach is far more scalable than current single cell whole genome sequencing approaches. For example, Applicants experimentally processed 520 cells (FIG. 4), resulting in 811,000,000 38 bp paired-end reads. The equivalent amount of sequencing would yield 10-fold coverage of the nuclear genome of a single cell, which, based upon current gold standard single cell whole genome sequencing studies, is not sufficient for confident mutation calling (8). Stated another way, ~18,000 individual cells' mitochondrial genomes can be sequenced at 100-fold coverage for the sequencing cost of a single nuclear genome at 10-fold coverage.

In addition to applying prevalent scRNA-seq and scATAC-seq techniques to measure mtDNA mutations, Applicants developed a scMito-seq protocol that could be used in combination with scRNA-seq, analogous to single cell whole genome and transcriptome sequencing, that provides higher coverage and higher fidelity of mitochondrial mutation detection (42). The protocol is based on rolling-circle amplification to minimize error propagation and is thus ideally suited for reliable mutation calling (30). Moreover, mitochondrial DNA sequencing based approaches could be combined with nuclear DNA sequencing strategies to detect SNVs, CNVs, and microsatellites and a combination of these approaches could significantly increase the fidelity and reach of single cell lineage tracing applications.

One potential limitation with using mtDNA mutations for lineage tracing may arise from the horizontal transfer of mitochondria between cells, which has been described in specific contexts, but the extent and physiologic relevance of such a process remains unclear. The transfer of organelles appears to be primarily triggered by various stress responses, is restricted to specific cell types such as mesenchymal stem/stromal cells and their recipients, and can be a feature of malignant cells, but the extent of organelle transfer appears to be limited (43-47). Applicants investigated the possibility of horizontal transfer, but were unable to detect evidence in the data (FIG. 4E) or in the CML dataset (FIG. 5D,E). Chimerism analysis following HSCT also showed no evidence of mtDNA variation from the host to the 1,073 sampled donor cells (FIG. 5G), indicating that there is limited, if any, detectable horizontal transfer of mtDNA between cells in the tested setting in vivo. Moreover, such transfer would have to be extensive to significantly confound analysis and results (FIG. 11F).

In conclusion, Applicants suggest that measuring somatic mitochondrial mutations provides a powerful and scalable method to perform lineage tracing studies in humans. Coupling these mitochondrial mutation readouts with single cell measurements of gene expression or chromatin accessibility provide a potent means to infer lineal relationships of stem and progenitor cells and their differentiated counterparts and to probe the molecular circuits that underlie cell fate decisions in health and disease. In total, lineage tracing using mitochondrial mutations could be used to infer critically needed lineal relationships in large-scale efforts, such as the Human Cell Atlas, to better understand the mechanics of homeostasis and development across a reference map of human tissues (48).

Example 10—Materials and Methods

ATAC-seq. For ATAC-seq library preparations 5,000-10,000 cells were washed in PBS, pelleted by centrifugation and forwarded to lysis and tagmentation in 1×TD buffer, 2.5 µl Tn5 (Illumina®), 0.1% NP40™ detergent, 0.3×PBS in a 50 µl reaction volume as described (M. R. Corces et al., An improved ATAC-seq protocol reduces background and enables interrogation of frozen tissues. Nat Methods 14, 959-962 (2017)). Samples were incubated at 37 C for 30 min at 300 rpm. Tagmented DNA was purified using the MinElute PCR kit (Qiagen®). The complete eluate was forwarded to PCR. After initial extension, 5 cycles of pre-amplification using indexed primers and NEBNext® High-Fidelity 2×PCR Master Mix (NEB®) were conducted, before the number of additional cycles was assessed by quantitative PCR using SYBR Green. Typically, 5-8 additional cycles were run. The final library was purified using a MinElute PCR kit (Qiagen®) and quantified using a Qubit dsDNA HS Assay kit (Invitrogen®) and a High Sensitivity DNA chip run on a Bioanalyzer 2100 system (Agilent®).

Single cell ATAC-seq. The C1 Fluidigm platform using C1 single cell Auto Prep IFC for Open App and Open App Reagent Kit were used for the preparation of single cell ATAC-seq libraries as previously described (J. D. Buenrostro et al., Single-cell chromatin accessibility reveals principles of regulatory variation. Nature 523, 486-490 (2015)). Briefly, cells were washed and loaded at 350 cells/µl. Successful cell capture was monitored using a bright-field Nikon microscope and was typically >85%. Lysis and tagmentation reaction and 8 cycles of PCR were run on chip, followed by 13 cycles off chip using custom index primers and NEBNext® High-Fidelity 2×PCR Master Mix (NEB®). Individual libraries were pooled and purified using the MinElute PCR kit (Qiagen®) and quantified using a Qubit dsDNA HS Assay kit (Invitrogen®) and a High Sensitivity DNA chip run on a Bioanalyzer 2100 system (Agilent®).

RNA-seq. Cells were lysed in RLT or TCL lysis buffer (Qiagen®) supplemented with beta-Mercaptoethanol and RNA was isolated using a RNeasy Micro kit (Qiagen®) according to the manufacture's instructions. An on-column DNase digestion was performed before RNA was quantified using a Qubit RNA HS Assay kit (Invitrogen®). 1-10 ng of RNA were forwarded to a modified Smart-seq2 protocol and after reverse transcription, 8 cycles of PCR were used to amplify transcriptome library (S. Picelli et al., Full-length RNA-seq from single cells using Smart-seq2. Nat Protoc 9, 171-181 (2014)). Quality of whole transcriptome libraries were validated using a High Sensitivity DNA Chip run on a Bioanalyzer 2100 system (Agilent®), followed by library preparation using the Nextera XT kit (Illumina®) and custom index primers according to the manufacturer's instructions. Final libraries were quantified using a Qubit dsDNA HS Assay kit (Invitrogen®) and a High Sensitivity DNA chip run on a Bioanalyzer 2100 system (Agilent®).

Single cell sorting. Single cells were sorted into 96 well plates using the Sony SH800 sorter using a 100 µm chip at the Broad Institute Flow Cytometry Facility. Sytox Blue (Invitrogen) was used for live/dead cell discrimination. For single cell RNA-seq, plates were spun immediately after sorting and frozen on dry ice and stored at −80 C until further processing.

Single cell RNA-seq. Single cells were sorted into 5 ul TCL lysis buffer (Qiagen®) supplemented with 1% beta-Mercaptoethanol. RNA isolation, reverse transcription and PCR were conducted as described using a modified Smart-seq 2 protocol (S. Picelli et al.; and A. C. Villani et al., Single-cell RNA-seq reveals new types of human blood dendritic cells, monocytes, and progenitors. Science 356, (2017)). Quality control and library preparation were conducted as described above.

Single cell Mito-seq. Single cells were sorted in to 5 ul TCL lysis buffer (Qiagen®) supplemented with 1% beta-mercaptoethanol. DNA was isolated with AMPure XP beads (Beckman Coulter®) and the REPLI-g Mitochondrial DNA kit (Qiagen®) was used for amplification at 33 C for 8 h in a 16.5 ul reaction volume. Amplified DNA was cleaned up with AMPure XP beads (Beckman Coulter®), quantified using a Qubit dsDNA HS Assay kit (Invitrogen) and library preparation was performed using the Nextera XT kit (Illumina®) using custom index primers according to the manufacturer's instructions.

Sequencing. All libraries were sequenced using Nextseq High Output Cartridge kits and a Nextseq 500 sequencer (Illumina®). Libraries were sequenced paired-end (2×38 or 2×75 cycles).

Cell culture and Methylcellulose colony assays. TF1 cells were cultured in RPMI, 10% FBS, 2 mM L-Glutamine and 2 ng/ml GM-CSF (Peprotech®) at 37 C and 5% $CO_2$. CD34+ hematopoietic stem and progenitor cells were obtained from the Fred Hutch and Hematopoietic Cell Processing and Repository (Seattle, USA) and were cultured in Stemspan II with 1×CC100 (Stemcell Technologies®) at 37 C and 5% $CO_2$. For methylcellulose colony assays 500 cells per ml were plated in MethoCult H4034 Optimum (Stemcell Technologies®) according to the manufacturer's instructions. Individual colonies were picked at day 10 or 12 after plating and forwarded to single cell sorting as described above.

Data processing and read alignment. For each next-generation sequencing library generated for this study (FIG. 1, FIG. 2D-H, FIG. 3, and FIG. 4), libraries were consistently sequenced on the Illumina Next-Seq and demultiplexed using the bcl2fastq program. For each library, raw .fastq reads were consistently aligned using either Bowtie2 version 2.3.3 (ATAC-seq and Mito-seq) (B. Langmead, S. L. Salzberg, Fast gapped-read alignment with Bowtie 2. Nat Methods 9, 357-359 (2012)) or STAR version 2.5.1b (RNA-seq) (A. Dobin et al., STAR: ultrafast universal RNA-seq aligner. Bioinformatics 29, 15-21 (2013)) to the hg19 reference genome. For the mESC scRNA-seq coverage comparison (FIG. 2A), reads were aligned to the mm10 reference genome. RNA-seq and scRNA-seq transcriptome counts were computed using STAR's "—quantModes GeneCounts" flag using the Gencode 19 release .gtf file. For the 10× AML dataset (G. X. Zheng et al., Massively parallel digital transcriptional profiling of single cells. Nat Commun 8, 14049 (2017)), processed .bam files (aligned to GRCh37) were downloaded from the public downloads page on the 10× website.

Public RNA-seq and scRNA-seq data were downloaded from the Gene Expression Omnibus (GEO), European Nucleotide Archieve (ENA), or the database of Genotypes and Phenotypes (dbGaP) resources. Specifically, raw .fastq files for each experiment were downloaded from the following accessions:

TABLE S1

Description of public datasets analyzed in this manuscript.

| Dataset | Resource | Accession | FIGURE (S) |
|---|---|---|---|
| mESC scRNA-seq | GEO | GSE75790 | FIG. 2A |
| SIDR scDNA/RNA-seq | ENA | PRJEB20143 | FIG. 2B |
| CML scRNA-seq | GEO | GSE76312 | FIG. 5A-E |
| AML scRNA-seq | 10X Genomics | 10X Website (Public) | FIG. 5G |
| GTEx | dbGAP | phs000424.v7.p2 | FIG. 6 |

Only previously aligned and processed data for the AML 10× data was downloaded in the .bam format.

Mitochondrial Genotyping. For each next-generation sequencing sample, per-base, per-allele counts were determined using a custom python script that imported aligned .bam files using the pysam (github.com/pysam-developers/pysam) module. Raw reads were filtered such that they had an alignment quality of 30 and were uniquely mapping to only the mitochondrial genome. Moreover, the mean base-quality score was computed per-base, per-allele for each sample for quality control. At a given mitochondrial genome position x, the allele frequency (AF) of a base b could be computed using the number of reads R supporting that particular base at position x:

$$AF_{x,b} = \frac{R_b}{\sum_{b \in \{A,C,G,T\}} R_b}$$

Applicants note that the coverage of a given position x is defined by the denominator of this previous expression, $\sum_{b \in \{A,C,G,T\}} R_b$.

Variant quality control and filtering. To remove variants whose heteroplasmy may largely be driven by sequencing errors, Applicants examined the distribution of per-base, per-allele base-quality scores, noting a clear pattern of high quality and low-quality variants (FIG. 7C). To determine high quality variants, Applicants fit a mixture of three Gaussian distributions (noted by the colors), and filtered such that only variant/alleles that had >99% probability of belonging to the blue (largest mean BQ) Gaussian were retained. This conservative empirical threshold (shown in the blue dotted line on FIG. 7C) for a BQ cutoff was determined to be 23.8 based on this mixture model approach.

As one poorly quantified position allele would affect the estimates for all other alleles at the specific position, Applicants filtered positions that contained one or more alleles with a BQ less than the empirical threshold unless the allele had a non-significant (i.e. less than 1 in 500) effect on the heteroplasmy. In total, Applicants called 44 high-quality variants across the TF1 (sub-)clones (FIG. 7G) that were present at a minimum of 2.5% heteroplasmy in at least one sample. Applicants note that throughout the study, Applicants observed a preponderance of C>T, T>C, G>A, and A>G mutations (transitions), consistent with previous reports.

Mitochondrial distance. As an input to the variance components models used in this paper (FIG. 1G, 4F), Applicants computed a mitochondrial relatedness matrix $K_{mito}$, which is defined as $K_{mito}=1-D$, where D is a symmetric, pairwise distance matrix whose elements encode the distance between pairs of cells or clones based on the differences in allele frequencies. Applicants define this matrix D for pairs of observations i,j over high-quality variants $x \in X$ using the matrix of allele frequencies (AF) and coverage frequencies (C) such that only variants sufficiently well-covered (minimum # of reads at the position is greater than 100). Explicitly, Applicants define the mitochondrial distance between observations i,j using the distance $d_{i,j}$ as follows:

$$d_{i,j} = \frac{\sum_x \sqrt{|AF_{x,i} - AF_{x,j}|} * (1_{C_{x,i}>100} * 1_{C_{x,j}>100})}{\sum_x (1_{C_{x,i}>100} * 1_{C_{x,j}>100})}$$

where 1 is the indicator function. Intuitively, this representation of mitochondrial distance simultaneously accounts for variation in rare heteroplasmy (through the square root transformation) and only compares high-confidence variants between pairs of cells. For the bulk ATAC-seq of TF1 (sub-)clones analyzed in FIG. 1, all quality-controlled variants passed the coverage requirement; however, the additional indicator functions for coverage were necessary for single cells examined later in the manuscript. Moreover, the mitochondrial distance matrix computed on this metric served as the input to the hierarchical clustering that was used to cluster the TF1 lineage in an unsupervised manner.

Applicants note that while an ideal tree reconstruction algorithm would facilitate the inclusion of internal nodes, Applicants found no such algorithms readily available as most tree reconstruction approaches do not allow for internal observations.

Variance components model. To determine the proportion of the variance of chromatin accessibility that could be explained by the mitochondrial lineage in each peak, Applicants performed a variance decomposition using a random effects model shown in FIG. 1H. Briefly, the chromatin accessibility counts measured from ATAC-seq for 91,607 accessibility peaks were summed, centered, and scaled for each sample. Applicants then estimated the proportion of variance explained due to the random variance component ($\sigma_e^2$) and the variance component from the sample-sample structure inferred by the mitochondrial genotype ($\sigma_m^2$) for each peak using average information restricted maximum likelihood (AIREML). Explicitly, the model for the variance of chromatin accessibility account for an individual peak is:

Peak Accessibility~$N(0, \sigma_m^2 K_{mito} + \sigma_e^2 I)$ and the proportion of the variance explained by the mitochondrial structure then is the ratio of $\sigma_m^2$ over the total variation:

$$\frac{\sigma_m^2}{\sigma_m^2 + \sigma_e^2}$$

The proportion of the variance explained by the mtDNA mutation substructure is shown for each peak in FIG. 7E alongside an analogous calculation, where the substructure is only defined by a binary indicator of clonal membership for pairs of samples.

Most common recent ancestor analysis. To determine the accuracy of mitochondrial mutations reconstructing the experimental lineage in FIG. 1, Applicants determined the proportion of correctly identified most-recent common ancestors (MRCA) for trios of (sub-)clones, similar to what has recently been reported by Biezuner et al. (T. Biezuner et al., A generic, cost-effective, and scalable cell lineage analysis platform. *Genome Res* 26, 1588-1599 (2016)). For any given set of three samples in the predicted tree (e.g. A, C, and D; see FIG. 7H), three possible arrangements are possible: 1) A and C share an MRCA compared to D; 2) C and D share an MRCA compared to A; or 3) A and D share an MRCA compared to C. Given the true experimental lineage tree (in this example, arrangement 2), Applicants determined whether or not the reconstructed lineage correctly identified the MRCA. Thus, by chance, a random tree reconstruction would be 33% accurate. Here, Applicants segregate comparisons within-clone (e.g. B,C,D in FIG. 7H) or between clone (e.g. A,C,D) and demonstrate that the tree reconstruction significantly outperforms what one would expect due to chance in both settings.

Clonal mixture deconvolution (TF1 clones). As the previous analyses verified that mitochondrial mutations could reconstruct the known experimental lineage, Applicants sought to further demonstrate that convolutions of clones could be determined using mitochondrial mutations. To achieve this, Applicants mixed the second-generation clones in known proportions and sought to retrospectively infer these proportions from the genotype of the mixture. For two known mixture fractions (FIG. 7F), Applicants genotyped each mixed sample with bulk ATAC-seq and then used the second-generation allele frequencies to infer each mixture. To achieve this, Applicants fit a support vector regression model to estimate the mixing proportions as analogously implemented in CIBERSORT (A. M. Newman et al., Robust enumeration of cell subsets from tissue expression profiles. *Nat Methods* 12, 453-457 (2015)). As shown in FIG. 7F, the average deviation of the inferred and true mixing proportions are 1.7% and 3.0%, demonstrating that a priori defined genotypes can be used to approximate the contributions of complex mixtures.

Comparison of single-cell technologies (mESC; SIDR). To compare mitochondrial coverage of various scRNA-seq platforms, Applicants downloaded 583 consistently examined mouse embryonic stem cell (mESC) samples (C. Ziegenhain et al., Comparative Analysis of Single-Cell RNA Sequencing Methods. *Mol Cell* 65, 631-643 e634 (2017)). Reads were aligned to the mm10 reference genome using STAR. Per-base pair coverage estimates were computed for each single cell using reads uniquely mapping to the mitochondrial genome.

To verify that heteroplasmic variants were expressed at a comparable frequency as these heteroplasmies in DNA, Applicants downloaded 38 high-quality single cells where both mitochondrial genome and transcriptome were available (K. Y. Han et al., SIDR: simultaneous isolation and parallel sequencing of genomic DNA and total RNA from single cells. *Genome Res* 28, 75-87 (2018)). Reads from mtDNA and RNA were aligned using bowtie2 and STAR respectively as described above to the hg19 reference genome and heteroplasmic allele frequencies were plotted for variants with at least 50 reads covering the locus in both RNA and DNA both with a minimum BQ score of 20 in the same cell.

Comparison of single-cell technologies (TF1 clones). Applicants hypothesized that the amalgamation of single cells across different technologies would reproduce bulk allele frequencies across these TF1 clones. Thus, to compare single cell technologies to the bulk, Applicants summed all raw allele counts for high-quality cells (minimum of 100× mitochondrial genome coverage). For nine characterized, clone-specific heteroplamsic variants (FIG. 8F) as well as variants identified as RNA-specific (FIG. 2D), Applicants plotted the allele frequency comparing the two technologies for heteroplasmic variants, revealing concordance across all the technologies (FIG. 8E).

Dimensionality reduction of hematopoietic colonies using mRNA expression profiles and mitochondrial genotypes. In order to contrast the information encoded in the mitochondrial genotypes to the mRNA expression profiles (FIG. 3B-G), Applicants performed a t-stochastic neighbor embedding (t-SNE) of both datasets per cell. First, Applicants identified a set of 935 high quality cells that 1) detect at least 500 genes, 2) had a total count of at least 2000 across expressed genes, and 3) had a mean mitochondrial genome coverage of at least 100. For the gene expression dimensionality reduction, Applicants first batch-corrected a log counts-per-million matrix of gene expression values using sva (J. T. Leek, W. E. Johnson, H. S. Parker, A. E. Jaffe, J. D. Storey, The sva package for removing batch effects and other unwanted variation in high-throughput experiments. *Bioinformatics* 28, 882-883 (2012)) and used the top 10 principal components for the t-SNE. For the mitochondria analysis, Applicants used all variants with a mean BQ score of 25 present at a heteroplasmy of at least 0.5% in the population of cells and similarly computed t-SNE coordinates using the top 10 principal components of the heteroplasmy matrix. Applicants note that Applicants observed no significant batch effect in the mitochondrial allele frequencies.

Identification of colony and cell-specific mutations in hematopoietic cells. To identify mutations that could effectively separate colonies in donors 1 and 2 (FIG. 3, FIG. 9), Applicants identified mutations present at a minimum of 80% of cells within a colony at a minimum heteroplasmy of 5%. Moreover, Applicants required for these mutations, which Applicants denoted as "colony separating", to not be present at greater than 5% heteroplasmy in more than two cells from separate colonies.

For determining mutations that could separate bulk ATAC colonies (donor 3 and 4), Applicants identified mutations that were present at a heteroplasmy >5% in a particular colony but absent (<0.5%) in all other colonies. A similar logic was used to identify cell-specific mutations in FACS-sorted HSCs (donors 5, 6, and 7), where Applicants identified mutations that were present at >5% heteroplasmy for a particular cell but otherwise absent (<0.5%) in all other cells for a specific donor.

Separation of clonal mixtures of CD34+ HSPCs. For the separation of CD34+ HSPCs shown in FIG. 4, Applicants identified 16 high quality variants for scATAC (FIG. 10A) and 14 for scRNA-seq (FIG. 4C) that had a mean BQ score of at least 20 for both the sum of single cells and the bulk ATAC seq (FIG. 4B). Moreover, Applicants considered variants detected in bulk at a heteroplasmy of at least 0.5%, leading to the number of variants noted above.

Figure 4G:
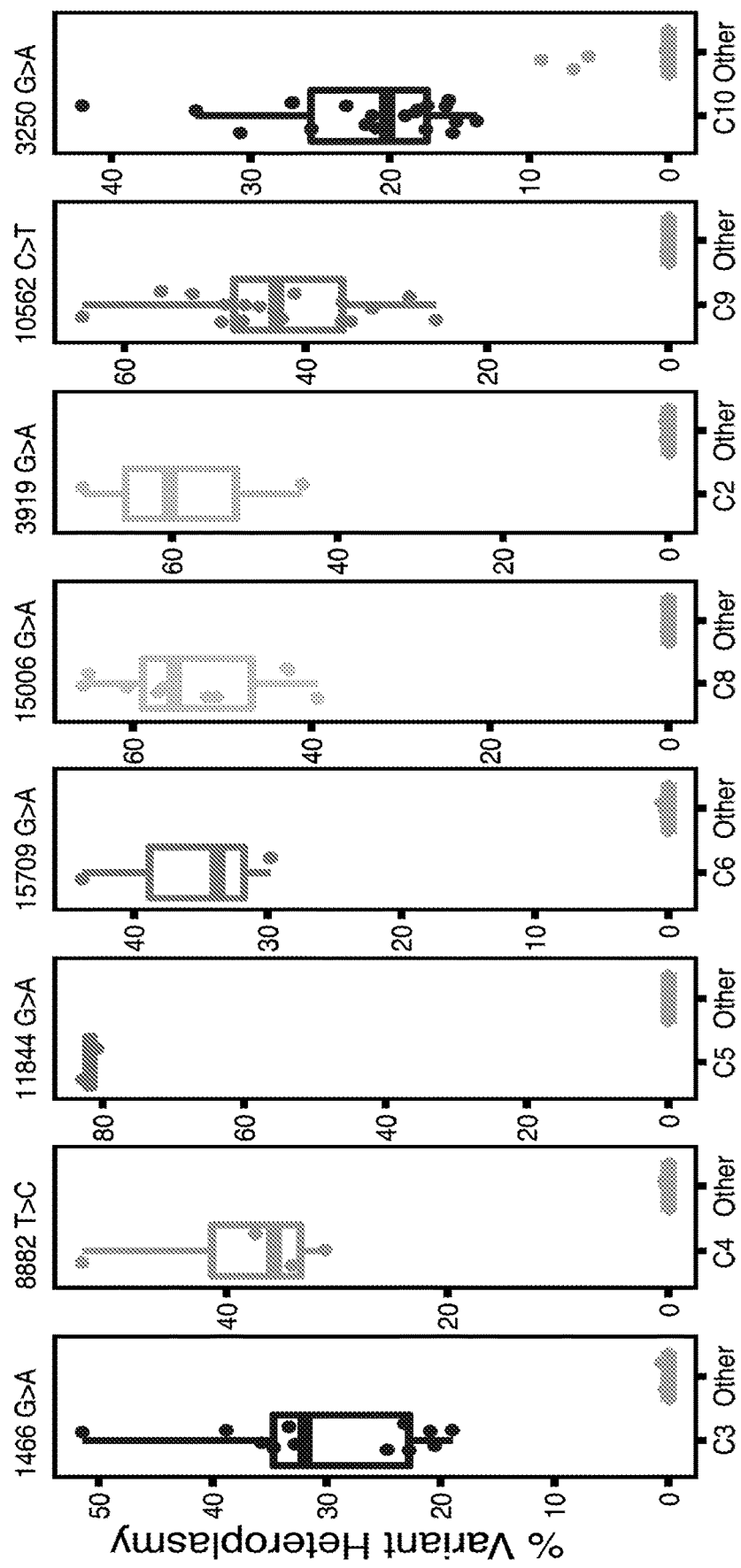

Using these variants and cells passing filter (minimum average mitochondrial genome coverage of 100×), Applicants performed a fuzzy k-mediods clustering and assigned cells to clusters that has an assignment probability greater than 95%. Applicants identified 9 clusters for scATAC and 10 for scRNA that corresponded directly to one or more mutations (FIG. 4D, E). While other cells showed evidence of mutations, these occurred at lower heteroplasmy values than the frequencies for cells assigned to the group (FIG. 4G).

Simulated Density of Assignment. To verify that the probabilistic cluster was within the range of expectation, Applicants performed a simulation study by parameterizing attributions of the mixing experiment (FIG. 10 B, C). Specifically, for each of the 30 input CD34+ cells, Applicants simulated a proportion of the specific cell in the final population $p_i$, $i \in \{1, \ldots, 30\}$, using a Beta distribution:

$$p_i \sim \text{Beta}(1,29)$$

In expectation, the proportion in the terminal cell populations would be 1/30, consistent with the expectation of the draw from the Beta distribution. From this vector of population proportions p, Applicants simulate the number of cells N sampled from the single-cell sampling using a multinomial distribution:

$$n \sim \text{Multinomial}(N,p)$$

where N=372,148 for the single-cell RNA and single-cell ATAC, respectively. Thus, $n_i$ represents the number of cells that were derived from a single original cell i. Next, Applicants simulated whether cell i contained a mutation that could be detected and clustered in a group of cells (r=1). This was achieved using a Bernoulli draw for each cell:

$$r_i = \text{Bern}(1,q)$$

where q was estimated to be 0.5 based on the analyses in FIG. 3 for scRNA-seq. Finally, the total number of cells clustered (c, the unit shown on FIG. 10B, C) is computed from the following:

$$c = \sum_{i=1}^{30} r_i * n_i$$

For both scATAC and scRNA, Applicants computed c over 10,000 simulations each. The observed number of cells clustered in FIG. 4D,E fell comfortably within the 95% coverage interval for both ATAC and RNA (FIG. 10B, C), demonstrating the efficacy of the probabilistic clustering approach.

Dimensionality reduction of public CML single cell RNA-seq data. As Applicants determined that using variants determined by scRNA-seq in the absence of a bulk DNA guide lead to spurious mutations (FIG. 10F), Applicants hypothesized that using a more stringent measure of quality, base alignment quality (BAQ) (H. Li, Improving SNP discovery by base alignment quality. *Bioinformatics* 27, 1157-1158 (2011)), could facilitate the identification of fewer high-quality variants that could be used in the absence of bulk reference. Indeed, Applicants identified 242 high-quality variants that had a minimum BAQ score greater than 20 with a mean heteroplasmy of 0.5% in the population of high quality cells that (minimum mean mitochondrial genome coverage of 100×). Applicants performed a t-SNE on the first 25 principal components from the z-score normalized heteroplasmy matrix, again using the default parameters (perplexity=30). To identify variants that segregated with patient sub-phenotypes, Applicants again employed a Mann-Whitney U-Test to identify variants that co-varied with an annotation at a significance of $p < 10^{-3}$ within a given donor.

Analysis of CML transcriptomic data. Clustering of the single-cell CML transcriptomic data for donor CML656 was performed using SC3 (V. Y. Kiselev et al., SC3: consensus clustering of single-cell RNA-seq data. *Nat Methods* 14, 483-486 (2017)) on processed RNA-seq data values available through the GEO accession GSE76312. SC3 was run using the default parameters for clusters of size 2, 3, and 4. The 29 samples identified in cluster 1 were consistently re-processed using STAR (Dobin et al.) using parameters noted above before differential expression was performed using limma-voom (C. W. Law, Y. Chen, W. Shi, G. K. Smyth, voom: Precision weights unlock linear model analysis tools for RNA-seq read counts. *Genome Biol* 15, R29 (2014)). The lowest non-zero allele frequency of 4824 T>C for a cell in cluster 1 was 4%, providing a clear basis for determining cells that were 4824 T>C+(that is, any cell with a non-zero allele frequency for 4824 T>C were considered 4824 T>C+). In total, 14 cells in cluster 1 were negative for the mutation whereas 15 were positive, which served for the basis of differential gene expression between the cluster 1 sub-clones.

Preprocessing 10×AML Dataset. For the AML datasets previously generated by 10×Genomics (Zheng et al.), cells from two patients before and after undergoing hematopoietic stem cell transplantation (AML027 and AML035) were profiled for mitochondrial genotypes. Aligned and processed .bam files were downloaded from the publicly available 10× website (support.10xgenomics.com/single-cell-gene-expression/datasets/) and further processed using custom python scripts. Barcodes containing at least 200 reads uniquely aligning to the mitochondrial genome for all samples were considered for downstream analysis. Barcodes were further filtered based on coverage at two specific variants that were covered by at least one read. Applicants note that Applicants did not observe a barcode that contained a read to support both alternate alleles (3010G>A and 9698T>C). Applicants determined that 4 out of 1,077 cells were derived from the recipient (FIG. 5G). This estimate was higher than an analogous analysis performed using nuclear genome variants previously described (reported exactly 0% (Zheng et al.)) though Applicants note that these four cells did not pass the transcriptome filter employed in the original 10× analysis. Moreover, Applicants did not observe a well-covered set of variants separating the donor/recipient pair in the AML027 dataset. Thus, this sample was not further analyzed for mutations and only used for determining well-covered barcodes (FIG. 11D, E).

GTEx analyses. Raw .fastq files were downloaded from dbGAP as noted above for nearly 10,000 samples consistently sequenced on the Illumina Hi-Seq with 75 bp paired-end reads. After filtering for samples using criteria noted in FIG. 6A (sample belonging to one of 49 tissues that had at least 25 total samples; individual with at least 10 tissues; and mean mitochondrial genome coverage of 1000×), Applicants considered 8,820 samples for downstream analysis. Applicants define a "tissue specific mutation" (FIG. 3D, F) for a given mitochondrial variant where the variant is present at least at 3% heteroplasmy (or more where indicated) in an individual tissue but no more than 0.5% (within the margin of error for bulk RNA-seq) in any of the other tissues for a specific donor. Applicants further filtered mutations that occurred more than 10 times within a given tissue to exclude the possibility of tissue-specific mitochondrial RNA-editing events. While the noise in the RNA-seq assay inherently leads to more false positives and less certainty in the heteroplasmy estimation, the procedure of comparing heteroplamsic values against other tissues within a donor provides a conservative means toward identifying putative somatic mutations that arose during development or homeostasis. To compute the expected number of pathogenic and damaging mutations (FIG. 12E, F), Applicants multiplied the number of loci that were observed above a defined heteroplasmy threshold (e.g. 20%) by the rate at which damaging or pathogenic mutations occur in the mitochondrial genome.

Example 11—Nuclei Isolation Protocol to Enhance mtDNA Yield

In certain embodiments, the methods of the present invention can be performed using single nuclei. Methods of isolating nuclei for single cell sequencing are known in the art (see, e.g., 10× Genomic protocols: "Nuclei Isolation for Single Cell ATAC Sequencing" CG000169 Rev A; and "Chromium Single Cell ATAC Reagent Kits" CG000168 Rev A). However, the protocols are not designed for enhanced mtDNA yield.

Applicants have developed a nuclei isolation protocol that allows sequencing of mitochondrial DNA from single cells. The protocol is based on 10× protocol "Nuclei Isolation for Single Cell ATAC Sequencing" CG000169 Rev A and 10× protocol "Chromium Single Cell ATAC Reagent Kits" CG000168 Rev A. Nuclei may be used with single-cell RNA (scRNA-seq) or assay for transposase accessible chromatin (scATAC-seq) sequencing as described herein. The basic protocol is described below followed by modifications:

I. Nuclei Isolation
1. Thaw Cells
  (For fresh cells, wash cells with PBS+0.04% BSA, determine cell count, and proceed to Nuclei Isolation)
  Based on cell type, thaw cells using the protocol for thawing cell lines or primary cells/fragile cells
  Resuspend cell pellet
  (in 1 ml PBS+0.04% BSA)
  Determine cell concentration
2. Nuclei Isolation
  Add cell suspension to 2-ml tube
  Centrifuge (300 rcf, 5 min) Remove Supernatant
  Add Lysis Buffer to pellet (Pipette mix)
  Incubate on ice (3-5 min*) *Optimize time for complete cell lysis
  Add Wash Buffer (Pipette mix)
  Centrifuge (500 rcf, 5 min) Remove Supernatant DO NOT disturb pellet
  Resuspend in Diluted Nuclei Buffer (Critical for optimal assay performance)
  Determine final nuclei concentration
3. Proceed to Chromium Single Cell ATAC Reagent Kits Protocol (CG000168)

Modifications Step 1: Fixation of cells. Fixation is critical to minimize crosstalk of mtDNA between different cells. After thawing and washing cells with PBS as described in the protocol, cells were first fixed with formaldehyde (methanol-free, Cat #28906, Thermo®). Exact volumes may vary, but final concentration of formaldehyde was 1%, final concentration of glycine was 0.125M. Fixation may also be performed with paraformaldehyde.

Use 1.5 ml Eppendorf DNA lobind tubes
Resuspend cell pellet in 450 ul PBS
add 30 ul 16% formaldehyde (1% Final)
Incubate 10 min at room temperature, swirl, invert occasionally
Quench by adding 26.775 ul glycine (2.36M->0.125M final)
Wash with 1×PBS (ice-cold) by filling up tube, invert 5 times
Spin at 400 g for 5 min at 4 C
Discard supernatant
Resuspend cell pellet in 1 ml 1×PBS (ice-cold)
Spin at 400 g for 5 min at 4 C
Discard supernatant Additional optimizations may include: assessing different formaldehyde concentrations (Applicants successfully tried 0.1% and 1% final concentrations with similar performance), assessing different crosslinking times, assessing different crosslinking reagents, and adjusting conditions depending on cell type.

Modifications Step 2: Lysis. Applicants followed the protocol as described but modified the lysis and wash buffer as follows: Lysis buffer only contained NP40™ detergent (Cat #28324, Thermo), but no Tween®-20 detergent or Digitonin detergent. The wash buffer contained no Tween®-20 detergent. This is critical because addition of Tween®-20 detergent will significantly deplete mtDNA. Additional optimizations may include: assessing different detergents, assessing different detergent concentrations, assessing different detergent combinations, assessing different wash buffer recipes, and adjusting conditions depending on cell type.

| Lysis buffer | Final |
|---|---|
| Tris-HCl (pH 7.5) | 10 mM |
| NaCl | 10 mM |
| MgCl2 | 3 mM |
| NP40 ™ detergent | 0.10% |
| BSA | 1% |

II. Single Cell ATAC
Step 1—Transposition
1.1 Prepare Transposition Mix
1.2 Isothermal Incubation
Step 2—GEM Generation and Barcoding
2.1 Prepare Master Mix
2.2 Load Chromium Chip E
2.3 Run the Chromium Controller
2.4 Transfer GEMs
2.5 GEM Incubation
Step 3—Post GEM Incubation Cleanup
3.1 Post GEM Incubation Cleanup—Dynabeads
3.2 Post GEM Incubation Cleanup—SPRIselect
Step 4—Library Construction
4.1 Sample Index PCR
4.2 Post Sample Index Double Sided Size Selection—SPRIselect
4.3 Post Library Construction QC Modifications ATAC: All steps up to the first PCR were identical as described in the 10× protocol (Chromium Single Cell ATAC Reagent Kits, CG000168 Rev A). Additional optimizations may include increasing Tn5 concentration during transposition because there is more DNA to be cut as more mtDNA is available (in particular at higher cell input concentrations).

PCR. As cells were fixed, one usually requires decrosslinking to break formaldehyde mediated covalent bonds between molecules for PCR of DNA. Usually this occurs through heating. Typical decrosslinking conditions (e.g. in Chromatin-immunoprecipitation-sequencing) are incubation of sample at 60 C overnight. Applicants assessed the following conditions prior to the regular PCR program (step 0 below).

| PCR program Step | Temperature | Time | | |
|---|---|---|---|---|
| 0 | 60° C. | 1 h | | |
| 1 | 72° C. | 0:05:00 | | |
| 2 | 98° C. | 0:00:30 | | |
| 3 | 98° C. | 0:00:10 | | |
| 4 | 59° C | 0:00:30 | | |
| 5 | 72° C. | 0:01:00 | | |
| | | Go to step 3, | repeat 11X | (Total 12 cycles) |
| 6 | 15° C. | Hold | | |

| Tested conditions (step 0) Temperature | Time |
|---|---|
| 60° C. | 1 h |
| 60° C. | 6 h |
| 60° C. | 12 h |

-continued

| Tested conditions (step 0) Temperature | Time |
|---|---|
| 72° C. | 1 h |
| 80° C. | 1 h |

Applicants noted that prolonged incubation at 60 C or 80 C resulted in reduction of library complexity (number of unique DNA molecules). Specifically, it appeared to primarily result in loss of smaller DNA fragments. These fragments likely denature more readily at 60 C and cannot be retrieved afterwards (e.g, due to the way the Tn5 transposase cuts). Applicants reasoned that the heating steps of the PCR may already be sufficient to enable decrosslinking and just conducted the regular PCR (no step 0). Indeed, this was sufficient. Extending step 1 to 15 min did not appear to affect library complexity.

In general, most optimizations were tested across different experiments (different cell types, input cell numbers). Additional optimizations should test similar input populations (same cell type and number). Additionally, different fixation reagents may require different PCR conditions (incubation steps, duration of steps).

REFERENCES

1. J. E. Sulston, H. R. Horvitz, Post-embryonic cell lineages of the nematode, Caenorhabditis elegans. Dev Biol 56, 110-156 (1977).
2. M. B. Woodworth, K. M. Girskis, C. A. Walsh, Building a lineage from single cells: genetic techniques for cell lineage tracking. Nat Rev Genet 18, 230-244 (2017).
3. J. Sun et al., Clonal dynamics of native haematopoiesis. Nature 514, 322-327 (2014).
4. V. W. Yu et al., Epigenetic Memory Underlies Cell-Autonomous Heterogeneous Behavior of Hematopoietic Stem Cells. Cell 167, 1310-1322 e1317 (2016).
5. W. Pei et al., Polylox barcoding reveals haematopoietic stem cell fates realized in vivo. Nature 548, 456-460 (2017).
6. A. McKenna et al., Whole-organism lineage tracing by combinatorial and cumulative genome editing. Science 353, aaf7907 (2016).
7. L. Biasco et al., In Vivo Tracking of Human Hematopoiesis Reveals Patterns of Clonal Dynamics during Early and Steady-State Reconstitution Phases. Cell Stem Cell 19, 107-119 (2016).
8. M. A. Lodato et al., Somatic mutation in single human neurons tracks developmental and transcriptional history. Science 350, 94-98 (2015).
9. Y. S. Ju et al., Somatic mutations reveal asymmetric cellular dynamics in the early human embryo. Nature 543, 714-718 (2017).
10. T. Biezuner et al., A generic, cost-effective, and scalable cell lineage analysis platform. Genome Res 26, 1588-1599 (2016).
11. K. Naxerova et al., Origins of lymphatic and distant metastases in human colorectal cancer. Science 357, 55-60 (2017).
12. L. Tao et al., A duplex MIPs-based biological-computational cell lineage discovery platform. BioRriv, (Oct. 14, 2017).

13. H. Zafar, A. Tzen, N. Navin, K. Chen, L. Nakhleh, SiFit: inferring tumor trees from single-cell sequencing data under finite-sites models. *Genome Biol* 18, 178 (2017).
14. T. Biezuner, O. Raz, S. Amir, L. Milo, R. Adar, Comparison of seven single cell Whole Genome Amplification commercial kits using targeted sequencing. *BioRxiv*, (Sep. 11, 2017).
15. W. K. Chu et al., Ultraaccurate genome sequencing and haplotyping of single human cells. *Proc Natl Acad Sci USA*, (2017).
16. R. W. Taylor et al., Mitochondrial DNA mutations in human colonic crypt stem cells. *J Clin Invest* 112, 1351-1360 (2003).
17. V. H. Teixeira et al., Stochastic homeostasis in human airway epithelium is achieved by neutral competition of basal cell progenitors. *Elife* 2, e00966 (2013).
18. Y. G. Yao et al., Accumulation of mtDNA variations in human single CD34+ cells from maternally related individuals: effects of aging and family genetic background. *Stem Cell Res* 10, 361-370 (2013).
19. E. Kang et al., Age-Related Accumulation of Somatic Mitochondrial DNA Mutations in Adult-Derived Human iPSCs. *Cell Stem Cell* 18, 625-636 (2016).
20. M. Li, R. Schroder, S. Ni, B. Madea, M. Stoneking, Extensive tissue-related and allele-related mtDNA heteroplasmy suggests positive selection for somatic mutations. *Proc Natl Acad Sci USA* 112, 2491-2496 (2015).
21. K. Ye, J. Lu, F. Ma, A. Keinan, Z. Gu, Extensive pathogenicity of mitochondrial heteroplasmy in healthy human individuals. *Proc Natl Acad Sci USA* 111, 10654-10659 (2014).
22. J. Morris et al., Pervasive within-Mitochondrion Single-Nucleotide Variant Heteroplasmy as Revealed by Single-Mitochondrion Sequencing. *Cell Rep* 21, 2706-2713 (2017).
23. V. I. Floros et al., Segregation of mitochondrial DNA heteroplasmy through a developmental genetic bottleneck in human embryos. *Nat Cell Biol* 20, 144-151 (2018).
24. J. B. Stewart, P. F. Chinnery, The dynamics of mitochondrial DNA heteroplasmy: implications for human health and disease. *Nat Rev Genet* 16, 530-542 (2015).
25. D. C. Wallace, D. Chalkia, Mitochondrial DNA genetics and the heteroplasmy conundrum in evolution and disease. *Cold Spring Harb Perspect Biol* 5, a021220 (2013).
26. J. L. Elson, D. C. Samuels, D. M. Turnbull, P. F. Chinnery, Random intracellular drift explains the clonal expansion of mitochondrial DNA mutations with age. *Am J Hum Genet* 68, 802-806 (2001).
27. M. R. Corces et al., An improved ATAC-seq protocol reduces background and enables interrogation of frozen tissues. *Nat Methods* 14, 959-962 (2017).
28. Y. Yuan et al., Comprehensive Molecular Characterization of Mitochondrial Genomes in Human Cancers. *BioRxiv*, (2017).
29. Y. S. Ju et al., Origins and functional consequences of somatic mitochondrial DNA mutations in human cancer. *Elife* 3, (2014).
30. T. Ni et al., MitoRCA-seq reveals unbalanced cytocine to thymine transition in Polg mutant mice. *Sci Rep* 5, 12049 (2015).
31. M. G. Filbin et al., Developmental and oncogenic programs in H3K27M gliomas dissected by single-cell RNA-seq. *Science* 360, 331-335 (2018).
32. A. S. Venteicher et al., Decoupling genetics, lineages, and microenvironment in IDH-mutant gliomas by single-cell RNA-seq. *Science* 355, (2017).
33. C. Ziegenhain et al., Comparative Analysis of Single-Cell RNA Sequencing Methods. *Mol Cell* 65, 631-643 e634 (2017).
34. K. Y. Han et al., SIDR: simultaneous isolation and parallel sequencing of genomic DNA and total RNA from single cells. *Genome Res* 28, 75-87 (2018).
35. D. Bar-Yaacov et al., RNA-DNA differences in human mitochondria restore ancestral form of 16S ribosomal RNA. *Genome Res* 23, 1789-1796 (2013).
36. J. D. Buenrostro et al., Single-cell epigenomics maps the continuous regulatory landscape of human hematopoietic differentiation. *BioRriv*, (Feb. 21, 2017).
37. A. Giustacchini et al., Single-cell transcriptomics uncovers distinct molecular signatures of stem cells in chronic myeloid leukemia. *Nat Med* 23, 692-702 (2017).
38. H. Gao et al., PDIA6 promotes the proliferation of HeLa cells through activating the Wnt/beta-catenin signaling pathway. *Oncotarget* 7, 53289-53298 (2016).
39. G. X. Zheng et al., Massively parallel digital transcriptional profiling of single cells. *Nat Commun* 8, 14049 (2017).
40. H. M. Kang et al., Multiplexed droplet single-cell RNA-sequencing using natural genetic variation. *Nat Biotechnol* 36, 89-94 (2018).
41. G. T. Consortium et al., Genetic effects on gene expression across human tissues. *Nature* 550, 204-213 (2017).
42. I. C. Macaulay et al., G&T-seq: parallel sequencing of single-cell genomes and transcriptomes. *Nat Methods* 12, 519-522 (2015).
43. D. Torralba, F. Baixauli, F. Sanchez-Madrid, Mitochondria Know No Boundaries: Mechanisms and Functions of Intercellular Mitochondrial Transfer. *Front Cell Dev Biol* 4, 107 (2016).
44. E. Griessinger, R. Moschoi, G. Biondani, J. F. Peyron, Mitochondrial Transfer in the Leukemia Microenvironment. *Trends Cancer* 3, 828-839 (2017).
45. C. R. Marlein et al., NADPH oxidase-2 derived superoxide drives mitochondrial transfer from bone marrow stromal cells to leukemic blasts. *Blood* 130, 1649-1660 (2017).
46. R. Moschoi et al., Protective mitochondrial transfer from bone marrow stromal cells to acute myeloid leukemic cells during chemotherapy. *Blood* 128, 253-264 (2016).
47. A. Caicedo et al., MitoCeption as a new tool to assess the effects of mesenchymal stem/stromal cell mitochondria on cancer cell metabolism and function. *Sci Rep* 5, 9073 (2015).
48. A. Regev et al., The Human Cell Atlas. *Elife* 6, (2017).

The invention is further described by the following numbered paragraphs:

1. A method of determining a lineage and/or clonal structure of single cells in a multicellular eukaryotic organism comprising:
   a) detecting mutations in mitochondrial genome sequencing reads of single cells obtained from a subject; and
   b) clustering the cells based on the presence of the mutations in the single cells, whereby a lineage and/or clonal structure for the single cells is retrospectively inferred.
2. The method of paragraph 1, wherein the method comprises sequencing the mitochondrial genomes in single cells obtained from the subject.
3. The method of paragraph 1 or 2, wherein the mutations in step (a) are detected in at least 5 sequencing reads and have at least 0.5% heteroplasmy in the single cells obtained from the subject.

4. The method of paragraph 3, wherein the mutations have at least 5% heteroplasmy in the single cells obtained from the subject.
5. The method of paragraph 1 or 2, further comprising detecting mutations in mitochondrial genome sequencing reads of a bulk sample obtained from the subject, wherein step (a) further comprises selecting heteroplasmic mutations detected in the bulk sample.
6. The method of paragraph 5, wherein the method comprises sequencing mitochondrial genomes in a bulk sample obtained from the subject.
7. The method of paragraph 6, wherein the bulk sequencing comprises DNA-seq, RNA-seq, ATAC-seq or RCA-seq.
8. The method of paragraph 7, wherein DNA-seq comprises whole genome, whole exome or targeted sequencing.
9. The method of any of paragraphs 5 to 8, wherein the selected mutations are detected in at least 5 sequencing reads and have at least 0.5% heteroplasmy in the bulk sample obtained from the subject.
10. The method of any of paragraphs 1 to 9, wherein the mutations are detected in the D loop of the mitochondrial genomes.
11. The method of any of paragraphs 1 to 10, further comprising detecting mutations in the nuclear genome and clustering the cells based on the presence of the mitochondrial and nuclear genome mutations in the single cells.
12. The method of paragraph 11, wherein the method comprises sequencing the nuclear genome in single cells obtained from the subject.
13. The method of any of paragraphs 1 to 12, wherein the detected mutations in step (a) have a Phred quality score greater than 20.
14. The method of any of paragraphs 1 to 13, wherein the clustering is hierarchical clustering.
15. The method of any of paragraphs 1 to 14, further comprising generating a lineage map.
16. The method of any of paragraphs 1 to 15, wherein detecting mutations in single cells comprises lysing the cells under conditions capable of lysing mitochondria.
17. The method of paragraph 16, wherein the lysing conditions comprise one or more of NP-40™ detergent, Triton X-100™ detergent, SDS, guanidine isothiocyanate, guanidine hydrochloride or guanidine thiocyanate].
18. The method of any of paragraphs 1 to 17, wherein detecting mutations in the mitochondrial genomes and/or nuclear genome of single cells comprises single cell RNA sequencing (scRNA-seq).
19. The method of paragraph 18, wherein detecting mutations in the mitochondrial genomes and/or nuclear genome comprises analyzing scRNA-seq data obtained from a subject.
20. The method of paragraphs 18 or 19, further comprising excluding RNA modifications, RNA transcription errors and/or RNA sequencing errors from the mutations detected.
21. The method of paragraph 20, wherein the RNA modifications comprise previously identified RNA modifications.
22. The method of paragraph 20, wherein RNA modifications, RNA transcription errors and/or RNA sequencing errors are determined by comparing the mutations detected by scRNA-seq to mutations detected by DNA-seq, ATAC-seq or RCA-seq in a bulk sample from the subject.
23. The method of any of paragraphs 18 to 22, further comprising determining the cell state of the single cells in the lineage and/or clonal structure by measuring the expression of the nuclear genome obtained by scRNA-seq.
24. The method of any of paragraphs 1 to 17, wherein detecting mutations in the mitochondrial genomes and/or nuclear genome of single cells comprises single cell ATAC-seq (scATAC-seq).
25. The method of paragraph 24, further comprising determining the cell state of the single cells in the lineage and/or clonal structure by measuring chromatin accessibility obtained by scATAC-seq.
26. The method of any of paragraphs 1 to 25, wherein heritable cell states are identified.
27. The method of any of paragraphs 1 to 26, wherein the establishment of a cell state along a lineage is identified.
28. The method of any of paragraphs 1 to 27, wherein the single cells comprise related cell types.
29. The method of paragraph 28, wherein the related cell types are from a tissue.
30. The method of paragraph 29, wherein the tissue is associated with a disease state.
31. The method of paragraph 30, wherein the disease is a degenerative disease.
32. The method of any of paragraphs 29 to 31, wherein the tissue is healthy tissue.
33. The method of any of paragraphs 29 to 31, wherein the tissue is diseased tissue.
34. The method of any of paragraphs 1 to 33, wherein the cells obtained from a subject are selected for a cell type.
35. The method of paragraph 34, wherein stem and progenitor cells are selected.
36. The method of paragraph 35, wherein CD34+ hematopoietic stem and progenitor cells are selected.
37. The method of any of paragraphs 1 to 28, further comprising determining a lineage and/or clonal structure for single cells from two or more tissues and identifying tissue specific mitochondrial mutations for the subject.
38. The method of paragraph 29, wherein the related cell types are from a tumor sample.
39. The method of paragraph 34, wherein peripheral blood mononuclear cells (PBMCs) and/or bone marrow mononuclear cells (BMMCs) are selected.
40. The method of paragraph 39, wherein PBMCs and/or bone marrow mononuclear cells are selected before and after stem cell transplantation in a subject.
41. A method of detecting clonal populations of cells in a tumor sample obtained from a subject in need thereof comprising determining the clonal structure for single cells in the tumor sample based on the presence of mutations according to any of paragraphs 1 to 27 and on the presence of somatic mutations associated with the cancer, whereby clonal populations of cells are identified based on the presence of the mitochondrial mutations and somatic mutations associated with the cancer in the single cells.
42. The method of paragraph 41, wherein the tumor sample is obtained before a cancer treatment.
43. The method of paragraph 42, further comprising obtaining a sample after treatment and comparing the presence of clonal populations before and after treatment, wherein clonal populations of cells sensitive and resistant to the treatment are identified.

44. The method of paragraphs 42 or 43, wherein the cancer treatment is selected from the group consisting of chemotherapy, radiation therapy, immunotherapy, targeted therapy and a combination thereof.

45. A method of identifying a cancer therapeutic target comprising:
   a) detecting clonal populations of cells in a tumor sample according to paragraph 43;
   b) identifying differential cell states between the clonal populations;
   c) identifying a cell state present in resistant clonal populations, thereby identifying a therapeutic target.

46. The method of paragraph 45, wherein the cell state is a differentially expressed gene, differentially expressed gene signature, or a differentially accessible chromatin loci.

47. A method of treatment comprising administering a treatment targeting a differentially expressed gene, differentially expressed gene signature, or a differentially accessible chromatin loci according to paragraph 46.

48. A method of screening for a cancer treatment comprising:
   a) growing a tumor sample obtained from a subject in need thereof,
   b) determining clonal populations in the tumor sample based on the presence of mutations according to any of paragraphs 1 to 27;
   c) treating the tumor sample with one or more agents;
   d) determining the effect of the one or more agents on the clonal populations.

49. The method according to paragraph 48, wherein the tumor cells are grown in vitro.

50. The method according to paragraph 48, wherein the tumor cells are grown in vivo.

51. The method according to paragraph 50, wherein the tumor cells are grown as a patient derived xenograft (PDX).

52. The method according to any of paragraphs 48 to 51, further comprising identifying differential cell states between sensitive and resistant clonal populations.

53. A method of identifying changes in clonal populations having a cell state between healthy and diseased tissue comprising determining clonal populations of cells having a cell state in healthy and diseased cells according to any of paragraphs 1 to 33 and comparing the clonal populations.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of determining a lineage and/or clonal structure of single cells in a multicellular eukaryotic organism comprising:
   a) detecting mutations in mitochondrial genome sequencing reads of single cells obtained from a subject; and
   b) clustering the cells based on the presence of the mutations in the single cells, whereby a lineage and/or clonal structure for the single cells is retrospectively inferred.

2. The method of claim 1, wherein the method comprises sequencing the mitochondrial genomes in single cells obtained from the subject.

3. The method of claim 1, wherein the mutations in step (a) are detected in at least 5 sequencing reads and have at least 0.5% heteroplasmy in the single cells obtained from the subject.

4. The method of claim 1, further comprising detecting mutations in mitochondrial genome sequencing reads of a bulk sample obtained from the subject, wherein step (a) further comprises selecting heteroplasmic mutations detected in the bulk sample.

5. The method of claim 4, wherein the method comprises sequencing mitochondrial genomes in a bulk sample obtained from the subject and/or
   wherein the selected mutations are detected in at least 5 sequencing reads and have at least 0.5% heteroplasmy in the bulk sample obtained from the subject.

6. The method of claim 1, wherein the mutations are detected in the D loop of the mitochondrial genomes; and/or
   wherein the method further comprises detecting mutations in the nuclear genome and clustering the cells based on the presence of the mitochondrial and nuclear genome mutations in the single cells; and/or
   wherein the detected mutations in step (a) have a Phred quality score greater than 20; and/or
   wherein the clustering is hierarchical clustering; and/or
   wherein the method further comprises generating a lineage map; and/or
   wherein detecting mutations in single cells comprises lysing the cells under conditions capable of lysing mitochondria.

7. The method of claim 6, wherein detecting mutations in the mitochondrial genomes and/or nuclear genome of single cells comprises single cell RNA sequencing (scRNA-seq).

8. The method of claim 6, wherein detecting mutations in the mitochondrial genomes and/or nuclear genome of single cells comprises single cell ATAC-seq (scATAC-seq).

9. The method of claim 1, wherein the single cells comprise related cell types.

10. The method of claim 1, wherein the cells obtained from a subject are selected for a cell type.

11. The method of claim 1, further comprising determining a lineage and/or clonal structure for single cells from two or more tissues and identifying tissue specific mitochondrial mutations for the subject.

12. A method of detecting clonal populations of cells in a tumor sample obtained from a subject in need thereof comprising determining the clonal structure for single cells in the tumor sample based on the presence of mutations according to claim 1 and on the presence of somatic mutations associated with the cancer, whereby clonal populations of cells are identified based on the presence of the mitochondrial mutations and somatic mutations associated with the cancer in the single cells.

13. A method of identifying a cancer therapeutic target comprising:
   a) detecting clonal populations of cells in a tumor sample according to claim 12;
   b) identifying differential cell states between the clonal populations;
   c) identifying a cell state present in resistant clonal populations, thereby identifying a therapeutic target.

14. A method of treatment comprising administering a treatment targeting a differentially expressed gene, differentially expressed gene signature, or a differentially accessible chromatin loci, wherein the method comprises identifying a cancer therapeutic target according to claim 13, and administering the treatment to a subject in need thereof.

15. A method of screening for a cancer treatment comprising:
   a) growing a tumor sample obtained from a subject in need thereof;
   b) determining clonal populations in the tumor sample based on the presence of mutations according to claim 1;
   c) treating the tumor sample with one or more agents;
   d) determining the effect of the one or more agents on the clonal populations.

16. A method of identifying changes in clonal populations having a cell state between healthy and diseased tissue comprising determining clonal populations of cells having a cell state in healthy and diseased cells according to claim 1 and comparing the clonal populations.

17. The method according to claim 1, wherein nuclei isolated from the single cells are used.

18. The method of claim 9, wherein the related cell types are from a tissue.

19. The method of claim 10, wherein the cell type selected for is stem and progenitor cells.

20. The method of claim 15, wherein the method further comprises identifying differential cell states between sensitive and resistant clonal populations.

21. The method of claim 3, wherein the mutations have at least 5% heteroplasmy in the single cells obtained from the subject.

22. The method of claim 6, wherein the method comprises sequencing the nuclear genome in single cells obtained from the subject.

23. The method of claim 7, wherein detecting mutations in the mitochondrial genomes and/or nuclear genome comprises analyzing scRNA-seq data obtained from a subject; and/or
   wherein the method further comprises excluding RNA modification, RNA transcription errors and/or RNA sequencing errors from the mutations detected.

24. The method of claim 23, wherein the RNA modifications comprise previously identified RNA modifications; and/or wherein RNA modifications, RNA transcription errors and/or RNA sequencing errors are determined by comparing the mutations detected by scRNA-seq to mutation detected by DNA-seq, ATAC-seq or RCA-seq in a bulk sample from the subject; and/or
   wherein the method further comprises determining the cell state of the single cells in the lineage and/or clonal structure by measuring the expression of the nuclear genome obtained by scRNA-seq.

25. The method of claim 8, wherein the method further comprises determining the cell state of the single cells in the lineage and/or clonal structure by measuring chromatin accessibility obtained by scATAC-seq.

26. The method of claim 12, wherein the tumor sample is obtained before and/or after a cancer treatment.

27. The method of claim 15, wherein the tumor sample obtained from a subject in need thereof comprises tumor cells grown in vitro; or
   wherein the tumor cells are grown in vivo; or
   wherein the tumor cells are grown as a patient derived xenograft (PDX).

\* \* \* \* \*